US012724028B2

(12) United States Patent
Hodge et al.

(10) Patent No.: US 12,724,028 B2
(45) Date of Patent: Sep. 1, 2026

(54) SELF-ASSEMBLING PROTEIN NANOCAGE DECORATED WITH ANTIBODIES (SAPNA) AND PARTS THEREOF

(71) Applicant: The Regents of the University of California, Oakland, CA (US)

(72) Inventors: Curtis D. Hodge, Berkeley, CA (US); Gregory L. Hura, Berkeley, CA (US); Todd O. Yeates, Agoura Hills, CA (US)

(73) Assignee: The Regents of the University of California, Oakland, CA (US)

( * ) Notice: Subject to any disclaimer, the term of this patent is extended or adjusted under 35 U.S.C. 154(b) by 1311 days.

(21) Appl. No.: 17/606,391

(22) PCT Filed: Apr. 27, 2020

(86) PCT No.: PCT/US2020/030142

§ 371 (c)(1),
(2) Date: Oct. 25, 2021

(87) PCT Pub. No.: WO2020/220044

PCT Pub. Date: Oct. 29, 2020

(65) Prior Publication Data

US 2022/0196655 A1 Jun. 23, 2022

Related U.S. Application Data

(60) Provisional application No. 62/838,826, filed on Apr. 25, 2019.

(51) Int. Cl.
*G01N 33/569* (2006.01)
*G01N 33/68* (2006.01)

(52) U.S. Cl.
CPC ....... *G01N 33/569* (2013.01); *G01N 33/6854* (2013.01)

(58) Field of Classification Search
None
See application file for complete search history.

(56) References Cited

U.S. PATENT DOCUMENTS

| | | | |
|---|---|---|---|
| 2006/0078951 | A1 | 4/2006 | Youn et al. |
| 2016/0311859 | A1 | 10/2016 | Jerala et al. |

FOREIGN PATENT DOCUMENTS

| | | | | |
|---|---|---|---|---|
| EP | 2824112 | B1 | 12/2016 | |
| WO | 2000/68248 | A2 | 11/2000 | |
| WO | 2001/45746 | A2 | 6/2001 | |
| WO | 2004056392 | A1 | 7/2004 | |
| WO | 2006138670 | A2 | 12/2006 | |
| WO | 2013/052015 | A1 | 4/2013 | |
| WO | 2014/124301 | A1 | 8/2014 | |
| WO | 2016037154 | A1 | 3/2016 | |
| WO | 2018/170362 | A2 | 9/2018 | |
| WO | WO-2018172447 | A1 * | 9/2018 | ............. A61K 39/12 |
| WO | 2005049085 | A1 | 6/2025 | |

OTHER PUBLICATIONS

Sivori, et al., "p46, a Novel Natural Killer Cell-specific Surface Molecule That Mediates Cell Activation," J. Exp. Med., 1997, vol. 186, No. 7, pp. 1129-1136.
Sivori, et al., "NKp46 is the major triggering receptor involved in the natural cytotoxicity of fresh or cultured human NK cells. Correlation between surface density of NKp46 and natural cytotoxicity against autologous, allogeneic or xenogeneic target cells," Eur. J. Immunol. 1999, 29: pp. 1656-1666.w.
Lai, et al., "Structure and Flexibility of Nanoscale Protein Cages Designed by Symmetric Self-Assembly," J Am Chem Soc 2013, 135(20), pp. 7738-7743.
Liu, et al. "Near-atomic cryo-EM imaging of a small protein displayed on a designed scaffolding system," PNAS, 2018, vol. 115, No. 13, pp. 3362-3367.
Liu, et al., "A 3.8 A resolution cryo-EM structure of a small protein bound to an imaging scaffold," Nature Communications, 2019, 10:1864, pp. 1-7.
PCT/US2020/030142, International Search Report and Written Opinion, dated Jan. 19, 2021, 17 pages.
Kang et al., "Developing an antibody-binding protein cage as a molecular recognition drug modular nanoplatform," Biomaterials, vol. 33, No. 21, pp. 5423-5430, Jul. 2012.
Lai et al., "Designing and defining dynamic protein cage nanoassembliesin solution," Science Advances, vol. 2, pp. 1-12, Dec. 2016.

* cited by examiner

*Primary Examiner* — Nicole Kinsey White
(74) *Attorney, Agent, or Firm* — Kilpatrick Townsend & Stockton LLP

(57) ABSTRACT

The present invention provides for a protein cage polypeptide (or scaffolding protein) useful or capable of forming a hollow tetrahedral pyramid structure, and a "self-assembling protein nanoparticle decorated with antibodies" (SAPNA) which is a chimeric protein assembly comprising: (a) one or more antibodies and (b) the protein cage polypeptide that provides a scaffold upon which to array the antibodies. In some embodiments, the antibody is capable of binding specifically to a pathogenic biological agent, or part thereof.

31 Claims, 14 Drawing Sheets

Specification includes a Sequence Listing.

```
        ****    ****** *    **** ** ******* * **  * ** *********
MPFITVGQENSTSIDLYYEDHGTGTPVVLIHGFPLSGHSWERQSAALLDAGYRVITYDRRGFGQ
1                                                             64

***** * ****** **      *     *****  ****       *****    *** ** *
SSQPTTGYDYDTFAADLNTVLETLDLQDAVLVGFSMGTGEVARYVSSYGTARIAAVAFLASLEP
                                                             128

               #                           #
 *  ***** * *   ** *       ******* *   * ** ********************
FLLKTDDNPDGAAPQEFFDGIVAAVKADRYAFYTGFFNDFYNLDENLGTRISEEAVRNSWNTAA
                                                             192

                                    #     #
* ***** ***  * **** *   **** ** **** ****   * * *   **** * *  **
SGGFFAAAAAPTTWYTDFRADIPRIDVPALILHGTGDRTLPIENTARVFHKALPSAEYVEVEGA
                                                             256

                      @@@@@@@@
                                                             $^^
* ******   ** **  *            **********  ******* ***  * ** *
PHGLLWTHAEEVNTALLAFLAKAQEAQKQKLLTEVETYVLSIIPSGPLKAEIAQRLEDVFAGKN
                                                             320

^$
 ***  *** ******* **** *** ************* ** * ** ***** *** ** **
TDLEVLMEWLKTRPILSPLTKGILGFVFTLTVPSERGLQRRRFVQNALNGNGDPNNMDKAVKLY
                                                             384

                                                         $^^^^^^
****** *******    ** *** ******** ** *  * * ** *********
RKLKREITFHGAKEISLSYSAGALASCMGLIYNRMGAVTTEVAFGLVCATCEQIADSQHRSHRQ
                                                             448

$

LEHHHHHH
     456
```

FIG. 6

Scattering Intensity 1
0
-1
-2
-3
-4

0.1
0.2
0.3

Scattering angle q ($Å^{-1}$)

Scaffold

Scaffold-A488

- Prototype maintains tetrahedral form
- Labeling with AlexaFluor-488 does not disrupt structure

SEQUENCE LISTING

```
<160> NUMBER OF SEQ ID NOS: 45

<210> SEQ ID NO 1
<211> LENGTH: 472
<212> TYPE: PRT
<213> ORGANISM: Artificial Sequence
<220> FEATURE:
<223> OTHER INFORMATION: Engineered Self-Assembling Protein Nanocage
      SAPNA_1

<400> SEQUENCE: 1

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Gly Cys Asp Cys Ala Trp His Leu Gly Glu Leu
    130                 135                 140

Val Trp Cys Thr Cys Gly Asp Asn Pro Asp Gly Ala Ala Pro Gln Glu
145                 150                 155                 160

Phe Phe Asp Gly Ile Val Ala Ala Val Lys Ala Asp Arg Tyr Ala Phe
                165                 170                 175

Tyr Thr Gly Phe Phe Asn Asp Phe Tyr Asn Leu Asp Glu Asn Leu Gly
            180                 185                 190

Thr Arg Ile Ser Glu Glu Ala Val Arg Asn Ser Trp Asn Thr Ala Ala
        195                 200                 205

Ser Gly Gly Phe Phe Ala Ala Ala Ala Ala Pro Thr Thr Trp Tyr Thr
    210                 215                 220

Asp Phe Arg Ala Asp Ile Pro Arg Ile Asp Val Pro Ala Leu Ile Leu
225                 230                 235                 240
```

```
His Gly Thr Gly Asp Arg Thr Leu Pro Ile Glu Asn Thr Ala Arg Val
                245                 250                 255

Phe His Lys Ala Leu Pro Ser Ala Glu Tyr Val Glu Val Glu Gly Ala
            260                 265                 270

Pro His Gly Leu Leu Trp Thr His Ala Glu Glu Val Asn Thr Ala Leu
        275                 280                 285

Leu Ala Phe Leu Ala Lys Ala Gln Glu Ala Gln Lys Gln Lys Leu Leu
    290                 295                 300

Thr Glu Val Glu Thr Tyr Val Leu Ser Ile Ile Pro Ser Gly Pro Leu
305                 310                 315                 320

Lys Ala Glu Ile Ala Gln Arg Leu Glu Asp Val Phe Ala Gly Lys Asn
                325                 330                 335

Thr Asp Leu Glu Val Leu Met Glu Trp Leu Lys Thr Arg Pro Ile Leu
            340                 345                 350

Ser Pro Leu Thr Lys Gly Ile Leu Gly Phe Val Phe Thr Leu Thr Val
        355                 360                 365

Pro Ser Glu Arg Gly Leu Gln Arg Arg Arg Phe Val Gln Asn Ala Leu
    370                 375                 380

Asn Gly Asn Gly Asp Pro Asn Asn Met Asp Lys Ala Val Lys Leu Tyr
385                 390                 395                 400

Arg Lys Leu Lys Arg Glu Ile Thr Phe His Gly Ala Lys Glu Ile Ser
                405                 410                 415

Leu Ser Tyr Ser Ala Gly Ala Leu Ala Ser Cys Met Gly Leu Ile Tyr
            420                 425                 430

Asn Arg Met Gly Ala Val Thr Thr Glu Val Ala Phe Gly Leu Val Cys
        435                 440                 445

Ala Thr Cys Glu Gln Ile Ala Asp Ser Gln His Arg Ser His Arg Gln
    450                 455                 460

Leu Glu His His His His His His
465                 470


<210> SEQ ID NO 2
<211> LENGTH: 473
<212> TYPE: PRT
<213> ORGANISM: Artificial Sequence
<220> FEATURE:
<223> OTHER INFORMATION: Engineered Self-Assembling Protein Nanocage
      SAPNA_2

<400> SEQUENCE: 2

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
```

```
        115                 120                 125

Phe Leu Leu Lys Thr Gly Cys Asp Cys Ala Trp His Leu Gly Glu Leu
    130                 135                 140

Val Trp Cys Thr Cys Gly Asp Asn Pro Asp Gly Ala Ala Pro Gln Glu
145                 150                 155                 160

Phe Phe Asp Gly Ile Val Ala Ala Val Lys Ala Asp Arg Tyr Ala Phe
                165                 170                 175

Tyr Thr Gly Phe Phe Asn Asp Phe Tyr Asn Leu Asp Glu Asn Leu Gly
            180                 185                 190

Thr Arg Ile Ser Glu Glu Ala Val Arg Asn Ser Trp Asn Thr Ala Ala
        195                 200                 205

Ser Gly Gly Phe Phe Ala Ala Ala Ala Ala Pro Thr Thr Trp Tyr Thr
    210                 215                 220

Asp Phe Arg Ala Asp Ile Pro Arg Ile Asp Val Pro Ala Leu Ile Leu
225                 230                 235                 240

His Gly Thr Gly Asp Arg Thr Leu Pro Ile Glu Asn Thr Ala Arg Val
                245                 250                 255

Phe His Lys Ala Leu Pro Ser Ala Glu Tyr Val Glu Val Glu Gly Ala
            260                 265                 270

Pro His Gly Leu Leu Trp Thr His Ala Glu Glu Val Asn Thr Ala Leu
        275                 280                 285

Leu Ala Phe Leu Ala Lys Ala Gln Glu Ala Gln Lys Gln Lys Leu Leu
    290                 295                 300

Thr Glu Val Glu Thr Tyr Val Leu Ser Ile Ile Pro Ser Gly Pro Leu
305                 310                 315                 320

Lys Ala Glu Ile Ala Gln Arg Leu Glu Asp Val Phe Ala Gly Lys Asn
                325                 330                 335

Thr Asp Leu Glu Val Leu Met Glu Trp Leu Lys Thr Arg Pro Ile Leu
            340                 345                 350

Ser Pro Leu Thr Lys Gly Ile Leu Gly Phe Val Phe Thr Leu Thr Val
        355                 360                 365

Pro Ser Glu Arg Gly Leu Gln Arg Arg Arg Phe Val Gln Asn Ala Leu
    370                 375                 380

Asn Gly Asn Gly Asp Pro Asn Asn Met Asp Lys Ala Val Lys Leu Tyr
385                 390                 395                 400

Arg Lys Leu Lys Arg Glu Ile Thr Phe His Gly Ala Lys Glu Ile Ser
                405                 410                 415

Leu Ser Tyr Ser Ala Gly Ala Leu Ala Ser Cys Met Gly Leu Ile Tyr
            420                 425                 430

Asn Arg Met Gly Ala Val Thr Thr Glu Val Ala Phe Gly Leu Val Cys
        435                 440                 445

Ala Thr Cys Glu Gln Ile Ala Asp Ser Gln Glu Asn Leu Tyr Phe Gln
    450                 455                 460

Gly Leu Glu His His His His His His
465                 470
```

<210> SEQ ID NO 3
<211> LENGTH: 480
<212> TYPE: PRT
<213> ORGANISM: Artificial Sequence
<220> FEATURE:
<223> OTHER INFORMATION: Engineered Self-Assembling Protein Nanocage
      SAPNA_3

<400> SEQUENCE: 3

-continued

```
Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Gly Gly Gly Ser Gly Cys Asp Cys Ala Trp His
    130                 135                 140

Leu Gly Glu Leu Val Trp Cys Thr Cys Gly Ser Gly Gly Gly Asp Asn
145                 150                 155                 160

Pro Asp Gly Ala Ala Pro Gln Glu Phe Phe Asp Gly Ile Val Ala Ala
                165                 170                 175

Val Lys Ala Asp Arg Tyr Ala Phe Tyr Thr Gly Phe Phe Asn Asp Phe
            180                 185                 190

Tyr Asn Leu Asp Glu Asn Leu Gly Thr Arg Ile Ser Glu Glu Ala Val
        195                 200                 205

Arg Asn Ser Trp Asn Thr Ala Ala Ser Gly Gly Phe Phe Ala Ala Ala
    210                 215                 220

Ala Ala Pro Thr Thr Trp Tyr Thr Asp Phe Arg Ala Asp Ile Pro Arg
225                 230                 235                 240

Ile Asp Val Pro Ala Leu Ile Leu His Gly Thr Gly Asp Arg Thr Leu
                245                 250                 255

Pro Ile Glu Asn Thr Ala Arg Val Phe His Lys Ala Leu Pro Ser Ala
            260                 265                 270

Glu Tyr Val Glu Val Glu Gly Ala Pro His Gly Leu Leu Trp Thr His
        275                 280                 285

Ala Glu Glu Val Asn Thr Ala Leu Leu Ala Phe Leu Ala Lys Ala Gln
    290                 295                 300

Glu Ala Gln Lys Gln Lys Leu Leu Thr Glu Val Glu Thr Tyr Val Leu
305                 310                 315                 320

Ser Ile Ile Pro Ser Gly Pro Leu Lys Ala Glu Ile Ala Gln Arg Leu
                325                 330                 335

Glu Asp Val Phe Ala Gly Lys Asn Thr Asp Leu Glu Val Leu Met Glu
            340                 345                 350

Trp Leu Lys Thr Arg Pro Ile Leu Ser Pro Leu Thr Lys Gly Ile Leu
        355                 360                 365

Gly Phe Val Phe Thr Leu Thr Val Pro Ser Glu Arg Gly Leu Gln Arg
    370                 375                 380

Arg Arg Phe Val Gln Asn Ala Leu Asn Gly Asn Gly Asp Pro Asn Asn
385                 390                 395                 400

Met Asp Lys Ala Val Lys Leu Tyr Arg Lys Leu Lys Arg Glu Ile Thr
                405                 410                 415

Phe His Gly Ala Lys Glu Ile Ser Leu Ser Tyr Ser Ala Gly Ala Leu
```

-continued

```
            420                 425                 430

Ala Ser Cys Met Gly Leu Ile Tyr Asn Arg Met Gly Ala Val Thr Thr
        435                 440                 445

Glu Val Ala Phe Gly Leu Val Cys Ala Thr Cys Glu Gln Ile Ala Asp
    450                 455                 460

Ser Gln His Arg Ser His Arg Gln Leu Glu His His His His His His
465                 470                 475                 480


<210> SEQ ID NO 4
<211> LENGTH: 481
<212> TYPE: PRT
<213> ORGANISM: Artificial Sequence
<220> FEATURE:
<223> OTHER INFORMATION: Engineered Self-Assembling Protein Nanocage
      SAPNA_4

<400> SEQUENCE: 4

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Gly Gly Gly Ser Gly Cys Asp Cys Ala Trp His
    130                 135                 140

Leu Gly Glu Leu Val Trp Cys Thr Cys Gly Ser Gly Gly Gly Asp Asn
145                 150                 155                 160

Pro Asp Gly Ala Ala Pro Gln Glu Phe Phe Asp Gly Ile Val Ala Ala
                165                 170                 175

Val Lys Ala Asp Arg Tyr Ala Phe Tyr Thr Gly Phe Phe Asn Asp Phe
            180                 185                 190

Tyr Asn Leu Asp Glu Asn Leu Gly Thr Arg Ile Ser Glu Glu Ala Val
        195                 200                 205

Arg Asn Ser Trp Asn Thr Ala Ala Ser Gly Gly Phe Phe Ala Ala Ala
    210                 215                 220

Ala Ala Pro Thr Thr Trp Tyr Thr Asp Phe Arg Ala Asp Ile Pro Arg
225                 230                 235                 240

Ile Asp Val Pro Ala Leu Ile Leu His Gly Thr Gly Asp Arg Thr Leu
                245                 250                 255

Pro Ile Glu Asn Thr Ala Arg Val Phe His Lys Ala Leu Pro Ser Ala
            260                 265                 270

Glu Tyr Val Glu Val Glu Gly Ala Pro His Gly Leu Leu Trp Thr His
        275                 280                 285

Ala Glu Glu Val Asn Thr Ala Leu Leu Ala Phe Leu Ala Lys Ala Gln
    290                 295                 300
```

-continued

Glu Ala Gln Lys Gln Lys Leu Leu Thr Glu Val Glu Thr Tyr Val Leu
305 310 315 320

Ser Ile Ile Pro Ser Gly Pro Leu Lys Ala Glu Ile Ala Gln Arg Leu
325 330 335

Glu Asp Val Phe Ala Gly Lys Asn Thr Asp Leu Glu Val Leu Met Glu
340 345 350

Trp Leu Lys Thr Arg Pro Ile Leu Ser Pro Leu Thr Lys Gly Ile Leu
355 360 365

Gly Phe Val Phe Thr Leu Thr Val Pro Ser Glu Arg Gly Leu Gln Arg
370 375 380

Arg Arg Phe Val Gln Asn Ala Leu Asn Gly Asn Gly Asp Pro Asn Asn
385 390 395 400

Met Asp Lys Ala Val Lys Leu Tyr Arg Lys Leu Lys Arg Glu Ile Thr
405 410 415

Phe His Gly Ala Lys Glu Ile Ser Leu Ser Tyr Ser Ala Gly Ala Leu
420 425 430

Ala Ser Cys Met Gly Leu Ile Tyr Asn Arg Met Gly Ala Val Thr Thr
435 440 445

Glu Val Ala Phe Gly Leu Val Cys Ala Thr Cys Glu Gln Ile Ala Asp
450 455 460

Ser Gln Glu Asn Leu Tyr Phe Gln Gly Leu Glu His His His His His
465 470 475 480

His

<210> SEQ ID NO 5
<211> LENGTH: 472
<212> TYPE: PRT
<213> ORGANISM: Artificial Sequence
<220> FEATURE:
<223> OTHER INFORMATION: Engineered Self-Assembling Protein Nanocage
SAPNA_5

<400> SEQUENCE: 5

Met Pro Phe Ile Thr Val Gly Gln Glu Asn Ser Thr Ser Ile Asp Leu
1 5 10 15

Tyr Tyr Glu Asp His Gly Thr Gly Thr Pro Val Val Leu Ile His Gly
20 25 30

Phe Pro Leu Ser Gly His Ser Trp Glu Arg Gln Ser Ala Ala Leu Leu
35 40 45

Asp Ala Gly Ala Arg Val Ile Thr Tyr Asp Arg Arg Gly Phe Gly Gln
50 55 60

Ser Ser Gln Pro Thr Thr Gly Tyr Asp Tyr Asp Thr Phe Ala Ala Asp
65 70 75 80

Leu Asn Thr Val Leu Glu Thr Leu Asp Leu Gln Asp Ala Val Leu Val
85 90 95

Gly Phe Ser Met Gly Thr Gly Glu Val Ala Arg Tyr Val Ser Ser Tyr
100 105 110

Gly Thr Ala Arg Ile Ala Ala Val Ala Phe Leu Ala Ser Leu Glu Pro
115 120 125

Phe Leu Leu Lys Thr Gly Cys Asp Cys Ala Trp His Leu Gly Glu Leu
130 135 140

Val Trp Cys Thr Cys Gly Asp Asn Pro Asp Gly Ala Ala Pro Gln Glu
145 150 155 160

Phe Phe Asp Gly Ile Val Ala Ala Val Lys Ala Asp Arg Tyr Ala Phe
165 170 175

-continued

```
Tyr Thr Gly Phe Phe Asn Asp Phe Tyr Asn Leu Asp Glu Asn Leu Gly
            180                 185                 190

Thr Arg Ile Ser Glu Glu Ala Val Arg Asn Ser Trp Asn Thr Ala Ala
        195                 200                 205

Ser Gly Gly Phe Phe Ala Ala Ala Ala Ala Pro Thr Thr Trp Tyr Thr
    210                 215                 220

Asp Phe Arg Ala Asp Ile Pro Arg Ile Asp Val Pro Ala Leu Ile Leu
225                 230                 235                 240

His Gly Thr Gly Asp Arg Thr Leu Pro Ile Glu Asn Thr Ala Arg Val
                245                 250                 255

Phe His Lys Ala Leu Pro Ser Ala Glu Tyr Val Glu Val Glu Gly Ala
            260                 265                 270

Pro His Gly Leu Leu Trp Thr His Ala Glu Glu Val Asn Thr Ala Leu
        275                 280                 285

Leu Ala Phe Leu Ala Lys Ala Gln Glu Ala Gln Lys Gln Lys Leu Leu
    290                 295                 300

Thr Glu Val Glu Thr Tyr Val Leu Ser Ile Ile Pro Ser Gly Pro Leu
305                 310                 315                 320

Lys Ala Glu Ile Ala Gln Arg Leu Glu Asp Val Phe Ala Gly Lys Asn
                325                 330                 335

Thr Asp Leu Glu Val Leu Met Glu Trp Leu Lys Thr Arg Pro Ile Leu
            340                 345                 350

Ser Pro Leu Thr Lys Gly Ile Leu Gly Phe Val Phe Thr Leu Thr Val
        355                 360                 365

Pro Ser Glu Arg Gly Leu Gln Arg Arg Arg Phe Val Gln Asn Ala Leu
    370                 375                 380

Asn Gly Asn Gly Asp Pro Asn Asn Met Asp Lys Ala Val Lys Leu Tyr
385                 390                 395                 400

Arg Lys Leu Lys Arg Glu Ile Thr Phe His Gly Ala Lys Glu Ile Ser
                405                 410                 415

Leu Ser Tyr Ser Ala Gly Ala Leu Ala Ser Cys Met Gly Leu Ile Tyr
            420                 425                 430

Asn Arg Met Gly Ala Val Thr Thr Glu Val Ala Phe Gly Leu Val Cys
        435                 440                 445

Ala Thr Cys Glu Gln Ile Ala Asp Ser Gln His Arg Ser His Arg Gln
    450                 455                 460

Leu Glu His His His His His His
465                 470
```

<210> SEQ ID NO 6
<211> LENGTH: 473
<212> TYPE: PRT
<213> ORGANISM: Artificial Sequence
<220> FEATURE:
<223> OTHER INFORMATION: Engineered Self-Assembling Protein Nanocage SAPNA_6

<400> SEQUENCE: 6

```
Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Ala Arg Val Ile Thr Tyr Asp Arg Arg Gly Phe Gly Gln
    50                  55                  60
```

-continued

```
Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Gly Cys Asp Cys Ala Trp His Leu Gly Glu Leu
    130                 135                 140

Val Trp Cys Thr Cys Gly Asp Asn Pro Asp Gly Ala Ala Pro Gln Glu
145                 150                 155                 160

Phe Phe Asp Gly Ile Val Ala Ala Val Lys Ala Asp Arg Tyr Ala Phe
                165                 170                 175

Tyr Thr Gly Phe Phe Asn Asp Phe Tyr Asn Leu Asp Glu Asn Leu Gly
            180                 185                 190

Thr Arg Ile Ser Glu Glu Ala Val Arg Asn Ser Trp Asn Thr Ala Ala
        195                 200                 205

Ser Gly Gly Phe Phe Ala Ala Ala Ala Ala Pro Thr Thr Trp Tyr Thr
    210                 215                 220

Asp Phe Arg Ala Asp Ile Pro Arg Ile Asp Val Pro Ala Leu Ile Leu
225                 230                 235                 240

His Gly Thr Gly Asp Arg Thr Leu Pro Ile Glu Asn Thr Ala Arg Val
                245                 250                 255

Phe His Lys Ala Leu Pro Ser Ala Glu Tyr Val Glu Val Glu Gly Ala
            260                 265                 270

Pro His Gly Leu Leu Trp Thr His Ala Glu Glu Val Asn Thr Ala Leu
        275                 280                 285

Leu Ala Phe Leu Ala Lys Ala Gln Glu Ala Gln Lys Gln Lys Leu Leu
    290                 295                 300

Thr Glu Val Glu Thr Tyr Val Leu Ser Ile Ile Pro Ser Gly Pro Leu
305                 310                 315                 320

Lys Ala Glu Ile Ala Gln Arg Leu Glu Asp Val Phe Ala Gly Lys Asn
                325                 330                 335

Thr Asp Leu Glu Val Leu Met Glu Trp Leu Lys Thr Arg Pro Ile Leu
            340                 345                 350

Ser Pro Leu Thr Lys Gly Ile Leu Gly Phe Val Phe Thr Leu Thr Val
        355                 360                 365

Pro Ser Glu Arg Gly Leu Gln Arg Arg Arg Phe Val Gln Asn Ala Leu
    370                 375                 380

Asn Gly Asn Gly Asp Pro Asn Asn Met Asp Lys Ala Val Lys Leu Tyr
385                 390                 395                 400

Arg Lys Leu Lys Arg Glu Ile Thr Phe His Gly Ala Lys Glu Ile Ser
                405                 410                 415

Leu Ser Tyr Ser Ala Gly Ala Leu Ala Ser Cys Met Gly Leu Ile Tyr
            420                 425                 430

Asn Arg Met Gly Ala Val Thr Thr Glu Val Ala Phe Gly Leu Val Cys
        435                 440                 445

Ala Thr Cys Glu Gln Ile Ala Asp Ser Gln Glu Asn Leu Tyr Phe Gln
    450                 455                 460

Gly Leu Glu His His His His His His
465                 470
```

-continued

<210> SEQ ID NO 7
<211> LENGTH: 480
<212> TYPE: PRT
<213> ORGANISM: Artificial Sequence
<220> FEATURE:
<223> OTHER INFORMATION: Engineered Self-Assembling Protein Nanocage SAPNA_7

<400> SEQUENCE: 7

```
Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Ala Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Gly Gly Gly Ser Gly Cys Asp Cys Ala Trp His
    130                 135                 140

Leu Gly Glu Leu Val Trp Cys Thr Cys Gly Ser Gly Gly Gly Asp Asn
145                 150                 155                 160

Pro Asp Gly Ala Ala Pro Gln Glu Phe Phe Asp Gly Ile Val Ala Ala
                165                 170                 175

Val Lys Ala Asp Arg Tyr Ala Phe Tyr Thr Gly Phe Phe Asn Asp Phe
            180                 185                 190

Tyr Asn Leu Asp Glu Asn Leu Gly Thr Arg Ile Ser Glu Glu Ala Val
        195                 200                 205

Arg Asn Ser Trp Asn Thr Ala Ala Ser Gly Gly Phe Phe Ala Ala Ala
    210                 215                 220

Ala Ala Pro Thr Thr Trp Tyr Thr Asp Phe Arg Ala Asp Ile Pro Arg
225                 230                 235                 240

Ile Asp Val Pro Ala Leu Ile Leu His Gly Thr Gly Asp Arg Thr Leu
                245                 250                 255

Pro Ile Glu Asn Thr Ala Arg Val Phe His Lys Ala Leu Pro Ser Ala
            260                 265                 270

Glu Tyr Val Glu Val Glu Gly Ala Pro His Gly Leu Leu Trp Thr His
        275                 280                 285

Ala Glu Glu Val Asn Thr Ala Leu Leu Ala Phe Leu Ala Lys Ala Gln
    290                 295                 300

Glu Ala Gln Lys Gln Lys Leu Leu Thr Glu Val Glu Thr Tyr Val Leu
305                 310                 315                 320

Ser Ile Ile Pro Ser Gly Pro Leu Lys Ala Glu Ile Ala Gln Arg Leu
                325                 330                 335

Glu Asp Val Phe Ala Gly Lys Asn Thr Asp Leu Glu Val Leu Met Glu
            340                 345                 350

Trp Leu Lys Thr Arg Pro Ile Leu Ser Pro Leu Thr Lys Gly Ile Leu
        355                 360                 365
```

Gly Phe Val Phe Thr Leu Thr Val Pro Ser Glu Arg Gly Leu Gln Arg
    370                 375                 380

Arg Arg Phe Val Gln Asn Ala Leu Asn Gly Asn Gly Asp Pro Asn Asn
385                 390                 395                 400

Met Asp Lys Ala Val Lys Leu Tyr Arg Lys Leu Lys Arg Glu Ile Thr
                405                 410                 415

Phe His Gly Ala Lys Glu Ile Ser Leu Ser Tyr Ser Ala Gly Ala Leu
            420                 425                 430

Ala Ser Cys Met Gly Leu Ile Tyr Asn Arg Met Gly Ala Val Thr Thr
        435                 440                 445

Glu Val Ala Phe Gly Leu Val Cys Ala Thr Cys Glu Gln Ile Ala Asp
    450                 455                 460

Ser Gln His Arg Ser His Arg Gln Leu Glu His His His His His His
465                 470                 475                 480

<210> SEQ ID NO 8
<211> LENGTH: 481
<212> TYPE: PRT
<213> ORGANISM: Artificial Sequence
<220> FEATURE:
<223> OTHER INFORMATION: Engineered Self-Assembling Protein Nanocage
      SAPNA_8

<400> SEQUENCE: 8

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Ala Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Gly Gly Gly Ser Gly Cys Asp Cys Ala Trp His
    130                 135                 140

Leu Gly Glu Leu Val Trp Cys Thr Cys Gly Ser Gly Gly Gly Asp Asn
145                 150                 155                 160

Pro Asp Gly Ala Ala Pro Gln Glu Phe Phe Asp Gly Ile Val Ala Ala
                165                 170                 175

Val Lys Ala Asp Arg Tyr Ala Phe Tyr Thr Gly Phe Phe Asn Asp Phe
            180                 185                 190

Tyr Asn Leu Asp Glu Asn Leu Gly Thr Arg Ile Ser Glu Glu Ala Val
        195                 200                 205

Arg Asn Ser Trp Asn Thr Ala Ala Ser Gly Gly Phe Phe Ala Ala Ala
    210                 215                 220

Ala Ala Pro Thr Thr Trp Tyr Thr Asp Phe Arg Ala Asp Ile Pro Arg
225                 230                 235                 240

Ile Asp Val Pro Ala Leu Ile Leu His Gly Thr Gly Asp Arg Thr Leu

```
                245                 250                 255

Pro Ile Glu Asn Thr Ala Arg Val Phe His Lys Ala Leu Pro Ser Ala
            260                 265                 270

Glu Tyr Val Glu Val Glu Gly Ala Pro His Gly Leu Leu Trp Thr His
        275                 280                 285

Ala Glu Glu Val Asn Thr Ala Leu Leu Ala Phe Leu Ala Lys Ala Gln
    290                 295                 300

Glu Ala Gln Lys Gln Lys Leu Leu Thr Glu Val Glu Thr Tyr Val Leu
305                 310                 315                 320

Ser Ile Ile Pro Ser Gly Pro Leu Lys Ala Glu Ile Ala Gln Arg Leu
                325                 330                 335

Glu Asp Val Phe Ala Gly Lys Asn Thr Asp Leu Glu Val Leu Met Glu
            340                 345                 350

Trp Leu Lys Thr Arg Pro Ile Leu Ser Pro Leu Thr Lys Gly Ile Leu
        355                 360                 365

Gly Phe Val Phe Thr Leu Thr Val Pro Ser Glu Arg Gly Leu Gln Arg
    370                 375                 380

Arg Arg Phe Val Gln Asn Ala Leu Asn Gly Asn Gly Asp Pro Asn Asn
385                 390                 395                 400

Met Asp Lys Ala Val Lys Leu Tyr Arg Lys Leu Lys Arg Glu Ile Thr
                405                 410                 415

Phe His Gly Ala Lys Glu Ile Ser Leu Ser Tyr Ser Ala Gly Ala Leu
            420                 425                 430

Ala Ser Cys Met Gly Leu Ile Tyr Asn Arg Met Gly Ala Val Thr Thr
        435                 440                 445

Glu Val Ala Phe Gly Leu Val Cys Ala Thr Cys Glu Gln Ile Ala Asp
    450                 455                 460

Ser Gln Glu Asn Leu Tyr Phe Gln Gly Leu Glu His His His His His
465                 470                 475                 480

His


<210> SEQ ID NO 9
<211> LENGTH: 478
<212> TYPE: PRT
<213> ORGANISM: Artificial Sequence
<220> FEATURE:
<223> OTHER INFORMATION: Engineered Self-Assembling Protein Nanocage
      SAPNA_9

<400> SEQUENCE: 9

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
```

-continued

```
        115                 120                 125

Phe Leu Leu Lys Thr Gly Arg Trp Gly Cys Asp Cys Ala Trp His Leu
    130                 135                 140

Gly Glu Leu Val Trp Cys Thr Cys Gly Trp Glu Gly Asp Asn Pro Asp
145                 150                 155                 160

Gly Ala Ala Pro Gln Glu Phe Phe Asp Gly Ile Val Ala Ala Val Lys
                165                 170                 175

Ala Asp Arg Tyr Ala Phe Tyr Thr Gly Phe Phe Asn Asp Phe Tyr Asn
            180                 185                 190

Leu Asp Glu Asn Leu Gly Thr Arg Ile Ser Glu Glu Ala Val Arg Asn
        195                 200                 205

Ser Trp Asn Thr Ala Ala Ser Gly Gly Phe Phe Ala Ala Ala Ala Ala
    210                 215                 220

Pro Thr Thr Trp Tyr Thr Asp Phe Arg Ala Asp Ile Pro Arg Ile Asp
225                 230                 235                 240

Val Pro Ala Leu Ile Leu His Gly Thr Gly Asp Arg Thr Leu Pro Ile
                245                 250                 255

Glu Asn Thr Ala Arg Val Phe His Lys Ala Leu Pro Ser Ala Glu Tyr
            260                 265                 270

Val Glu Val Glu Gly Ala Pro His Gly Leu Leu Trp Thr His Ala Glu
        275                 280                 285

Glu Val Asn Thr Ala Leu Leu Ala Phe Leu Ala Lys Ala Gln Glu Ala
    290                 295                 300

Gln Lys Gln Lys Leu Leu Thr Glu Val Glu Thr Tyr Val Leu Ser Ile
305                 310                 315                 320

Ile Pro Ser Gly Pro Leu Lys Ala Glu Ile Ala Gln Arg Leu Glu Asp
                325                 330                 335

Val Phe Ala Gly Lys Asn Thr Asp Leu Glu Val Leu Met Glu Trp Leu
            340                 345                 350

Lys Thr Arg Pro Ile Leu Ser Pro Leu Thr Lys Gly Ile Leu Gly Phe
        355                 360                 365

Val Phe Thr Leu Thr Val Pro Ser Glu Arg Gly Leu Gln Arg Arg Arg
    370                 375                 380

Phe Val Gln Asn Ala Leu Asn Gly Asn Gly Asp Pro Asn Asn Met Asp
385                 390                 395                 400

Lys Ala Val Lys Leu Tyr Arg Lys Leu Lys Arg Glu Ile Thr Phe His
                405                 410                 415

Gly Ala Lys Glu Ile Ser Leu Ser Tyr Ser Ala Gly Ala Leu Ala Ser
            420                 425                 430

Cys Met Gly Leu Ile Tyr Asn Arg Met Gly Ala Val Thr Thr Glu Val
        435                 440                 445

Ala Phe Gly Leu Val Cys Ala Thr Cys Glu Gln Ile Ala Asp Ser Gln
    450                 455                 460

His Arg Ser His Arg Gln Leu Glu His His His His His His
465                 470                 475
```

<210> SEQ ID NO 10
<211> LENGTH: 474
<212> TYPE: PRT
<213> ORGANISM: Artificial Sequence
<220> FEATURE:
<223> OTHER INFORMATION: Engineered Self-Assembling Protein Nanocage
      SAPNA_10

<400> SEQUENCE: 10

-continued

```
Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Gly Arg Trp Asp Cys Ala Trp His Leu Gly Glu
    130                 135                 140

Leu Val Trp Cys Thr Trp Glu Gly Asp Asn Pro Asp Gly Ala Ala Pro
145                 150                 155                 160

Gln Glu Phe Phe Asp Gly Ile Val Ala Ala Val Lys Ala Asp Arg Tyr
                165                 170                 175

Ala Phe Tyr Thr Gly Phe Phe Asn Asp Phe Tyr Asn Leu Asp Glu Asn
            180                 185                 190

Leu Gly Thr Arg Ile Ser Glu Glu Ala Val Arg Asn Ser Trp Asn Thr
        195                 200                 205

Ala Ala Ser Gly Gly Phe Phe Ala Ala Ala Ala Ala Pro Thr Thr Trp
    210                 215                 220

Tyr Thr Asp Phe Arg Ala Asp Ile Pro Arg Ile Asp Val Pro Ala Leu
225                 230                 235                 240

Ile Leu His Gly Thr Gly Asp Arg Thr Leu Pro Ile Glu Asn Thr Ala
                245                 250                 255

Arg Val Phe His Lys Ala Leu Pro Ser Ala Glu Tyr Val Glu Val Glu
            260                 265                 270

Gly Ala Pro His Gly Leu Leu Trp Thr His Ala Glu Glu Val Asn Thr
        275                 280                 285

Ala Leu Leu Ala Phe Leu Ala Lys Ala Gln Glu Ala Gln Lys Gln Lys
    290                 295                 300

Leu Leu Thr Glu Val Glu Thr Tyr Val Leu Ser Ile Ile Pro Ser Gly
305                 310                 315                 320

Pro Leu Lys Ala Glu Ile Ala Gln Arg Leu Glu Asp Val Phe Ala Gly
                325                 330                 335

Lys Asn Thr Asp Leu Glu Val Leu Met Glu Trp Leu Lys Thr Arg Pro
            340                 345                 350

Ile Leu Ser Pro Leu Thr Lys Gly Ile Leu Gly Phe Val Phe Thr Leu
        355                 360                 365

Thr Val Pro Ser Glu Arg Gly Leu Gln Arg Arg Arg Phe Val Gln Asn
    370                 375                 380

Ala Leu Asn Gly Asn Gly Asp Pro Asn Asn Met Asp Lys Ala Val Lys
385                 390                 395                 400

Leu Tyr Arg Lys Leu Lys Arg Glu Ile Thr Phe His Gly Ala Lys Glu
                405                 410                 415

Ile Ser Leu Ser Tyr Ser Ala Gly Ala Leu Ala Ser Cys Met Gly Leu
```

```
            420                 425                 430

Ile Tyr Asn Arg Met Gly Ala Val Thr Thr Glu Val Ala Phe Gly Leu
        435                 440                 445

Val Cys Ala Thr Cys Glu Gln Ile Ala Asp Ser Gln His Arg Ser His
    450                 455                 460

Arg Gln Leu Glu His His His His His His
465                 470


<210> SEQ ID NO 11
<211> LENGTH: 480
<212> TYPE: PRT
<213> ORGANISM: Artificial Sequence
<220> FEATURE:
<223> OTHER INFORMATION: Engineered Self-Assembling Protein Nanocage
      SAPNA_11

<400> SEQUENCE: 11

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Gly Gly Gly Gly Arg Trp Asp Cys Ala Trp His
    130                 135                 140

Leu Gly Glu Leu Val Trp Cys Thr Trp Glu Gly Gly Gly Gly Asp Asn
145                 150                 155                 160

Pro Asp Gly Ala Ala Pro Gln Glu Phe Phe Asp Gly Ile Val Ala Ala
                165                 170                 175

Val Lys Ala Asp Arg Tyr Ala Phe Tyr Thr Gly Phe Phe Asn Asp Phe
            180                 185                 190

Tyr Asn Leu Asp Glu Asn Leu Gly Thr Arg Ile Ser Glu Glu Ala Val
        195                 200                 205

Arg Asn Ser Trp Asn Thr Ala Ala Ser Gly Gly Phe Phe Ala Ala Ala
    210                 215                 220

Ala Ala Pro Thr Thr Trp Tyr Thr Asp Phe Arg Ala Asp Ile Pro Arg
225                 230                 235                 240

Ile Asp Val Pro Ala Leu Ile Leu His Gly Thr Gly Asp Arg Thr Leu
                245                 250                 255

Pro Ile Glu Asn Thr Ala Arg Val Phe His Lys Ala Leu Pro Ser Ala
            260                 265                 270

Glu Tyr Val Glu Val Glu Gly Ala Pro His Gly Leu Leu Trp Thr His
        275                 280                 285

Ala Glu Glu Val Asn Thr Ala Leu Leu Ala Phe Leu Ala Lys Ala Gln
    290                 295                 300
```

-continued

Glu Ala Gln Lys Gln Lys Leu Leu Thr Glu Val Glu Thr Tyr Val Leu
305 310 315 320

Ser Ile Ile Pro Ser Gly Pro Leu Lys Ala Glu Ile Ala Gln Arg Leu
325 330 335

Glu Asp Val Phe Ala Gly Lys Asn Thr Asp Leu Glu Val Leu Met Glu
340 345 350

Trp Leu Lys Thr Arg Pro Ile Leu Ser Pro Leu Thr Lys Gly Ile Leu
355 360 365

Gly Phe Val Phe Thr Leu Thr Val Pro Ser Glu Arg Gly Leu Gln Arg
370 375 380

Arg Arg Phe Val Gln Asn Ala Leu Asn Gly Asn Gly Asp Pro Asn Asn
385 390 395 400

Met Asp Lys Ala Val Lys Leu Tyr Arg Lys Leu Lys Arg Glu Ile Thr
405 410 415

Phe His Gly Ala Lys Glu Ile Ser Leu Ser Tyr Ser Ala Gly Ala Leu
420 425 430

Ala Ser Cys Met Gly Leu Ile Tyr Asn Arg Met Gly Ala Val Thr Thr
435 440 445

Glu Val Ala Phe Gly Leu Val Cys Ala Thr Cys Glu Gln Ile Ala Asp
450 455 460

Ser Gln His Arg Ser His Arg Gln Leu Glu His His His His His His
465 470 475 480

<210> SEQ ID NO 12
<211> LENGTH: 480
<212> TYPE: PRT
<213> ORGANISM: Artificial Sequence
<220> FEATURE:
<223> OTHER INFORMATION: Engineered Self-Assembling Protein Nanocage SAPNA_12

<400> SEQUENCE: 12

Met Pro Phe Ile Thr Val Gly Gln Glu Asn Ser Thr Ser Ile Asp Leu
1 5 10 15

Tyr Tyr Glu Asp His Gly Thr Gly Thr Pro Val Val Leu Ile His Gly
20 25 30

Phe Pro Leu Ser Gly His Ser Trp Glu Arg Gln Ser Ala Ala Leu Leu
35 40 45

Asp Ala Gly Tyr Arg Val Ile Thr Tyr Asp Arg Arg Gly Phe Gly Gln
50 55 60

Ser Ser Gln Pro Thr Thr Gly Tyr Asp Tyr Asp Thr Phe Ala Ala Asp
65 70 75 80

Leu Asn Thr Val Leu Glu Thr Leu Asp Leu Gln Asp Ala Val Leu Val
85 90 95

Gly Phe Ser Met Gly Thr Gly Glu Val Ala Arg Tyr Val Ser Ser Tyr
100 105 110

Gly Thr Ala Arg Ile Ala Ala Val Ala Phe Leu Ala Ser Leu Glu Pro
115 120 125

Phe Leu Leu Lys Thr Gly Gly Gly Gly Arg Trp Asp Ala Ala Trp His
130 135 140

Leu Gly Glu Leu Val Trp Ala Thr Trp Glu Gly Gly Gly Gly Asp Asn
145 150 155 160

Pro Asp Gly Ala Ala Pro Gln Glu Phe Phe Asp Gly Ile Val Ala Ala
165 170 175

Val Lys Ala Asp Arg Tyr Ala Phe Tyr Thr Gly Phe Phe Asn Asp Phe
180 185 190

-continued

```
Tyr Asn Leu Asp Glu Asn Leu Gly Thr Arg Ile Ser Glu Glu Ala Val
        195                 200                 205

Arg Asn Ser Trp Asn Thr Ala Ala Ser Gly Gly Phe Phe Ala Ala Ala
    210                 215                 220

Ala Ala Pro Thr Thr Trp Tyr Thr Asp Phe Arg Ala Asp Ile Pro Arg
225                 230                 235                 240

Ile Asp Val Pro Ala Leu Ile Leu His Gly Thr Gly Asp Arg Thr Leu
                245                 250                 255

Pro Ile Glu Asn Thr Ala Arg Val Phe His Lys Ala Leu Pro Ser Ala
            260                 265                 270

Glu Tyr Val Glu Val Glu Gly Ala Pro His Gly Leu Leu Trp Thr His
        275                 280                 285

Ala Glu Glu Val Asn Thr Ala Leu Leu Ala Phe Leu Ala Lys Ala Gln
    290                 295                 300

Glu Ala Gln Lys Gln Lys Leu Leu Thr Glu Val Glu Thr Tyr Val Leu
305                 310                 315                 320

Ser Ile Ile Pro Ser Gly Pro Leu Lys Ala Glu Ile Ala Gln Arg Leu
                325                 330                 335

Glu Asp Val Phe Ala Gly Lys Asn Thr Asp Leu Glu Val Leu Met Glu
            340                 345                 350

Trp Leu Lys Thr Arg Pro Ile Leu Ser Pro Leu Thr Lys Gly Ile Leu
        355                 360                 365

Gly Phe Val Phe Thr Leu Thr Val Pro Ser Glu Arg Gly Leu Gln Arg
    370                 375                 380

Arg Arg Phe Val Gln Asn Ala Leu Asn Gly Asn Gly Asp Pro Asn Asn
385                 390                 395                 400

Met Asp Lys Ala Val Lys Leu Tyr Arg Lys Leu Lys Arg Glu Ile Thr
                405                 410                 415

Phe His Gly Ala Lys Glu Ile Ser Leu Ser Tyr Ser Ala Gly Ala Leu
            420                 425                 430

Ala Ser Cys Met Gly Leu Ile Tyr Asn Arg Met Gly Ala Val Thr Thr
        435                 440                 445

Glu Val Ala Phe Gly Leu Val Cys Ala Thr Cys Glu Gln Ile Ala Asp
    450                 455                 460

Ser Gln His Arg Ser His Arg Gln Leu Glu His His His His His His
465                 470                 475                 480


<210> SEQ ID NO 13
<211> LENGTH: 480
<212> TYPE: PRT
<213> ORGANISM: Artificial Sequence
<220> FEATURE:
<223> OTHER INFORMATION: Engineered Self-Assembling Protein Nanocage
      SAPNA_13

<400> SEQUENCE: 13

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
```

```
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Gly Gly Gly Ser Gly Ala Asp Cys Ala Trp His
    130                 135                 140

Leu Gly Glu Leu Val Trp Cys Thr Ala Gly Ser Gly Gly Gly Asp Asn
145                 150                 155                 160

Pro Asp Gly Ala Ala Pro Gln Glu Phe Phe Asp Gly Ile Val Ala Ala
                165                 170                 175

Val Lys Ala Asp Arg Tyr Ala Phe Tyr Thr Gly Phe Phe Asn Asp Phe
            180                 185                 190

Tyr Asn Leu Asp Glu Asn Leu Gly Thr Arg Ile Ser Glu Glu Ala Val
        195                 200                 205

Arg Asn Ser Trp Asn Thr Ala Ala Ser Gly Gly Phe Phe Ala Ala Ala
    210                 215                 220

Ala Ala Pro Thr Thr Trp Tyr Thr Asp Phe Arg Ala Asp Ile Pro Arg
225                 230                 235                 240

Ile Asp Val Pro Ala Leu Ile Leu His Gly Thr Gly Asp Arg Thr Leu
                245                 250                 255

Pro Ile Glu Asn Thr Ala Arg Val Phe His Lys Ala Leu Pro Ser Ala
            260                 265                 270

Glu Tyr Val Glu Val Glu Gly Ala Pro His Gly Leu Leu Trp Thr His
        275                 280                 285

Ala Glu Glu Val Asn Thr Ala Leu Leu Ala Phe Leu Ala Lys Ala Gln
    290                 295                 300

Glu Ala Gln Lys Gln Lys Leu Leu Thr Glu Val Glu Thr Tyr Val Leu
305                 310                 315                 320

Ser Ile Ile Pro Ser Gly Pro Leu Lys Ala Glu Ile Ala Gln Arg Leu
                325                 330                 335

Glu Asp Val Phe Ala Gly Lys Asn Thr Asp Leu Glu Val Leu Met Glu
            340                 345                 350

Trp Leu Lys Thr Arg Pro Ile Leu Ser Pro Leu Thr Lys Gly Ile Leu
        355                 360                 365

Gly Phe Val Phe Thr Leu Thr Val Pro Ser Glu Arg Gly Leu Gln Arg
    370                 375                 380

Arg Arg Phe Val Gln Asn Ala Leu Asn Gly Asn Gly Asp Pro Asn Asn
385                 390                 395                 400

Met Asp Lys Ala Val Lys Leu Tyr Arg Lys Leu Lys Arg Glu Ile Thr
                405                 410                 415

Phe His Gly Ala Lys Glu Ile Ser Leu Ser Tyr Ser Ala Gly Ala Leu
            420                 425                 430

Ala Ser Cys Met Gly Leu Ile Tyr Asn Arg Met Gly Ala Val Thr Thr
        435                 440                 445

Glu Val Ala Phe Gly Leu Val Cys Ala Thr Cys Glu Gln Ile Ala Asp
    450                 455                 460

Ser Gln His Arg Ser His Arg Gln Leu Glu His His His His His His
465                 470                 475                 480
```

<210> SEQ ID NO 14

-continued

<211> LENGTH: 480
<212> TYPE: PRT
<213> ORGANISM: Artificial Sequence
<220> FEATURE:
<223> OTHER INFORMATION: Engineered Self-Assembling Protein Nanocage
SAPNA_14

<400> SEQUENCE: 14

Met Pro Phe Ile Thr Val Gly Gln Glu Asn Ser Thr Ser Ile Asp Leu
1 5 10 15

Tyr Tyr Glu Asp His Gly Thr Gly Thr Pro Val Val Leu Ile His Gly
20 25 30

Phe Pro Leu Ser Gly His Ser Trp Glu Arg Gln Ser Ala Ala Leu Leu
35 40 45

Asp Ala Gly Tyr Arg Val Ile Thr Tyr Asp Arg Arg Gly Phe Gly Gln
50 55 60

Ser Ser Gln Pro Thr Thr Gly Tyr Asp Tyr Asp Thr Phe Ala Ala Asp
65 70 75 80

Leu Asn Thr Val Leu Glu Thr Leu Asp Leu Gln Asp Ala Val Leu Val
85 90 95

Gly Phe Ser Met Gly Thr Gly Glu Val Ala Arg Tyr Val Ser Ser Tyr
100 105 110

Gly Thr Ala Arg Ile Ala Ala Val Ala Phe Leu Ala Ser Leu Glu Pro
115 120 125

Phe Leu Leu Lys Thr Gly Gly Gly Ser Gly Ala Asp Ala Ala Trp His
130 135 140

Leu Gly Glu Leu Val Trp Ala Thr Ala Gly Ser Gly Gly Gly Asp Asn
145 150 155 160

Pro Asp Gly Ala Ala Pro Gln Glu Phe Phe Asp Gly Ile Val Ala Ala
165 170 175

Val Lys Ala Asp Arg Tyr Ala Phe Tyr Thr Gly Phe Phe Asn Asp Phe
180 185 190

Tyr Asn Leu Asp Glu Asn Leu Gly Thr Arg Ile Ser Glu Glu Ala Val
195 200 205

Arg Asn Ser Trp Asn Thr Ala Ala Ser Gly Gly Phe Phe Ala Ala Ala
210 215 220

Ala Ala Pro Thr Thr Trp Tyr Thr Asp Phe Arg Ala Asp Ile Pro Arg
225 230 235 240

Ile Asp Val Pro Ala Leu Ile Leu His Gly Thr Gly Asp Arg Thr Leu
245 250 255

Pro Ile Glu Asn Thr Ala Arg Val Phe His Lys Ala Leu Pro Ser Ala
260 265 270

Glu Tyr Val Glu Val Glu Gly Ala Pro His Gly Leu Leu Trp Thr His
275 280 285

Ala Glu Glu Val Asn Thr Ala Leu Leu Ala Phe Leu Ala Lys Ala Gln
290 295 300

Glu Ala Gln Lys Gln Lys Leu Leu Thr Glu Val Glu Thr Tyr Val Leu
305 310 315 320

Ser Ile Ile Pro Ser Gly Pro Leu Lys Ala Glu Ile Ala Gln Arg Leu
325 330 335

Glu Asp Val Phe Ala Gly Lys Asn Thr Asp Leu Glu Val Leu Met Glu
340 345 350

Trp Leu Lys Thr Arg Pro Ile Leu Ser Pro Leu Thr Lys Gly Ile Leu
355 360 365

Gly Phe Val Phe Thr Leu Thr Val Pro Ser Glu Arg Gly Leu Gln Arg

-continued

```
    370                 375                 380

Arg Arg Phe Val Gln Asn Ala Leu Asn Gly Asn Gly Asp Pro Asn Asn
385                 390                 395                 400

Met Asp Lys Ala Val Lys Leu Tyr Arg Lys Leu Lys Arg Glu Ile Thr
                405                 410                 415

Phe His Gly Ala Lys Glu Ile Ser Leu Ser Tyr Ser Ala Gly Ala Leu
            420                 425                 430

Ala Ser Cys Met Gly Leu Ile Tyr Asn Arg Met Gly Ala Val Thr Thr
        435                 440                 445

Glu Val Ala Phe Gly Leu Val Cys Ala Thr Cys Glu Gln Ile Ala Asp
    450                 455                 460

Ser Gln His Arg Ser His Arg Gln Leu Glu His His His His His His
465                 470                 475                 480


<210> SEQ ID NO 15
<211> LENGTH: 481
<212> TYPE: PRT
<213> ORGANISM: Artificial Sequence
<220> FEATURE:
<223> OTHER INFORMATION: Engineered Self-Assembling Protein Nanocage
      SAPNA_15

<400> SEQUENCE: 15

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Glu
    130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Ala Pro Thr Thr Trp Tyr Thr
        195                 200                 205

Asp Phe Arg Ala Asp Ile Pro Arg Ile Asp Val Pro Ala Leu Ile Leu
    210                 215                 220

His Gly Thr Gly Asp Arg Thr Leu Pro Ile Glu Asn Thr Ala Arg Val
225                 230                 235                 240

Phe His Lys Ala Leu Pro Ser Gly Gly Gly Ser Gly Cys Asp Cys Ala
                245                 250                 255
```

```
Trp His Leu Gly Glu Leu Val Trp Cys Thr Cys Gly Ser Gly Gly Gly
            260                 265                 270

Ala Glu Tyr Val Glu Val Glu Gly Ala Pro His Gly Leu Leu Trp Thr
        275                 280                 285

His Ala Glu Glu Val Asn Thr Ala Leu Leu Ala Phe Leu Ala Lys Ala
    290                 295                 300

Gln Glu Ala Gln Lys Gln Lys Leu Leu Thr Glu Val Glu Thr Tyr Val
305                 310                 315                 320

Leu Ser Ile Ile Pro Ser Gly Pro Leu Lys Ala Glu Ile Ala Gln Arg
                325                 330                 335

Leu Glu Asp Val Phe Ala Gly Lys Asn Thr Asp Leu Glu Val Leu Met
            340                 345                 350

Glu Trp Leu Lys Thr Arg Pro Ile Leu Ser Pro Leu Thr Lys Gly Ile
        355                 360                 365

Leu Gly Phe Val Phe Thr Leu Thr Val Pro Ser Glu Arg Gly Leu Gln
    370                 375                 380

Arg Arg Arg Phe Val Gln Asn Ala Leu Asn Gly Asn Gly Asp Pro Asn
385                 390                 395                 400

Asn Met Asp Lys Ala Val Lys Leu Tyr Arg Lys Leu Lys Arg Glu Ile
                405                 410                 415

Thr Phe His Gly Ala Lys Glu Ile Ser Leu Ser Tyr Ser Ala Gly Ala
            420                 425                 430

Leu Ala Ser Cys Met Gly Leu Ile Tyr Asn Arg Met Gly Ala Val Thr
        435                 440                 445

Thr Glu Val Ala Phe Gly Leu Val Cys Ala Thr Cys Glu Gln Ile Ala
    450                 455                 460

Asp Ser Gln His Arg Ser His Arg Gln Leu Glu His His His His His
465                 470                 475                 480

His


<210> SEQ ID NO 16
<211> LENGTH: 480
<212> TYPE: PRT
<213> ORGANISM: Artificial Sequence
<220> FEATURE:
<223> OTHER INFORMATION: Engineered Self-Assembling Protein Nanocage
      SAPNA_16

<400> SEQUENCE: 16

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125
```

-continued

Phe Leu Leu Lys Thr Asp Asp Asn Pro Asp Gly Ala Ala Pro Gln Glu
    130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Ala Pro Thr Thr Trp Tyr Thr
        195                 200                 205

Asp Phe Arg Ala Asp Ile Pro Arg Ile Gly Gly Gly Ser Gly Cys Asp
    210                 215                 220

Cys Ala Trp His Leu Gly Glu Leu Val Trp Cys Thr Cys Gly Ser Gly
225                 230                 235                 240

Gly Gly Val Pro Ala Leu Ile Leu His Gly Thr Gly Asp Arg Thr Leu
                245                 250                 255

Pro Ile Glu Asn Thr Ala Arg Val Phe His Lys Ala Leu Pro Ser Ala
            260                 265                 270

Glu Tyr Val Glu Val Glu Gly Ala Pro His Gly Leu Leu Trp Thr His
        275                 280                 285

Ala Glu Glu Val Asn Thr Ala Leu Leu Ala Phe Leu Ala Lys Ala Gln
    290                 295                 300

Glu Ala Gln Lys Gln Lys Leu Leu Thr Glu Val Glu Thr Tyr Val Leu
305                 310                 315                 320

Ser Ile Ile Pro Ser Gly Pro Leu Lys Ala Glu Ile Ala Gln Arg Leu
                325                 330                 335

Glu Asp Val Phe Ala Gly Lys Asn Thr Asp Leu Glu Val Leu Met Glu
            340                 345                 350

Trp Leu Lys Thr Arg Pro Ile Leu Ser Pro Leu Thr Lys Gly Ile Leu
        355                 360                 365

Gly Phe Val Phe Thr Leu Thr Val Pro Ser Glu Arg Gly Leu Gln Arg
    370                 375                 380

Arg Arg Phe Val Gln Asn Ala Leu Asn Gly Asn Gly Asp Pro Asn Asn
385                 390                 395                 400

Met Asp Lys Ala Val Lys Leu Tyr Arg Lys Leu Lys Arg Glu Ile Thr
                405                 410                 415

Phe His Gly Ala Lys Glu Ile Ser Leu Ser Tyr Ser Ala Gly Ala Leu
            420                 425                 430

Ala Ser Cys Met Gly Leu Ile Tyr Asn Arg Met Gly Ala Val Thr Thr
        435                 440                 445

Glu Val Ala Phe Gly Leu Val Cys Ala Thr Cys Glu Gln Ile Ala Asp
    450                 455                 460

Ser Gln His Arg Ser His Arg Gln Leu Glu His His His His His His
465                 470                 475                 480

<210> SEQ ID NO 17
<211> LENGTH: 475
<212> TYPE: PRT
<213> ORGANISM: Artificial Sequence
<220> FEATURE:
<223> OTHER INFORMATION: Engineered Self-Assembling Protein Nanocage
      SAPNA_17

<400> SEQUENCE: 17

Met Pro Phe Ile Thr Val Gly Gln Glu Asn Ser Thr Ser Ile Asp Leu
1               5                   10                  15

-continued

```
Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Glu
    130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Gly Gly Gly Ser Gly
                165                 170                 175

Cys Asp Cys Ala Trp His Leu Gly Glu Leu Val Trp Cys Thr Cys Gly
            180                 185                 190

Ser Gly Gly Gly Arg Ile Ser Glu Glu Ala Val Arg Asn Ser Trp Asn
        195                 200                 205

Thr Ala Ala Ser Gly Gly Phe Phe Ala Ala Ala Ala Ala Pro Thr Thr
    210                 215                 220

Trp Tyr Thr Asp Phe Arg Ala Asp Ile Pro Arg Ile Asp Val Pro Ala
225                 230                 235                 240

Leu Ile Leu His Gly Thr Gly Asp Arg Thr Leu Pro Ile Glu Asn Thr
                245                 250                 255

Ala Arg Val Phe His Lys Ala Leu Pro Ser Ala Glu Tyr Val Glu Val
            260                 265                 270

Glu Gly Ala Pro His Gly Leu Leu Trp Thr His Ala Glu Glu Val Asn
        275                 280                 285

Thr Ala Leu Leu Ala Phe Leu Ala Lys Ala Gln Glu Ala Gln Lys Gln
    290                 295                 300

Lys Leu Leu Thr Glu Val Glu Thr Tyr Val Leu Ser Ile Ile Pro Ser
305                 310                 315                 320

Gly Pro Leu Lys Ala Glu Ile Ala Gln Arg Leu Glu Asp Val Phe Ala
                325                 330                 335

Gly Lys Asn Thr Asp Leu Glu Val Leu Met Glu Trp Leu Lys Thr Arg
            340                 345                 350

Pro Ile Leu Ser Pro Leu Thr Lys Gly Ile Leu Gly Phe Val Phe Thr
        355                 360                 365

Leu Thr Val Pro Ser Glu Arg Gly Leu Gln Arg Arg Arg Phe Val Gln
    370                 375                 380

Asn Ala Leu Asn Gly Asn Gly Asp Pro Asn Asn Met Asp Lys Ala Val
385                 390                 395                 400

Lys Leu Tyr Arg Lys Leu Lys Arg Glu Ile Thr Phe His Gly Ala Lys
                405                 410                 415

Glu Ile Ser Leu Ser Tyr Ser Ala Gly Ala Leu Ala Ser Cys Met Gly
            420                 425                 430
```

-continued

Leu Ile Tyr Asn Arg Met Gly Ala Val Thr Thr Glu Val Ala Phe Gly
435 440 445

Leu Val Cys Ala Thr Cys Glu Gln Ile Ala Asp Ser Gln His Arg Ser
450 455 460

His Arg Gln Leu Glu His His His His His His
465 470 475

<210> SEQ ID NO 18
<211> LENGTH: 478
<212> TYPE: PRT
<213> ORGANISM: Artificial Sequence
<220> FEATURE:
<223> OTHER INFORMATION: Engineered Self-Assembling Protein Nanocage SAPNA_18

<400> SEQUENCE: 18

Met Pro Phe Ile Thr Val Gly Gln Glu Asn Ser Thr Ser Ile Asp Leu
1 5 10 15

Tyr Tyr Glu Asp His Gly Thr Gly Thr Pro Val Val Leu Ile His Gly
20 25 30

Phe Pro Leu Ser Gly His Ser Trp Glu Arg Gln Ser Ala Ala Leu Leu
35 40 45

Asp Ala Gly Tyr Arg Val Ile Thr Tyr Asp Arg Arg Gly Phe Gly Gln
50 55 60

Ser Ser Gln Pro Thr Thr Gly Tyr Asp Tyr Asp Thr Phe Ala Ala Asp
65 70 75 80

Leu Asn Thr Val Leu Glu Thr Leu Asp Leu Gln Asp Ala Val Leu Val
85 90 95

Gly Phe Ser Met Gly Thr Gly Glu Val Ala Arg Tyr Val Ser Ser Tyr
100 105 110

Gly Thr Ala Arg Ile Ala Ala Val Ala Phe Leu Ala Ser Leu Glu Pro
115 120 125

Phe Leu Leu Lys Thr Asp Asp Asn Pro Asp Gly Ala Ala Pro Gln Glu
130 135 140

Phe Phe Asp Gly Ile Val Ala Ala Val Lys Ala Asp Arg Tyr Ala Phe
145 150 155 160

Tyr Thr Gly Phe Phe Asn Asp Phe Tyr Asn Leu Asp Glu Asn Leu Gly
165 170 175

Thr Arg Ile Ser Glu Glu Ala Val Arg Asn Ser Trp Asn Thr Ala Ala
180 185 190

Ser Gly Gly Phe Phe Ala Ala Ala Ala Ala Pro Thr Thr Trp Tyr Thr
195 200 205

Asp Phe Arg Ala Asp Ile Pro Arg Ile Asp Val Pro Ala Leu Ile Leu
210 215 220

His Gly Thr Gly Gly Gly Ser Gly Cys Asp Cys Ala Trp His Leu Gly
225 230 235 240

Glu Leu Val Trp Cys Thr Cys Gly Ser Gly Gly Gly Thr Leu Pro Ile
245 250 255

Glu Asn Thr Ala Arg Val Phe His Lys Ala Leu Pro Ser Ala Glu Tyr
260 265 270

Val Glu Val Glu Gly Ala Pro His Gly Leu Leu Trp Thr His Ala Glu
275 280 285

Glu Val Asn Thr Ala Leu Leu Ala Phe Leu Ala Lys Ala Gln Glu Ala
290 295 300

Gln Lys Gln Lys Leu Leu Thr Glu Val Glu Thr Tyr Val Leu Ser Ile
305 310 315 320

```
Ile Pro Ser Gly Pro Leu Lys Ala Glu Ile Ala Gln Arg Leu Glu Asp
                325                 330                 335

Val Phe Ala Gly Lys Asn Thr Asp Leu Glu Val Leu Met Glu Trp Leu
            340                 345                 350

Lys Thr Arg Pro Ile Leu Ser Pro Leu Thr Lys Gly Ile Leu Gly Phe
        355                 360                 365

Val Phe Thr Leu Thr Val Pro Ser Glu Arg Gly Leu Gln Arg Arg Arg
    370                 375                 380

Phe Val Gln Asn Ala Leu Asn Gly Asn Gly Asp Pro Asn Asn Met Asp
385                 390                 395                 400

Lys Ala Val Lys Leu Tyr Arg Lys Leu Lys Arg Glu Ile Thr Phe His
                405                 410                 415

Gly Ala Lys Glu Ile Ser Leu Ser Tyr Ser Ala Gly Ala Leu Ala Ser
            420                 425                 430

Cys Met Gly Leu Ile Tyr Asn Arg Met Gly Ala Val Thr Thr Glu Val
        435                 440                 445

Ala Phe Gly Leu Val Cys Ala Thr Cys Glu Gln Ile Ala Asp Ser Gln
    450                 455                 460

His Arg Ser His Arg Gln Leu Glu His His His His His His
465                 470                 475


<210> SEQ ID NO 19
<211> LENGTH: 478
<212> TYPE: PRT
<213> ORGANISM: Artificial Sequence
<220> FEATURE:
<223> OTHER INFORMATION: Engineered Self-Assembling Protein Nanocage
      SAPNA_19

<400> SEQUENCE: 19

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Gly Gly Ser Gly Cys Asp Cys Ala Trp His Leu Gly Glu Leu Val
        115                 120                 125

Trp Cys Thr Cys Gly Ser Gly Gly Gly Arg Ile Ala Ala Val Ala Phe
    130                 135                 140

Leu Ala Ser Leu Glu Pro Phe Leu Leu Lys Thr Asp Asp Asn Pro Asp
145                 150                 155                 160

Gly Ala Ala Pro Gln Glu Phe Phe Asp Gly Ile Val Ala Ala Val Lys
                165                 170                 175

Ala Asp Arg Tyr Ala Phe Tyr Thr Gly Phe Phe Asn Asp Phe Tyr Asn
            180                 185                 190

Leu Asp Glu Asn Leu Gly Thr Arg Ile Ser Glu Glu Ala Val Arg Asn
```

-continued

```
        195                 200                 205

Ser Trp Asn Thr Ala Ala Ser Gly Gly Phe Phe Ala Ala Ala Ala Ala
    210                 215                 220

Pro Thr Thr Trp Tyr Thr Asp Phe Arg Ala Asp Ile Pro Arg Ile Asp
225                 230                 235                 240

Val Pro Ala Leu Ile Leu His Gly Thr Gly Asp Arg Thr Leu Pro Ile
                245                 250                 255

Glu Asn Thr Ala Arg Val Phe His Lys Ala Leu Pro Ser Ala Glu Tyr
            260                 265                 270

Val Glu Val Glu Gly Ala Pro His Gly Leu Leu Trp Thr His Ala Glu
        275                 280                 285

Glu Val Asn Thr Ala Leu Leu Ala Phe Leu Ala Lys Ala Gln Glu Ala
    290                 295                 300

Gln Lys Gln Lys Leu Leu Thr Glu Val Glu Thr Tyr Val Leu Ser Ile
305                 310                 315                 320

Ile Pro Ser Gly Pro Leu Lys Ala Glu Ile Ala Gln Arg Leu Glu Asp
                325                 330                 335

Val Phe Ala Gly Lys Asn Thr Asp Leu Glu Val Leu Met Glu Trp Leu
            340                 345                 350

Lys Thr Arg Pro Ile Leu Ser Pro Leu Thr Lys Gly Ile Leu Gly Phe
        355                 360                 365

Val Phe Thr Leu Thr Val Pro Ser Glu Arg Gly Leu Gln Arg Arg Arg
    370                 375                 380

Phe Val Gln Asn Ala Leu Asn Gly Asn Gly Asp Pro Asn Asn Met Asp
385                 390                 395                 400

Lys Ala Val Lys Leu Tyr Arg Lys Leu Lys Arg Glu Ile Thr Phe His
                405                 410                 415

Gly Ala Lys Glu Ile Ser Leu Ser Tyr Ser Ala Gly Ala Leu Ala Ser
            420                 425                 430

Cys Met Gly Leu Ile Tyr Asn Arg Met Gly Ala Val Thr Thr Glu Val
        435                 440                 445

Ala Phe Gly Leu Val Cys Ala Thr Cys Glu Gln Ile Ala Asp Ser Gln
    450                 455                 460

His Arg Ser His Arg Gln Leu Glu His His His His His His
465                 470                 475


<210> SEQ ID NO 20
<211> LENGTH: 478
<212> TYPE: PRT
<213> ORGANISM: Artificial Sequence
<220> FEATURE:
<223> OTHER INFORMATION: Engineered Self-Assembling Protein Nanocage
      SAPNA_20

<400> SEQUENCE: 20

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80
```

-continued

```
Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Glu
    130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Ala Pro Thr Thr Trp Tyr Thr
        195                 200                 205

Asp Phe Arg Ala Asp Ile Pro Arg Ile Asp Val Pro Ala Leu Ile Leu
    210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Glu Gly Ala
                245                 250                 255

Pro His Gly Leu Leu Trp Thr His Ala Glu Glu Val Asn Thr Ala Leu
            260                 265                 270

Leu Ala Phe Leu Ala Lys Ala Gln Glu Ala Gln Lys Gln Lys Leu Leu
        275                 280                 285

Thr Glu Val Glu Thr Tyr Val Leu Ser Ile Ile Pro Ser Gly Pro Leu
    290                 295                 300

Lys Ala Glu Ile Ala Gln Arg Leu Glu Asp Val Phe Ala Gly Gly Gly
305                 310                 315                 320

Gly Ser Gly Cys Asp Cys Ala Trp His Leu Gly Glu Leu Val Trp Cys
                325                 330                 335

Thr Cys Gly Ser Gly Gly Gly Asp Leu Glu Val Leu Met Glu Trp Leu
            340                 345                 350

Lys Thr Arg Pro Ile Leu Ser Pro Leu Thr Lys Gly Ile Leu Gly Phe
        355                 360                 365

Val Phe Thr Leu Thr Val Pro Ser Glu Arg Gly Leu Gln Arg Arg Arg
    370                 375                 380

Phe Val Gln Asn Ala Leu Asn Gly Asn Gly Asp Pro Asn Asn Met Asp
385                 390                 395                 400

Lys Ala Val Lys Leu Tyr Arg Lys Leu Lys Arg Glu Ile Thr Phe His
                405                 410                 415

Gly Ala Lys Glu Ile Ser Leu Ser Tyr Ser Ala Gly Ala Leu Ala Ser
            420                 425                 430

Cys Met Gly Leu Ile Tyr Asn Arg Met Gly Ala Val Thr Thr Glu Val
        435                 440                 445

Ala Phe Gly Leu Val Cys Ala Thr Cys Glu Gln Ile Ala Asp Ser Gln
    450                 455                 460

His Arg Ser His Arg Gln Leu Glu His His His His His His
465                 470                 475
```

<210> SEQ ID NO 21
<211> LENGTH: 475
<212> TYPE: PRT

-continued

<213> ORGANISM: Artificial Sequence
<220> FEATURE:
<223> OTHER INFORMATION: Engineered Self-Assembling Protein Nanocage
SAPNA_21

<400> SEQUENCE: 21

Met Pro Phe Ile Thr Val Gly Gln Glu Asn Ser Thr Ser Ile Asp Leu
1 5 10 15

Tyr Tyr Glu Asp His Gly Thr Gly Thr Pro Val Val Leu Ile His Gly
20 25 30

Phe Pro Leu Ser Gly His Ser Trp Glu Arg Gln Ser Ala Ala Leu Leu
35 40 45

Asp Ala Gly Tyr Arg Val Ile Thr Tyr Asp Arg Arg Gly Phe Gly Gln
50 55 60

Ser Ser Gln Pro Thr Thr Gly Tyr Asp Tyr Asp Thr Phe Ala Ala Asp
65 70 75 80

Leu Asn Thr Val Leu Glu Thr Leu Asp Leu Gln Asp Ala Val Leu Val
85 90 95

Gly Phe Ser Met Gly Thr Gly Glu Val Ala Arg Tyr Val Ser Ser Tyr
100 105 110

Gly Thr Ala Arg Ile Ala Ala Val Ala Phe Leu Ala Ser Leu Glu Pro
115 120 125

Phe Leu Leu Lys Thr Asp Asp Asn Pro Asp Gly Ala Ala Pro Gln Glu
130 135 140

Phe Phe Asp Gly Ile Val Ala Ala Val Lys Ala Asp Arg Tyr Ala Phe
145 150 155 160

Tyr Thr Gly Phe Phe Asn Asp Phe Tyr Asn Leu Asp Glu Asn Leu Gly
165 170 175

Thr Arg Ile Ser Glu Glu Ala Val Arg Asn Ser Trp Asn Thr Ala Ala
180 185 190

Ser Gly Gly Phe Phe Ala Ala Ala Ala Ala Pro Thr Thr Trp Tyr Thr
195 200 205

Asp Phe Arg Ala Asp Ile Pro Arg Ile Asp Val Pro Ala Leu Ile Leu
210 215 220

His Gly Thr Gly Asp Arg Thr Leu Pro Ile Glu Asn Thr Ala Arg Val
225 230 235 240

Phe His Lys Ala Leu Pro Ser Ala Glu Tyr Val Glu Val Glu Gly Ala
245 250 255

Pro His Gly Leu Leu Trp Thr His Ala Glu Glu Val Asn Thr Ala Leu
260 265 270

Leu Ala Phe Leu Ala Lys Ala Gln Glu Ala Gln Lys Gln Lys Leu Leu
275 280 285

Thr Glu Val Glu Thr Tyr Val Leu Ser Ile Ile Pro Ser Gly Pro Leu
290 295 300

Lys Ala Glu Ile Ala Gln Arg Leu Glu Asp Val Phe Ala Gly Lys Asn
305 310 315 320

Thr Asp Leu Glu Val Leu Met Glu Trp Leu Lys Thr Arg Pro Ile Leu
325 330 335

Ser Pro Leu Thr Lys Gly Ile Leu Gly Phe Val Phe Thr Leu Thr Val
340 345 350

Pro Ser Glu Arg Gly Leu Gln Arg Arg Arg Phe Val Gln Asn Ala Leu
355 360 365

Asn Gly Asn Gly Asp Pro Asn Asn Met Asp Lys Ala Val Lys Leu Tyr
370 375 380

-continued

```
Arg Lys Leu Lys Arg Glu Ile Thr Phe His Gly Ala Lys Glu Ile Ser
385                 390                 395                 400

Leu Ser Tyr Ser Ala Gly Ala Leu Ala Ser Cys Met Gly Leu Ile Tyr
                405                 410                 415

Asn Arg Met Gly Ala Val Thr Thr Glu Val Ala Phe Gly Leu Val Cys
            420                 425                 430

Ala Thr Cys Glu Gln Ile Ala Asp Ser Gln Gly Gly Gly Ser Gly Cys
        435                 440                 445

Asp Cys Ala Trp His Leu Gly Glu Leu Val Trp Cys Thr Cys Gly Ser
    450                 455                 460

Gly Gly Gly Leu Glu His His His His His His
465                 470                 475


<210> SEQ ID NO 22
<211> LENGTH: 478
<212> TYPE: PRT
<213> ORGANISM: Artificial Sequence
<220> FEATURE:
<223> OTHER INFORMATION: Engineered Self-Assembling Protein Nanocage
      SAPNA_22

<400> SEQUENCE: 22

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Glu
    130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Ala Pro Thr Thr Trp Tyr Thr
        195                 200                 205

Asp Phe Arg Ala Asp Ile Pro Arg Ile Asp Val Pro Ala Leu Ile Leu
    210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Glu Gly Ala
                245                 250                 255

Pro His Gly Leu Leu Trp Thr His Ala Glu Glu Val Asn Thr Ala Leu
            260                 265                 270
```

-continued

Leu Ala Phe Leu Ala Lys Ala Gln Glu Ala Gln Lys Gln Lys Leu Leu
275 280 285

Thr Glu Val Glu Thr Tyr Val Leu Ser Ile Ile Pro Ser Gly Pro Leu
290 295 300

Lys Ala Glu Ile Ala Gln Arg Leu Glu Asp Val Phe Ala Gly Gly Gly
305 310 315 320

Arg Trp Gly Cys Asp Cys Ala Trp His Leu Gly Glu Leu Val Trp Cys
325 330 335

Thr Cys Gly Trp Glu Gly Gly Asp Leu Glu Val Leu Met Glu Trp Leu
340 345 350

Lys Thr Arg Pro Ile Leu Ser Pro Leu Thr Lys Gly Ile Leu Gly Phe
355 360 365

Val Phe Thr Leu Thr Val Pro Ser Glu Arg Gly Leu Gln Arg Arg Arg
370 375 380

Phe Val Gln Asn Ala Leu Asn Gly Asn Gly Asp Pro Asn Asn Met Asp
385 390 395 400

Lys Ala Val Lys Leu Tyr Arg Lys Leu Lys Arg Glu Ile Thr Phe His
405 410 415

Gly Ala Lys Glu Ile Ser Leu Ser Tyr Ser Ala Gly Ala Leu Ala Ser
420 425 430

Cys Met Gly Leu Ile Tyr Asn Arg Met Gly Ala Val Thr Thr Glu Val
435 440 445

Ala Phe Gly Leu Val Cys Ala Thr Cys Glu Gln Ile Ala Asp Ser Gln
450 455 460

His Arg Ser His Arg Gln Leu Glu His His His His His His
465 470 475

<210> SEQ ID NO 23
<211> LENGTH: 478
<212> TYPE: PRT
<213> ORGANISM: Artificial Sequence
<220> FEATURE:
<223> OTHER INFORMATION: Engineered Self-Assembling Protein Nanocage SAPNA_23

<400> SEQUENCE: 23

Met Pro Phe Ile Thr Val Gly Gln Glu Asn Ser Thr Ser Ile Asp Leu
1 5 10 15

Tyr Tyr Glu Asp His Gly Thr Gly Thr Pro Val Val Leu Ile His Gly
20 25 30

Phe Pro Leu Ser Gly His Ser Trp Glu Arg Gln Ser Ala Ala Leu Leu
35 40 45

Asp Ala Gly Tyr Arg Val Ile Thr Tyr Asp Arg Arg Gly Phe Gly Gln
50 55 60

Ser Ser Gln Pro Thr Thr Gly Tyr Asp Tyr Asp Thr Phe Ala Ala Asp
65 70 75 80

Leu Asn Thr Val Leu Glu Thr Leu Asp Leu Gln Asp Ala Val Leu Val
85 90 95

Gly Phe Ser Met Gly Thr Gly Glu Val Ala Arg Tyr Val Ser Ser Tyr
100 105 110

Gly Thr Ala Arg Ile Ala Ala Val Ala Phe Leu Ala Ser Leu Glu Pro
115 120 125

Phe Leu Leu Lys Thr Asp Asp Asn Pro Asp Gly Ala Ala Pro Gln Glu
130 135 140

Phe Phe Asp Gly Ile Val Ala Ala Val Lys Ala Asp Arg Tyr Ala Phe

-continued

```
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Ala Pro Thr Thr Trp Tyr Thr
        195                 200                 205

Asp Phe Arg Ala Asp Ile Pro Arg Ile Asp Val Pro Ala Leu Ile Leu
    210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Glu Gly Ala
                245                 250                 255

Pro His Gly Leu Leu Trp Thr His Ala Glu Glu Val Asn Thr Ala Leu
            260                 265                 270

Leu Ala Phe Leu Ala Lys Ala Gln Glu Ala Gln Lys Gln Lys Leu Leu
        275                 280                 285

Thr Glu Val Glu Thr Tyr Val Leu Ser Ile Ile Pro Ser Gly Pro Leu
    290                 295                 300

Lys Ala Glu Ile Ala Gln Arg Leu Glu Asp Val Phe Ala Gly Arg Trp
305                 310                 315                 320

Gly Ser Gly Cys Asp Cys Ala Trp His Leu Gly Glu Leu Val Trp Cys
                325                 330                 335

Thr Cys Gly Ser Gly Trp Glu Asp Leu Glu Val Leu Met Glu Trp Leu
            340                 345                 350

Lys Thr Arg Pro Ile Leu Ser Pro Leu Thr Lys Gly Ile Leu Gly Phe
        355                 360                 365

Val Phe Thr Leu Thr Val Pro Ser Glu Arg Gly Leu Gln Arg Arg Arg
    370                 375                 380

Phe Val Gln Asn Ala Leu Asn Gly Asn Gly Asp Pro Asn Asn Met Asp
385                 390                 395                 400

Lys Ala Val Lys Leu Tyr Arg Lys Leu Lys Arg Glu Ile Thr Phe His
                405                 410                 415

Gly Ala Lys Glu Ile Ser Leu Ser Tyr Ser Ala Gly Ala Leu Ala Ser
            420                 425                 430

Cys Met Gly Leu Ile Tyr Asn Arg Met Gly Ala Val Thr Thr Glu Val
        435                 440                 445

Ala Phe Gly Leu Val Cys Ala Thr Cys Glu Gln Ile Ala Asp Ser Gln
    450                 455                 460

His Arg Ser His Arg Gln Leu Glu His His His His His His
465                 470                 475
```

<210> SEQ ID NO 24
<211> LENGTH: 474
<212> TYPE: PRT
<213> ORGANISM: Artificial Sequence
<220> FEATURE:
<223> OTHER INFORMATION: Engineered Self-Assembling Protein Nanocage SAPNA_24

<400> SEQUENCE: 24

```
Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30
```

-continued

```
Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Glu
    130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Ala Pro Thr Thr Trp Tyr Thr
        195                 200                 205

Asp Phe Arg Ala Asp Ile Pro Arg Ile Asp Val Pro Ala Leu Ile Leu
    210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Glu Gly Ala
                245                 250                 255

Pro His Gly Leu Leu Trp Thr His Ala Glu Glu Val Asn Thr Ala Leu
            260                 265                 270

Leu Ala Phe Leu Ala Lys Ala Gln Glu Ala Gln Lys Gln Lys Leu Leu
        275                 280                 285

Thr Glu Val Glu Thr Tyr Val Leu Ser Ile Ile Pro Ser Gly Pro Leu
    290                 295                 300

Lys Ala Glu Ile Ala Gln Arg Leu Glu Asp Val Phe Ala Gly Gly Gly
305                 310                 315                 320

Gly Cys Asp Cys Ala Trp His Leu Gly Glu Leu Val Trp Cys Thr Cys
                325                 330                 335

Gly Gly Gly Asp Leu Glu Val Leu Met Glu Trp Leu Lys Thr Arg Pro
            340                 345                 350

Ile Leu Ser Pro Leu Thr Lys Gly Ile Leu Gly Phe Val Phe Thr Leu
        355                 360                 365

Thr Val Pro Ser Glu Arg Gly Leu Gln Arg Arg Arg Phe Val Gln Asn
    370                 375                 380

Ala Leu Asn Gly Asn Gly Asp Pro Asn Asn Met Asp Lys Ala Val Lys
385                 390                 395                 400

Leu Tyr Arg Lys Leu Lys Arg Glu Ile Thr Phe His Gly Ala Lys Glu
                405                 410                 415

Ile Ser Leu Ser Tyr Ser Ala Gly Ala Leu Ala Ser Cys Met Gly Leu
            420                 425                 430

Ile Tyr Asn Arg Met Gly Ala Val Thr Thr Glu Val Ala Phe Gly Leu
        435                 440                 445

Val Cys Ala Thr Cys Glu Gln Ile Ala Asp Ser Gln His Arg Ser His
```

450 455 460

Arg Gln Leu Glu His His His His His His
465 470

<210> SEQ ID NO 25
<211> LENGTH: 470
<212> TYPE: PRT
<213> ORGANISM: Artificial Sequence
<220> FEATURE:
<223> OTHER INFORMATION: Engineered Self-Assembling Protein Nanocage SAPNA_25

<400> SEQUENCE: 25

Met Pro Phe Ile Thr Val Gly Gln Glu Asn Ser Thr Ser Ile Asp Leu
1 5 10 15

Tyr Tyr Glu Asp His Gly Thr Gly Thr Pro Val Val Leu Ile His Gly
20 25 30

Phe Pro Leu Ser Gly His Ser Trp Glu Arg Gln Ser Ala Ala Leu Leu
35 40 45

Asp Ala Gly Tyr Arg Val Ile Thr Tyr Asp Arg Arg Gly Phe Gly Gln
50 55 60

Ser Ser Gln Pro Thr Thr Gly Tyr Asp Tyr Asp Thr Phe Ala Ala Asp
65 70 75 80

Leu Asn Thr Val Leu Glu Thr Leu Asp Leu Gln Asp Ala Val Leu Val
85 90 95

Gly Phe Ser Met Gly Thr Gly Glu Val Ala Arg Tyr Val Ser Ser Tyr
100 105 110

Gly Thr Ala Arg Ile Ala Ala Val Ala Phe Leu Ala Ser Leu Glu Pro
115 120 125

Phe Leu Leu Lys Thr Asp Asp Asn Pro Asp Gly Ala Ala Pro Gln Glu
130 135 140

Phe Phe Asp Gly Ile Val Ala Ala Val Lys Ala Asp Arg Tyr Ala Phe
145 150 155 160

Tyr Thr Gly Phe Phe Asn Asp Phe Tyr Asn Leu Asp Glu Asn Leu Gly
165 170 175

Thr Arg Ile Ser Glu Glu Ala Val Arg Asn Ser Trp Asn Thr Ala Ala
180 185 190

Ser Gly Gly Phe Phe Ala Ala Ala Ala Ala Pro Thr Thr Trp Tyr Thr
195 200 205

Asp Phe Arg Ala Asp Ile Pro Arg Ile Asp Val Pro Ala Leu Ile Leu
210 215 220

His Gly Thr Gly Asp Arg Thr Leu Pro Ile Glu Asn Thr Ala Arg Val
225 230 235 240

Phe His Lys Ala Leu Pro Ser Ala Glu Tyr Val Glu Val Glu Gly Ala
245 250 255

Pro His Gly Leu Leu Trp Thr His Ala Glu Glu Val Asn Thr Ala Leu
260 265 270

Leu Ala Phe Leu Ala Lys Ala Gln Glu Ala Gln Lys Gln Lys Leu Leu
275 280 285

Thr Glu Val Glu Thr Tyr Val Leu Ser Ile Ile Pro Ser Gly Pro Leu
290 295 300

Lys Ala Glu Ile Ala Gln Arg Leu Glu Asp Val Phe Ala Gly Gly Cys
305 310 315 320

Asp Cys Ala Trp His Leu Gly Glu Leu Val Trp Cys Thr Cys Gly Asp
325 330 335

```
Leu Glu Val Leu Met Glu Trp Leu Lys Thr Arg Pro Ile Leu Ser Pro
            340                 345                 350

Leu Thr Lys Gly Ile Leu Gly Phe Val Phe Thr Leu Thr Val Pro Ser
        355                 360                 365

Glu Arg Gly Leu Gln Arg Arg Arg Phe Val Gln Asn Ala Leu Asn Gly
    370                 375                 380

Asn Gly Asp Pro Asn Asn Met Asp Lys Ala Val Lys Leu Tyr Arg Lys
385                 390                 395                 400

Leu Lys Arg Glu Ile Thr Phe His Gly Ala Lys Glu Ile Ser Leu Ser
                405                 410                 415

Tyr Ser Ala Gly Ala Leu Ala Ser Cys Met Gly Leu Ile Tyr Asn Arg
            420                 425                 430

Met Gly Ala Val Thr Thr Glu Val Ala Phe Gly Leu Val Cys Ala Thr
        435                 440                 445

Cys Glu Gln Ile Ala Asp Ser Gln His Arg Ser His Arg Gln Leu Glu
    450                 455                 460

His His His His His His
465                 470
```

<210> SEQ ID NO 26
<211> LENGTH: 475
<212> TYPE: PRT
<213> ORGANISM: Artificial Sequence
<220> FEATURE:
<223> OTHER INFORMATION: Engineered Self-Assembling Protein Nanocage SAPNA_26

<400> SEQUENCE: 26

```
Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Lys
    130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Ala Pro Thr Thr Trp Tyr Thr
        195                 200                 205

Asp Phe Arg Ala Asp Ile Pro Arg Ile Asp Val Pro Ala Leu Ile Leu
    210                 215                 220
```

-continued

His Gly Thr Gly Asp Arg Thr Leu Pro Ile Glu Asn Thr Ala Arg Val
225 230 235 240

Phe His Lys Ala Leu Pro Ser Ala Glu Tyr Val Glu Val Glu Gly Ala
245 250 255

Pro His Gly Leu Leu Trp Thr His Ala Glu Glu Val Asn Thr Ala Leu
260 265 270

Leu Ala Phe Leu Ala Lys Ala Gln Glu Ala Gln Lys Gln Lys Leu Leu
275 280 285

Thr Glu Val Glu Thr Tyr Val Leu Ser Ile Ile Pro Ser Gly Pro Leu
290 295 300

Lys Ala Glu Ile Ala Gln Arg Leu Glu Asp Val Phe Ala Gly Lys Asn
305 310 315 320

Thr Asp Leu Glu Val Leu Met Glu Trp Leu Lys Thr Arg Pro Ile Leu
325 330 335

Ser Pro Leu Thr Lys Gly Ile Leu Gly Phe Val Phe Thr Leu Thr Val
340 345 350

Pro Ser Glu Arg Gly Leu Gln Arg Arg Arg Phe Val Gln Asn Ala Leu
355 360 365

Asn Gly Asn Gly Asp Pro Asn Asn Met Asp Lys Ala Val Lys Leu Tyr
370 375 380

Arg Lys Leu Lys Arg Glu Ile Thr Phe His Gly Ala Lys Glu Ile Ser
385 390 395 400

Leu Ser Tyr Ser Ala Gly Ala Leu Ala Ser Cys Met Gly Leu Ile Tyr
405 410 415

Asn Arg Met Gly Ala Val Thr Thr Glu Val Ala Phe Gly Leu Val Cys
420 425 430

Ala Thr Cys Glu Gln Ile Ala Asp Ser Gln Gly Gly Gly Ser Gly Cys
435 440 445

Asp Cys Ala Trp His Leu Gly Glu Leu Val Trp Cys Thr Cys Gly Ser
450 455 460

Gly Gly Gly Leu Glu His His His His His His
465 470 475

<210> SEQ ID NO 27
<211> LENGTH: 475
<212> TYPE: PRT
<213> ORGANISM: Artificial Sequence
<220> FEATURE:
<223> OTHER INFORMATION: Engineered Self-Assembling Protein Nanocage
SAPNA_27

<400> SEQUENCE: 27

Met Pro Phe Ile Thr Val Gly Gln Glu Asn Ser Thr Ser Ile Asp Leu
1 5 10 15

Tyr Tyr Glu Asp His Gly Thr Gly Thr Pro Val Val Leu Ile His Gly
20 25 30

Phe Pro Leu Ser Gly His Ser Trp Glu Arg Gln Ser Ala Ala Leu Leu
35 40 45

Asp Ala Gly Tyr Arg Val Ile Thr Tyr Asp Arg Arg Gly Phe Gly Gln
50 55 60

Ser Ser Gln Pro Thr Thr Gly Tyr Asp Tyr Asp Thr Phe Ala Ala Asp
65 70 75 80

Leu Asn Thr Val Leu Glu Thr Leu Asp Leu Gln Asp Ala Val Leu Val
85 90 95

Gly Phe Ser Met Gly Thr Gly Glu Val Ala Arg Tyr Val Ser Ser Tyr

-continued

```
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Glu
    130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Lys Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Ala Pro Thr Thr Trp Tyr Thr
        195                 200                 205

Asp Phe Arg Ala Asp Ile Pro Arg Ile Asp Val Pro Ala Leu Ile Leu
    210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Glu Gly Ala
                245                 250                 255

Pro His Gly Leu Leu Trp Thr His Ala Glu Glu Val Asn Thr Ala Leu
            260                 265                 270

Leu Ala Phe Leu Ala Lys Ala Gln Glu Ala Gln Lys Gln Lys Leu Leu
        275                 280                 285

Thr Glu Val Glu Thr Tyr Val Leu Ser Ile Ile Pro Ser Gly Pro Leu
    290                 295                 300

Lys Ala Glu Ile Ala Gln Arg Leu Glu Asp Val Phe Ala Gly Lys Asn
305                 310                 315                 320

Thr Asp Leu Glu Val Leu Met Glu Trp Leu Lys Thr Arg Pro Ile Leu
                325                 330                 335

Ser Pro Leu Thr Lys Gly Ile Leu Gly Phe Val Phe Thr Leu Thr Val
            340                 345                 350

Pro Ser Glu Arg Gly Leu Gln Arg Arg Arg Phe Val Gln Asn Ala Leu
        355                 360                 365

Asn Gly Asn Gly Asp Pro Asn Asn Met Asp Lys Ala Val Lys Leu Tyr
    370                 375                 380

Arg Lys Leu Lys Arg Glu Ile Thr Phe His Gly Ala Lys Glu Ile Ser
385                 390                 395                 400

Leu Ser Tyr Ser Ala Gly Ala Leu Ala Ser Cys Met Gly Leu Ile Tyr
                405                 410                 415

Asn Arg Met Gly Ala Val Thr Thr Glu Val Ala Phe Gly Leu Val Cys
            420                 425                 430

Ala Thr Cys Glu Gln Ile Ala Asp Ser Gln Gly Gly Gly Ser Gly Cys
        435                 440                 445

Asp Cys Ala Trp His Leu Gly Glu Leu Val Trp Cys Thr Cys Gly Ser
    450                 455                 460

Gly Gly Gly Leu Glu His His His His His His
465                 470                 475
```

<210> SEQ ID NO 28
<211> LENGTH: 475
<212> TYPE: PRT
<213> ORGANISM: Artificial Sequence
<220> FEATURE:
<223> OTHER INFORMATION: Engineered Self-Assembling Protein Nanocage
      SAPNA_28

<400> SEQUENCE: 28

Met Pro Phe Ile Thr Val Gly Gln Glu Asn Ser Thr Ser Ile Asp Leu
1 5 10 15

Tyr Tyr Glu Asp His Gly Thr Gly Thr Pro Val Val Leu Ile His Gly
20 25 30

Phe Pro Leu Ser Gly His Ser Trp Glu Arg Gln Ser Ala Ala Leu Leu
35 40 45

Asp Ala Gly Tyr Arg Val Ile Thr Tyr Asp Arg Arg Gly Phe Gly Gln
50 55 60

Ser Ser Gln Pro Thr Thr Gly Tyr Asp Tyr Asp Thr Phe Ala Ala Asp
65 70 75 80

Leu Asn Thr Val Leu Glu Thr Leu Asp Leu Gln Asp Ala Val Leu Val
85 90 95

Gly Phe Ser Met Gly Thr Gly Glu Val Ala Arg Tyr Val Ser Ser Tyr
100 105 110

Gly Thr Ala Arg Ile Ala Ala Val Ala Phe Leu Ala Ser Leu Glu Pro
115 120 125

Phe Leu Leu Lys Thr Asp Asp Asn Pro Asp Gly Ala Ala Pro Gln Glu
130 135 140

Phe Phe Asp Gly Ile Val Ala Ala Val Lys Ala Asp Arg Tyr Ala Phe
145 150 155 160

Tyr Thr Gly Phe Phe Asn Asp Phe Tyr Asn Leu Asp Glu Asn Leu Gly
165 170 175

Thr Arg Ile Ser Glu Glu Ala Val Arg Asn Ser Trp Asn Thr Ala Ala
180 185 190

Ser Gly Gly Phe Phe Ala Ala Ala Ala Ala Pro Thr Thr Trp Tyr Thr
195 200 205

Asp Phe Arg Ala Asp Ile Pro Arg Ile Asp Val Pro Ala Leu Ile Leu
210 215 220

His Gly Thr Gly Asp Arg Thr Leu Pro Ile Lys Asn Thr Ala Arg Val
225 230 235 240

Phe His Lys Ala Leu Pro Ser Ala Glu Tyr Val Glu Val Glu Gly Ala
245 250 255

Pro His Gly Leu Leu Trp Thr His Ala Glu Glu Val Asn Thr Ala Leu
260 265 270

Leu Ala Phe Leu Ala Lys Ala Gln Glu Ala Gln Lys Gln Lys Leu Leu
275 280 285

Thr Glu Val Glu Thr Tyr Val Leu Ser Ile Ile Pro Ser Gly Pro Leu
290 295 300

Lys Ala Glu Ile Ala Gln Arg Leu Glu Asp Val Phe Ala Gly Lys Asn
305 310 315 320

Thr Asp Leu Glu Val Leu Met Glu Trp Leu Lys Thr Arg Pro Ile Leu
325 330 335

Ser Pro Leu Thr Lys Gly Ile Leu Gly Phe Val Phe Thr Leu Thr Val
340 345 350

Pro Ser Glu Arg Gly Leu Gln Arg Arg Arg Phe Val Gln Asn Ala Leu
355 360 365

Asn Gly Asn Gly Asp Pro Asn Asn Met Asp Lys Ala Val Lys Leu Tyr
370 375 380

Arg Lys Leu Lys Arg Glu Ile Thr Phe His Gly Ala Lys Glu Ile Ser
385 390 395 400

Leu Ser Tyr Ser Ala Gly Ala Leu Ala Ser Cys Met Gly Leu Ile Tyr

-continued

```
                405                 410                 415

Asn Arg Met Gly Ala Val Thr Thr Glu Val Ala Phe Gly Leu Val Cys
            420                 425                 430

Ala Thr Cys Glu Gln Ile Ala Asp Ser Gln Gly Gly Gly Ser Gly Cys
        435                 440                 445

Asp Cys Ala Trp His Leu Gly Glu Leu Val Trp Cys Thr Cys Gly Ser
    450                 455                 460

Gly Gly Gly Leu Glu His His His His His His
465                 470                 475


<210> SEQ ID NO 29
<211> LENGTH: 475
<212> TYPE: PRT
<213> ORGANISM: Artificial Sequence
<220> FEATURE:
<223> OTHER INFORMATION: Engineered Self-Assembling Protein Nanocage
      SAPNA_29

<400> SEQUENCE: 29

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Lys
    130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Lys Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Ala Pro Thr Thr Trp Tyr Thr
        195                 200                 205

Asp Phe Arg Ala Asp Ile Pro Arg Ile Asp Val Pro Ala Leu Ile Leu
    210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Glu Gly Ala
                245                 250                 255

Pro His Gly Leu Leu Trp Thr His Ala Glu Glu Val Asn Thr Ala Leu
            260                 265                 270

Leu Ala Phe Leu Ala Lys Ala Gln Glu Ala Gln Lys Gln Lys Leu Leu
        275                 280                 285
```

Thr Glu Val Glu Thr Tyr Val Leu Ser Ile Ile Pro Ser Gly Pro Leu
    290                 295                 300

Lys Ala Glu Ile Ala Gln Arg Leu Glu Asp Val Phe Ala Gly Lys Asn
305                 310                 315                 320

Thr Asp Leu Glu Val Leu Met Glu Trp Leu Lys Thr Arg Pro Ile Leu
                325                 330                 335

Ser Pro Leu Thr Lys Gly Ile Leu Gly Phe Val Phe Thr Leu Thr Val
            340                 345                 350

Pro Ser Glu Arg Gly Leu Gln Arg Arg Arg Phe Val Gln Asn Ala Leu
        355                 360                 365

Asn Gly Asn Gly Asp Pro Asn Asn Met Asp Lys Ala Val Lys Leu Tyr
    370                 375                 380

Arg Lys Leu Lys Arg Glu Ile Thr Phe His Gly Ala Lys Glu Ile Ser
385                 390                 395                 400

Leu Ser Tyr Ser Ala Gly Ala Leu Ala Ser Cys Met Gly Leu Ile Tyr
                405                 410                 415

Asn Arg Met Gly Ala Val Thr Thr Glu Val Ala Phe Gly Leu Val Cys
            420                 425                 430

Ala Thr Cys Glu Gln Ile Ala Asp Ser Gln Gly Gly Gly Ser Gly Cys
        435                 440                 445

Asp Cys Ala Trp His Leu Gly Glu Leu Val Trp Cys Thr Cys Gly Ser
    450                 455                 460

Gly Gly Gly Leu Glu His His His His His His
465                 470                 475

<210> SEQ ID NO 30
<211> LENGTH: 475
<212> TYPE: PRT
<213> ORGANISM: Artificial Sequence
<220> FEATURE:
<223> OTHER INFORMATION: Engineered Self-Assembling Protein Nanocage
      SAPNA_30

<400> SEQUENCE: 30

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Glu
    130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Lys Glu Asn Leu Gly
                165                 170                 175

Thr Arg Ile Ser Glu Glu Ala Val Arg Asn Ser Trp Asn Thr Ala Ala
180 185 190

Ser Gly Gly Phe Phe Ala Ala Ala Ala Ala Pro Thr Thr Trp Tyr Thr
195 200 205

Asp Phe Arg Ala Asp Ile Pro Arg Ile Asp Val Pro Ala Leu Ile Leu
210 215 220

His Gly Thr Gly Asp Arg Thr Leu Pro Ile Lys Asn Thr Ala Arg Val
225 230 235 240

Phe His Lys Ala Leu Pro Ser Ala Glu Tyr Val Glu Val Glu Gly Ala
245 250 255

Pro His Gly Leu Leu Trp Thr His Ala Glu Glu Val Asn Thr Ala Leu
260 265 270

Leu Ala Phe Leu Ala Lys Ala Gln Glu Ala Gln Lys Gln Lys Leu Leu
275 280 285

Thr Glu Val Glu Thr Tyr Val Leu Ser Ile Ile Pro Ser Gly Pro Leu
290 295 300

Lys Ala Glu Ile Ala Gln Arg Leu Glu Asp Val Phe Ala Gly Lys Asn
305 310 315 320

Thr Asp Leu Glu Val Leu Met Glu Trp Leu Lys Thr Arg Pro Ile Leu
325 330 335

Ser Pro Leu Thr Lys Gly Ile Leu Gly Phe Val Phe Thr Leu Thr Val
340 345 350

Pro Ser Glu Arg Gly Leu Gln Arg Arg Arg Phe Val Gln Asn Ala Leu
355 360 365

Asn Gly Asn Gly Asp Pro Asn Asn Met Asp Lys Ala Val Lys Leu Tyr
370 375 380

Arg Lys Leu Lys Arg Glu Ile Thr Phe His Gly Ala Lys Glu Ile Ser
385 390 395 400

Leu Ser Tyr Ser Ala Gly Ala Leu Ala Ser Cys Met Gly Leu Ile Tyr
405 410 415

Asn Arg Met Gly Ala Val Thr Thr Glu Val Ala Phe Gly Leu Val Cys
420 425 430

Ala Thr Cys Glu Gln Ile Ala Asp Ser Gln Gly Gly Gly Ser Gly Cys
435 440 445

Asp Cys Ala Trp His Leu Gly Glu Leu Val Trp Cys Thr Cys Gly Ser
450 455 460

Gly Gly Gly Leu Glu His His His His His His
465 470 475

<210> SEQ ID NO 31
<211> LENGTH: 475
<212> TYPE: PRT
<213> ORGANISM: Artificial Sequence
<220> FEATURE:
<223> OTHER INFORMATION: Engineered Self-Assembling Protein Nanocage SAPNA_31

<400> SEQUENCE: 31

Met Pro Phe Ile Thr Val Gly Gln Glu Asn Ser Thr Ser Ile Asp Leu
1 5 10 15

Tyr Tyr Glu Asp His Gly Thr Gly Thr Pro Val Val Leu Ile His Gly
20 25 30

Phe Pro Leu Ser Gly His Ser Trp Glu Arg Gln Ser Ala Ala Leu Leu
35 40 45

Asp Ala Gly Tyr Arg Val Ile Thr Tyr Asp Arg Arg Gly Phe Gly Gln

-continued

```
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Lys
    130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Ala Pro Thr Thr Trp Tyr Thr
        195                 200                 205

Asp Phe Arg Ala Asp Ile Pro Arg Ile Asp Val Pro Ala Leu Ile Leu
    210                 215                 220

His Gly Thr Gly Asp Arg Thr Leu Pro Ile Lys Asn Thr Ala Arg Val
225                 230                 235                 240

Phe His Lys Ala Leu Pro Ser Ala Glu Tyr Val Glu Val Glu Gly Ala
                245                 250                 255

Pro His Gly Leu Leu Trp Thr His Ala Glu Glu Val Asn Thr Ala Leu
            260                 265                 270

Leu Ala Phe Leu Ala Lys Ala Gln Glu Ala Gln Lys Gln Lys Leu Leu
        275                 280                 285

Thr Glu Val Glu Thr Tyr Val Leu Ser Ile Ile Pro Ser Gly Pro Leu
    290                 295                 300

Lys Ala Glu Ile Ala Gln Arg Leu Glu Asp Val Phe Ala Gly Lys Asn
305                 310                 315                 320

Thr Asp Leu Glu Val Leu Met Glu Trp Leu Lys Thr Arg Pro Ile Leu
                325                 330                 335

Ser Pro Leu Thr Lys Gly Ile Leu Gly Phe Val Phe Thr Leu Thr Val
            340                 345                 350

Pro Ser Glu Arg Gly Leu Gln Arg Arg Arg Phe Val Gln Asn Ala Leu
        355                 360                 365

Asn Gly Asn Gly Asp Pro Asn Asn Met Asp Lys Ala Val Lys Leu Tyr
    370                 375                 380

Arg Lys Leu Lys Arg Glu Ile Thr Phe His Gly Ala Lys Glu Ile Ser
385                 390                 395                 400

Leu Ser Tyr Ser Ala Gly Ala Leu Ala Ser Cys Met Gly Leu Ile Tyr
                405                 410                 415

Asn Arg Met Gly Ala Val Thr Thr Glu Val Ala Phe Gly Leu Val Cys
            420                 425                 430

Ala Thr Cys Glu Gln Ile Ala Asp Ser Gln Gly Gly Gly Ser Gly Cys
        435                 440                 445

Asp Cys Ala Trp His Leu Gly Glu Leu Val Trp Cys Thr Cys Gly Ser
    450                 455                 460

Gly Gly Gly Leu Glu His His His His His His
465                 470                 475
```

<210> SEQ ID NO 32
<211> LENGTH: 475
<212> TYPE: PRT
<213> ORGANISM: Artificial Sequence
<220> FEATURE:
<223> OTHER INFORMATION: Engineered Self-Assembling Protein Nanocage
SAPNA_32

<400> SEQUENCE: 32

```
Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Lys
    130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Lys Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Ala Pro Thr Thr Trp Tyr Thr
        195                 200                 205

Asp Phe Arg Ala Asp Ile Pro Arg Ile Asp Val Pro Ala Leu Ile Leu
    210                 215                 220

His Gly Thr Gly Asp Arg Thr Leu Pro Ile Lys Asn Thr Ala Arg Val
225                 230                 235                 240

Phe His Lys Ala Leu Pro Ser Ala Glu Tyr Val Glu Val Glu Gly Ala
                245                 250                 255

Pro His Gly Leu Leu Trp Thr His Ala Glu Glu Val Asn Thr Ala Leu
            260                 265                 270

Leu Ala Phe Leu Ala Lys Ala Gln Glu Ala Gln Lys Gln Lys Leu Leu
        275                 280                 285

Thr Glu Val Glu Thr Tyr Val Leu Ser Ile Ile Pro Ser Gly Pro Leu
    290                 295                 300

Lys Ala Glu Ile Ala Gln Arg Leu Glu Asp Val Phe Ala Gly Lys Asn
305                 310                 315                 320

Thr Asp Leu Glu Val Leu Met Glu Trp Leu Lys Thr Arg Pro Ile Leu
                325                 330                 335

Ser Pro Leu Thr Lys Gly Ile Leu Gly Phe Val Phe Thr Leu Thr Val
            340                 345                 350

Pro Ser Glu Arg Gly Leu Gln Arg Arg Arg Phe Val Gln Asn Ala Leu
```

```
        355                 360                 365

Asn Gly Asn Gly Asp Pro Asn Asn Met Asp Lys Ala Val Lys Leu Tyr
    370                 375                 380

Arg Lys Leu Lys Arg Glu Ile Thr Phe His Gly Ala Lys Glu Ile Ser
385                 390                 395                 400

Leu Ser Tyr Ser Ala Gly Ala Leu Ala Ser Cys Met Gly Leu Ile Tyr
                405                 410                 415

Asn Arg Met Gly Ala Val Thr Thr Glu Val Ala Phe Gly Leu Val Cys
            420                 425                 430

Ala Thr Cys Glu Gln Ile Ala Asp Ser Gln Gly Gly Gly Ser Gly Cys
        435                 440                 445

Asp Cys Ala Trp His Leu Gly Glu Leu Val Trp Cys Thr Cys Gly Ser
    450                 455                 460

Gly Gly Gly Leu Glu His His His His His His
465                 470                 475


<210> SEQ ID NO 33
<211> LENGTH: 475
<212> TYPE: PRT
<213> ORGANISM: Artificial Sequence
<220> FEATURE:
<223> OTHER INFORMATION: Engineered Self-Assembling Protein Nanocage
      SAPNA_33

<400> SEQUENCE: 33

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Ala Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Glu
    130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Ala Pro Thr Thr Trp Tyr Thr
        195                 200                 205

Asp Phe Arg Ala Asp Ile Pro Arg Ile Asp Val Pro Ala Leu Ile Leu
    210                 215                 220

His Gly Thr Gly Asp Arg Thr Leu Pro Ile Glu Asn Thr Ala Arg Val
225                 230                 235                 240
```

```
Phe His Lys Ala Leu Pro Ser Ala Glu Tyr Val Glu Val Glu Gly Ala
            245                 250                 255

Pro His Gly Leu Leu Trp Thr His Ala Glu Glu Val Asn Thr Ala Leu
            260                 265                 270

Leu Ala Phe Leu Ala Lys Ala Gln Glu Ala Gln Lys Gln Lys Leu Leu
        275                 280                 285

Thr Glu Val Glu Thr Tyr Val Leu Ser Ile Ile Pro Ser Gly Pro Leu
    290                 295                 300

Lys Ala Glu Ile Ala Gln Arg Leu Glu Asp Val Phe Ala Gly Lys Asn
305                 310                 315                 320

Thr Asp Leu Glu Val Leu Met Glu Trp Leu Lys Thr Arg Pro Ile Leu
                325                 330                 335

Ser Pro Leu Thr Lys Gly Ile Leu Gly Phe Val Phe Thr Leu Thr Val
            340                 345                 350

Pro Ser Glu Arg Gly Leu Gln Arg Arg Arg Phe Val Gln Asn Ala Leu
        355                 360                 365

Asn Gly Asn Gly Asp Pro Asn Asn Met Asp Lys Ala Val Lys Leu Tyr
    370                 375                 380

Arg Lys Leu Lys Arg Glu Ile Thr Phe His Gly Ala Lys Glu Ile Ser
385                 390                 395                 400

Leu Ser Tyr Ser Ala Gly Ala Leu Ala Ser Cys Met Gly Leu Ile Tyr
                405                 410                 415

Asn Arg Met Gly Ala Val Thr Thr Glu Val Ala Phe Gly Leu Val Cys
            420                 425                 430

Ala Thr Cys Glu Gln Ile Ala Asp Ser Gln Gly Gly Gly Ser Gly Cys
        435                 440                 445

Asp Cys Ala Trp His Leu Gly Glu Leu Val Trp Cys Thr Cys Gly Ser
    450                 455                 460

Gly Gly Gly Leu Glu His His His His His His
465                 470                 475


<210> SEQ ID NO 34
<211> LENGTH: 478
<212> TYPE: PRT
<213> ORGANISM: Artificial Sequence
<220> FEATURE:
<223> OTHER INFORMATION: Engineered Self-Assembling Protein Nanocage
      SAPNA_34

<400> SEQUENCE: 34

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125
```

```
Phe Leu Leu Lys Thr Asp Asp Asn Pro Asp Gly Ala Ala Pro Gln Glu
    130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Ala Pro Thr Thr Trp Tyr Thr
        195                 200                 205

Asp Phe Arg Ala Asp Ile Pro Arg Ile Asp Val Pro Ala Leu Ile Leu
    210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Glu Gly Ala
                245                 250                 255

Pro His Gly Leu Leu Trp Thr His Ala Glu Glu Val Asn Thr Ala Leu
            260                 265                 270

Leu Ala Phe Leu Ala Lys Ala Gln Glu Ala Gln Lys Gln Lys Leu Leu
        275                 280                 285

Thr Glu Val Glu Thr Tyr Val Leu Ser Ile Ile Pro Ser Gly Pro Leu
    290                 295                 300

Lys Ala Glu Ile Ala Gln Arg Leu Glu Asp Val Phe Ala Gly Lys Asn
305                 310                 315                 320

Thr Asp Leu Glu Val Leu Met Glu Trp Leu Lys Thr Arg Pro Ile Leu
                325                 330                 335

Ser Pro Leu Thr Lys Gly Ile Leu Gly Phe Val Phe Thr Leu Thr Val
            340                 345                 350

Pro Ser Glu Arg Gly Leu Gln Arg Arg Arg Phe Val Gln Asn Ala Leu
        355                 360                 365

Asn Gly Asn Gly Asp Pro Asn Asn Met Asp Lys Ala Val Lys Leu Tyr
    370                 375                 380

Arg Lys Leu Lys Arg Glu Ile Thr Phe His Gly Ala Lys Glu Ile Ser
385                 390                 395                 400

Leu Ser Tyr Ser Ala Gly Ala Leu Ala Ser Cys Met Gly Leu Ile Tyr
                405                 410                 415

Asn Arg Met Gly Ala Val Thr Thr Glu Val Ala Phe Gly Leu Val Cys
            420                 425                 430

Ala Thr Cys Glu Gln Ile Ala Asp Ser Gln Gly Gly Gly Ser Gly Gly
        435                 440                 445

Gly Gly Cys Asp Cys Ala Trp His Leu Gly Glu Leu Val Trp Cys Thr
    450                 455                 460

Cys Gly Ser Gly Gly Gly Leu Glu His His His His His His
465                 470                 475


<210> SEQ ID NO 35
<211> LENGTH: 480
<212> TYPE: PRT
<213> ORGANISM: Artificial Sequence
<220> FEATURE:
<223> OTHER INFORMATION: Engineered Self-Assembling Protein Nanocage
      SAPNA_35

<400> SEQUENCE: 35

Met Pro Phe Ile Thr Val Gly Gln Glu Asn Ser Thr Ser Ile Asp Leu
```

-continued 1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Glu
    130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Ala Pro Thr Thr Trp Tyr Thr
        195                 200                 205

Asp Phe Arg Ala Asp Ile Pro Arg Ile Asp Val Pro Ala Leu Ile Leu
    210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Glu Gly Ala
                245                 250                 255

Pro His Gly Leu Leu Trp Thr His Ala Glu Glu Val Asn Thr Ala Leu
            260                 265                 270

Leu Ala Phe Leu Ala Lys Ala Gln Glu Ala Gln Lys Gln Lys Leu Leu
        275                 280                 285

Thr Glu Val Glu Thr Tyr Val Leu Ser Ile Ile Pro Ser Gly Pro Leu
    290                 295                 300

Lys Ala Glu Ile Ala Gln Arg Leu Glu Asp Val Phe Ala Gly Lys Asn
305                 310                 315                 320

Thr Asp Leu Glu Val Leu Met Glu Trp Leu Lys Thr Arg Pro Ile Leu
                325                 330                 335

Ser Pro Leu Thr Lys Gly Ile Leu Gly Phe Val Phe Thr Leu Thr Val
            340                 345                 350

Pro Ser Glu Arg Gly Leu Gln Arg Arg Arg Phe Val Gln Asn Ala Leu
        355                 360                 365

Asn Gly Asn Gly Asp Pro Asn Asn Met Asp Lys Ala Val Lys Leu Tyr
    370                 375                 380

Arg Lys Leu Lys Arg Glu Ile Thr Phe His Gly Ala Lys Glu Ile Ser
385                 390                 395                 400

Leu Ser Tyr Ser Ala Gly Ala Leu Ala Ser Cys Met Gly Leu Ile Tyr
                405                 410                 415

Asn Arg Met Gly Ala Val Thr Thr Glu Val Ala Phe Gly Leu Val Cys
            420                 425                 430

```
Ala Thr Cys Glu Gln Ile Ala Asp Ser Gln Gly Gly Gly Ser Gly Gly
        435                 440                 445

Gly Ser Gly Gly Cys Asp Cys Ala Trp His Leu Gly Glu Leu Val Trp
    450                 455                 460

Cys Thr Cys Gly Ser Gly Gly Gly Leu Glu His His His His His His
465                 470                 475                 480


<210> SEQ ID NO 36
<211> LENGTH: 535
<212> TYPE: PRT
<213> ORGANISM: Artificial Sequence
<220> FEATURE:
<223> OTHER INFORMATION: Engineered Self-Assembling Protein Nanocage
      SAPNA_36

<400> SEQUENCE: 36

Met Pro Phe Ile Thr Val Gly Gln Glu Asn Ser Thr Ser Ile Asp Leu
1               5                   10                  15

Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Glu
    130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Ala Pro Thr Thr Trp Tyr Thr
        195                 200                 205

Asp Phe Arg Ala Asp Ile Pro Arg Ile Asp Val Pro Ala Leu Ile Leu
    210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Glu Gly Ala
                245                 250                 255

Pro His Gly Leu Leu Trp Thr His Ala Glu Glu Val Asn Thr Ala Leu
            260                 265                 270

Leu Ala Phe Leu Ala Lys Ala Gln Glu Ala Gln Lys Gln Lys Leu Leu
        275                 280                 285

Thr Glu Val Glu Thr Tyr Val Leu Ser Ile Ile Pro Ser Gly Pro Leu
    290                 295                 300

Lys Ala Glu Ile Ala Gln Arg Leu Glu Asp Val Phe Ala Gly Lys Asn
```

305 310 315 320

Thr Asp Leu Glu Val Leu Met Glu Trp Leu Lys Thr Arg Pro Ile Leu
325 330 335

Ser Pro Leu Thr Lys Gly Ile Leu Gly Phe Val Phe Thr Leu Thr Val
340 345 350

Pro Ser Glu Arg Gly Leu Gln Arg Arg Arg Phe Val Gln Asn Ala Leu
355 360 365

Asn Gly Asn Gly Asp Pro Asn Asn Met Asp Lys Ala Val Lys Leu Tyr
370 375 380

Arg Lys Leu Lys Arg Glu Ile Thr Phe His Gly Ala Lys Glu Ile Ser
385 390 395 400

Leu Ser Tyr Ser Ala Gly Ala Leu Ala Ser Cys Met Gly Leu Ile Tyr
405 410 415

Asn Arg Met Gly Ala Val Thr Thr Glu Val Ala Phe Gly Leu Val Cys
420 425 430

Ala Thr Cys Glu Gln Ile Ala Asp Ser Gln Gly Gly Gly Ser Gly Gly
435 440 445

Gly Ser Gly Gly Gly Ser Gly Gly Gly Ser Gly Gly Gly Ser Gly Gly
450 455 460

Gly Ser Gly Gly Gly Ser Gly Gly Gly Ser Gly Gly Gly Ser Gly Gly
465 470 475 480

Gly Ser Gly Gly Gly Ser Gly Gly Gly Ser Gly Gly Gly Ser Gly Gly
485 490 495

Gly Ser Gly Gly Gly Ser Gly Gly Gly Ser Gly Cys Asp Cys Ala Trp
500 505 510

His Leu Gly Glu Leu Val Trp Cys Thr Cys Gly Ser Gly Gly Gly Leu
515 520 525

Asp His His His His His His
530 535

<210> SEQ ID NO 37
<211> LENGTH: 478
<212> TYPE: PRT
<213> ORGANISM: Artificial Sequence
<220> FEATURE:
<223> OTHER INFORMATION: Engineered Self-Assembling Protein Nanocage
SAPNA_37

<400> SEQUENCE: 37

Met Pro Phe Ile Thr Val Gly Gln Glu Asn Ser Thr Ser Ile Asp Leu
1 5 10 15

Tyr Tyr Glu Asp His Gly Thr Gly Thr Pro Val Val Leu Ile His Gly
20 25 30

Phe Pro Leu Ser Gly His Ser Trp Glu Arg Gln Ser Ala Ala Leu Leu
35 40 45

Asp Ala Gly Tyr Arg Val Ile Thr Tyr Asp Arg Arg Gly Phe Gly Gln
50 55 60

Ser Ser Gln Pro Thr Thr Gly Tyr Asp Tyr Asp Thr Phe Ala Ala Asp
65 70 75 80

Leu Asn Thr Val Leu Glu Thr Leu Asp Leu Gln Asp Ala Val Leu Val
85 90 95

Gly Phe Ser Met Gly Thr Gly Glu Val Ala Arg Tyr Val Ser Ser Tyr
100 105 110

Gly Thr Ala Arg Ile Ala Ala Val Ala Phe Leu Ala Ser Leu Glu Pro
115 120 125

-continued

Phe Leu Leu Lys Thr Asp Asp Asn Pro Asp Gly Ala Ala Pro Gln Glu
    130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Ala Pro Thr Thr Trp Tyr Thr
        195                 200                 205

Asp Phe Arg Ala Asp Ile Pro Arg Ile Asp Val Pro Ala Leu Ile Leu
    210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Glu Gly Ala
                245                 250                 255

Pro His Gly Leu Leu Trp Thr His Ala Glu Glu Val Asn Thr Ala Leu
            260                 265                 270

Leu Ala Phe Leu Ala Lys Ala Gln Glu Ala Gln Lys Gln Lys Leu Leu
        275                 280                 285

Thr Glu Val Glu Thr Tyr Val Leu Ser Ile Ile Pro Ser Gly Pro Leu
    290                 295                 300

Lys Ala Glu Ile Ala Gln Arg Leu Glu Asp Val Phe Ala Gly Arg Trp
305                 310                 315                 320

Gly Ser Gly Ala Asp Cys Ala Trp His Leu Gly Glu Leu Val Trp Cys
                325                 330                 335

Thr Ala Gly Ser Gly Trp Glu Asp Leu Glu Val Leu Met Glu Trp Leu
            340                 345                 350

Lys Thr Arg Pro Ile Leu Ser Pro Leu Thr Lys Gly Ile Leu Gly Phe
        355                 360                 365

Val Phe Thr Leu Thr Val Pro Ser Glu Arg Gly Leu Gln Arg Arg Arg
    370                 375                 380

Phe Val Gln Asn Ala Leu Asn Gly Asn Gly Asp Pro Asn Asn Met Asp
385                 390                 395                 400

Lys Ala Val Lys Leu Tyr Arg Lys Leu Lys Arg Glu Ile Thr Phe His
                405                 410                 415

Gly Ala Lys Glu Ile Ser Leu Ser Tyr Ser Ala Gly Ala Leu Ala Ser
            420                 425                 430

Cys Met Gly Leu Ile Tyr Asn Arg Met Gly Ala Val Thr Thr Glu Val
        435                 440                 445

Ala Phe Gly Leu Val Cys Ala Thr Cys Glu Gln Ile Ala Asp Ser Gln
    450                 455                 460

His Arg Ser His Arg Gln Leu Glu His His His His His His
465                 470                 475

<210> SEQ ID NO 38
<211> LENGTH: 478
<212> TYPE: PRT
<213> ORGANISM: Artificial Sequence
<220> FEATURE:
<223> OTHER INFORMATION: Engineered Self-Assembling Protein Nanocage
      SAPNA_38

<400> SEQUENCE: 38

Met Pro Phe Ile Thr Val Gly Gln Glu Asn Ser Thr Ser Ile Asp Leu
1               5                   10                  15

-continued

```
Tyr Tyr Glu Asp His Gly Thr Gly Thr Pro Val Val Leu Ile His Gly
            20                  25                  30

Phe Pro Leu Ser Gly His Ser Trp Glu Arg Gln Ser Ala Ala Leu Leu
        35                  40                  45

Asp Ala Gly Tyr Arg Val Ile Thr Tyr Asp Arg Arg Gly Phe Gly Gln
    50                  55                  60

Ser Ser Gln Pro Thr Thr Gly Tyr Asp Tyr Asp Thr Phe Ala Ala Asp
65                  70                  75                  80

Leu Asn Thr Val Leu Glu Thr Leu Asp Leu Gln Asp Ala Val Leu Val
                85                  90                  95

Gly Phe Ser Met Gly Thr Gly Glu Val Ala Arg Tyr Val Ser Ser Tyr
            100                 105                 110

Gly Thr Ala Arg Ile Ala Ala Val Ala Phe Leu Ala Ser Leu Glu Pro
        115                 120                 125

Phe Leu Leu Lys Thr Asp Asp Asn Pro Asp Gly Ala Ala Pro Gln Glu
    130                 135                 140

Phe Phe Asp Gly Ile Val Ala Ala Val Lys Ala Asp Arg Tyr Ala Phe
145                 150                 155                 160

Tyr Thr Gly Phe Phe Asn Asp Phe Tyr Asn Leu Asp Glu Asn Leu Gly
                165                 170                 175

Thr Arg Ile Ser Glu Glu Ala Val Arg Asn Ser Trp Asn Thr Ala Ala
            180                 185                 190

Ser Gly Gly Phe Phe Ala Ala Ala Ala Ala Pro Thr Thr Trp Tyr Thr
        195                 200                 205

Asp Phe Arg Ala Asp Ile Pro Arg Ile Asp Val Pro Ala Leu Ile Leu
    210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Glu Gly Ala
                245                 250                 255

Pro His Gly Leu Leu Trp Thr His Ala Glu Glu Val Asn Thr Ala Leu
            260                 265                 270

Leu Ala Phe Leu Ala Lys Ala Gln Glu Ala Gln Lys Gln Lys Leu Leu
        275                 280                 285

Thr Glu Val Glu Thr Tyr Val Leu Ser Ile Ile Pro Ser Gly Pro Leu
    290                 295                 300

Lys Ala Glu Ile Ala Gln Arg Leu Glu Asp Val Phe Ala Gly Gly Gly
305                 310                 315                 320

Arg Trp Gly Ala Asp Cys Ala Trp His Leu Gly Glu Leu Val Trp Cys
                325                 330                 335

Thr Ala Gly Trp Glu Gly Gly Asp Leu Glu Val Leu Met Glu Trp Leu
            340                 345                 350

Lys Thr Arg Pro Ile Leu Ser Pro Leu Thr Lys Gly Ile Leu Gly Phe
        355                 360                 365

Val Phe Thr Leu Thr Val Pro Ser Glu Arg Gly Leu Gln Arg Arg Arg
    370                 375                 380

Phe Val Gln Asn Ala Leu Asn Gly Asn Gly Asp Pro Asn Asn Met Asp
385                 390                 395                 400

Lys Ala Val Lys Leu Tyr Arg Lys Leu Lys Arg Glu Ile Thr Phe His
                405                 410                 415

Gly Ala Lys Glu Ile Ser Leu Ser Tyr Ser Ala Gly Ala Leu Ala Ser
            420                 425                 430
```

-continued

Cys Met Gly Leu Ile Tyr Asn Arg Met Gly Ala Val Thr Thr Glu Val
435 440 445

Ala Phe Gly Leu Val Cys Ala Thr Cys Glu Gln Ile Ala Asp Ser Gln
450 455 460

His Arg Ser His Arg Gln Leu Glu His His His His His His
465 470 475

<210> SEQ ID NO 39
<211> LENGTH: 470
<212> TYPE: PRT
<213> ORGANISM: Artificial Sequence
<220> FEATURE:
<223> OTHER INFORMATION: Engineered Self-Assembling Protein Nanocage SAPNA_39

<400> SEQUENCE: 39

Met Pro Phe Ile Thr Val Gly Gln Glu Asn Ser Thr Ser Ile Asp Leu
1 5 10 15

Tyr Tyr Glu Asp His Gly Thr Gly Thr Pro Val Val Leu Ile His Gly
20 25 30

Phe Pro Leu Ser Gly His Ser Trp Glu Arg Gln Ser Ala Ala Leu Leu
35 40 45

Asp Ala Gly Tyr Arg Val Ile Thr Tyr Asp Arg Arg Gly Phe Gly Gln
50 55 60

Ser Ser Gln Pro Thr Thr Gly Tyr Asp Tyr Asp Thr Phe Ala Ala Asp
65 70 75 80

Leu Asn Thr Val Leu Glu Thr Leu Asp Leu Gln Asp Ala Val Leu Val
85 90 95

Gly Phe Ser Met Gly Thr Gly Glu Val Ala Arg Tyr Val Ser Ser Tyr
100 105 110

Gly Thr Ala Arg Ile Ala Ala Val Ala Phe Leu Ala Ser Leu Glu Pro
115 120 125

Phe Leu Leu Lys Thr Asp Asp Asn Pro Asp Gly Ala Ala Pro Gln Glu
130 135 140

Phe Phe Asp Gly Ile Val Ala Ala Val Lys Ala Asp Arg Tyr Ala Phe
145 150 155 160

Tyr Thr Gly Phe Phe Asn Asp Phe Tyr Asn Leu Asp Glu Asn Leu Gly
165 170 175

Thr Arg Ile Ser Glu Glu Ala Val Arg Asn Ser Trp Asn Thr Ala Ala
180 185 190

Ser Gly Gly Phe Phe Ala Ala Ala Ala Ala Pro Thr Thr Trp Tyr Thr
195 200 205

Asp Phe Arg Ala Asp Ile Pro Arg Ile Asp Val Pro Ala Leu Ile Leu
210 215 220

His Gly Thr Gly Asp Arg Thr Leu Pro Ile Glu Asn Thr Ala Arg Val
225 230 235 240

Phe His Lys Ala Leu Pro Ser Ala Glu Tyr Val Glu Val Glu Gly Ala
245 250 255

Pro His Gly Leu Leu Trp Thr His Ala Glu Glu Val Asn Thr Ala Leu
260 265 270

Leu Ala Phe Leu Ala Lys Ala Gln Glu Ala Gln Lys Gln Lys Leu Leu
275 280 285

Thr Glu Val Glu Thr Tyr Val Leu Ser Ile Ile Pro Ser Gly Pro Leu
290 295 300

Lys Ala Glu Ile Ala Gln Arg Leu Glu Asp Val Phe Ala Gly Gly Ala
305 310 315 320

Asp Cys Ala Trp His Leu Gly Glu Leu Val Trp Cys Thr Ala Gly Asp
325 330 335

Leu Glu Val Leu Met Glu Trp Leu Lys Thr Arg Pro Ile Leu Ser Pro
340 345 350

Leu Thr Lys Gly Ile Leu Gly Phe Val Phe Thr Leu Thr Val Pro Ser
355 360 365

Glu Arg Gly Leu Gln Arg Arg Arg Phe Val Gln Asn Ala Leu Asn Gly
370 375 380

Asn Gly Asp Pro Asn Asn Met Asp Lys Ala Val Lys Leu Tyr Arg Lys
385 390 395 400

Leu Lys Arg Glu Ile Thr Phe His Gly Ala Lys Glu Ile Ser Leu Ser
405 410 415

Tyr Ser Ala Gly Ala Leu Ala Ser Cys Met Gly Leu Ile Tyr Asn Arg
420 425 430

Met Gly Ala Val Thr Thr Glu Val Ala Phe Gly Leu Val Cys Ala Thr
435 440 445

Cys Glu Gln Ile Ala Asp Ser Gln His Arg Ser His Arg Gln Leu Glu
450 455 460

His His His His His His
465 470

<210> SEQ ID NO 40
<211> LENGTH: 456
<212> TYPE: PRT
<213> ORGANISM: Artificial Sequence
<220> FEATURE:
<223> OTHER INFORMATION: Engineered Self-Assembling Protein Nanocage SAPNA_40

<400> SEQUENCE: 40

Met Pro Phe Ile Thr Val Gly Gln Glu Asn Ser Thr Ser Ile Asp Leu
1 5 10 15

Tyr Tyr Glu Asp His Gly Thr Gly Thr Pro Val Val Leu Ile His Gly
20 25 30

Phe Pro Leu Ser Gly His Ser Trp Glu Arg Gln Ser Ala Ala Leu Leu
35 40 45

Asp Ala Gly Tyr Arg Val Ile Thr Tyr Asp Arg Arg Gly Phe Gly Gln
50 55 60

Ser Ser Gln Pro Thr Thr Gly Tyr Asp Tyr Asp Thr Phe Ala Ala Asp
65 70 75 80

Leu Asn Thr Val Leu Glu Thr Leu Asp Leu Gln Asp Ala Val Leu Val
85 90 95

Gly Phe Ser Met Gly Thr Gly Glu Val Ala Arg Tyr Val Ser Ser Tyr
100 105 110

Gly Thr Ala Arg Ile Ala Ala Val Ala Phe Leu Ala Ser Leu Glu Pro
115 120 125

Phe Leu Leu Lys Thr Asp Asp Asn Pro Asp Gly Ala Ala Pro Gln Glu
130 135 140

Phe Phe Asp Gly Ile Val Ala Ala Val Lys Ala Asp Arg Tyr Ala Phe
145 150 155 160

Tyr Thr Gly Phe Phe Asn Asp Phe Tyr Asn Leu Asp Glu Asn Leu Gly
165 170 175

Thr Arg Ile Ser Glu Glu Ala Val Arg Asn Ser Trp Asn Thr Ala Ala
180 185 190

Ser Gly Gly Phe Phe Ala Ala Ala Ala Ala Pro Thr Thr Trp Tyr Thr

-continued

```
        195                 200                 205

Asp Phe Arg Ala Asp Ile Pro Arg Ile Asp Val Pro Ala Leu Ile Leu
    210                 215                 220

His Gly Thr Gly Asp Arg Thr Leu Pro Ile Glu Asn Thr Ala Arg Val
225                 230                 235                 240

Phe His Lys Ala Leu Pro Ser Ala Glu Tyr Val Glu Val Glu Gly Ala
                245                 250                 255

Pro His Gly Leu Leu Trp Thr His Ala Glu Glu Val Asn Thr Ala Leu
            260                 265                 270

Leu Ala Phe Leu Ala Lys Ala Gln Glu Ala Gln Lys Gln Lys Leu Leu
        275                 280                 285

Thr Glu Val Glu Thr Tyr Val Leu Ser Ile Ile Pro Ser Gly Pro Leu
    290                 295                 300

Lys Ala Glu Ile Ala Gln Arg Leu Glu Asp Val Phe Ala Gly Lys Asn
305                 310                 315                 320

Thr Asp Leu Glu Val Leu Met Glu Trp Leu Lys Thr Arg Pro Ile Leu
                325                 330                 335

Ser Pro Leu Thr Lys Gly Ile Leu Gly Phe Val Phe Thr Leu Thr Val
            340                 345                 350

Pro Ser Glu Arg Gly Leu Gln Arg Arg Arg Phe Val Gln Asn Ala Leu
        355                 360                 365

Asn Gly Asn Gly Asp Pro Asn Asn Met Asp Lys Ala Val Lys Leu Tyr
    370                 375                 380

Arg Lys Leu Lys Arg Glu Ile Thr Phe His Gly Ala Lys Glu Ile Ser
385                 390                 395                 400

Leu Ser Tyr Ser Ala Gly Ala Leu Ala Ser Cys Met Gly Leu Ile Tyr
                405                 410                 415

Asn Arg Met Gly Ala Val Thr Thr Glu Val Ala Phe Gly Leu Val Cys
            420                 425                 430

Ala Thr Cys Glu Gln Ile Ala Asp Ser Gln His Arg Ser His Arg Gln
        435                 440                 445

Leu Glu His His His His His His
    450                 455


<210> SEQ ID NO 41
<211> LENGTH: 13
<212> TYPE: PRT
<213> ORGANISM: Artificial Sequence
<220> FEATURE:
<223> OTHER INFORMATION: Peptide capable of binding to the Fc-region of
      IgG

<400> SEQUENCE: 41

Asp Cys Ala Trp His Leu Gly Glu Leu Val Trp Cys Thr
1               5                   10


<210> SEQ ID NO 42
<211> LENGTH: 17
<212> TYPE: PRT
<213> ORGANISM: Artificial Sequence
<220> FEATURE:
<223> OTHER INFORMATION: Peptide capable of binding to the Fc-region of
      IgG

<400> SEQUENCE: 42

Gly Cys Asp Cys Ala Trp His Leu Gly Glu Leu Val Trp Cys Thr Cys
1               5                   10                  15

Gly
```

-continued

```
<210> SEQ ID NO 43
<211> LENGTH: 10
<212> TYPE: PRT
<213> ORGANISM: Artificial Sequence
<220> FEATURE:
<223> OTHER INFORMATION: Peptide engineered for Polypeptide 2

<400> SEQUENCE: 43

Leu Thr Glu Val Glu Thr Tyr Val Leu Ser
1               5                   10


<210> SEQ ID NO 44
<211> LENGTH: 13
<212> TYPE: PRT
<213> ORGANISM: Artificial Sequence
<220> FEATURE:
<223> OTHER INFORMATION: Peptide engineered for Polypeptide 3

<400> SEQUENCE: 44

Phe Thr Leu Thr Val Pro Ser Glu Arg Gly Leu Gln Arg
1               5                   10


<210> SEQ ID NO 45
<211> LENGTH: 9
<212> TYPE: PRT
<213> ORGANISM: Artificial Sequence
<220> FEATURE:
<223> OTHER INFORMATION: Peptide engineered for Polypeptide 3

<400> SEQUENCE: 45

Cys Ala Thr Cys Glu Gln Ile Ala Asp
1               5
```

SELF-ASSEMBLING PROTEIN NANOCAGE DECORATED WITH ANTIBODIES (SAPNA) AND PARTS THEREOF

RELATED PATENT APPLICATIONS

The application is a U.S. National Phase of International Application No. PCT/US2020/030142, filed Apr. 27, 2020, which claims priority to U.S. Provisional Patent Application Ser. No. 62/838,826, filed Apr. 25, 2019, each of which applications is herein incorporated by reference in its entirety.

STATEMENT OF GOVERNMENTAL SUPPORT

The invention was made with government support under Contract Nos. DE-AC02-05CH11231 awarded by the U.S. Department of Energy. The government has certain rights in the invention.

SEQUENCE LISTING PROVIDED AS ASCII FORMAT FILE

This application contains a Sequence Listing submitted electronically in ASCII format and is herein incorporated by reference in its entirety. Said ASCII copy, created on Oct. 21, 2021, is named 077429_1276141_SEQ_LST.txt and is 170,060 bytes in size.

FIELD OF THE INVENTION

The present invention is in the field of production of protein-based antibody scaffolds.

BACKGROUND OF THE INVENTION

Therapeutic monoclonal antibodies are a massive force in the biopharmaceutical industry, while cancer immunotherapy is a booming area of intense research. According to Ecker et al. (5), in 2013, monoclonal antibody products represented nearly $75 billion, and approximately half of the total sales of all biopharmaceutical products. To put that in perspective, only 47 monoclonal antibody products had been approved for use in the US or Europe as of late 2014. Consequently, there is huge room for growth, and it is probable that most large pharmaceutical companies have an antibody development program. Indeed, it is predicted that approximately 70 new monoclonal antibody products will be on the market by 2020, resulting in almost $125 billion in global sales (5).

U.S. Pat. No. 6,756,039 (Yeates, Padilla, and Colovos) discloses fusion proteins capable of self-assembling into regular structures, wherein the fusion proteins comprise at least two oligomerization domains rigidly linked together, e.g., through an alpha helical linking group.

U.S. Pat. No. 7,608,681 (Dennis, Lowman and DeLano) discloses peptide ligands with affinity for IgG or for serum albumin.

U.S. Pat. No. 8,969,521 (Baker, King, Sheffler and, Yeates) discloses a general method for designing self-assembling protein nanomaterials, and an isolated polypeptide, comprising a specific 184 amino acid sequence, capable of forming a multimeric assembly.

U.S. Patent Application Publication No. 20070218547 (Yeates, Padilla, Yoshida, and Colovos) discloses self assembling proteins for producing extended materials, including a fusion protein comprising a first oligomerization domain that naturally associates into homodimeric structures and a second oligomerization domain that naturally associates into homotetrameric structures, wherein said first and second oligomerization domains are rigidly linked to each other.

SUMMARY OF THE INVENTION

The present invention provides for a protein cage polypeptide (or scaffolding protein) useful or capable of forming a hollow tetrahedral pyramid structure, wherein the protein cage polypeptide, or scaffolding protein, is capable of binding specifically to an antibody or part thereof, or any chimeric protein, molecule or compound comprising the antibody, or part thereof.

In some embodiments, the antibody is an IgG antibody. In some embodiments, the part of the antibody is an Fc region of an antibody, such as an IgG, IgA, IgD, IgE, or IgM antibody. In some embodiments, the antibody is a human, chicken, mice, rabbit, sheep, or goat antibody. In some embodiments, the antibody is a humanized antibody. In some embodiments, the IgG antibody is a human IgG antibody. In some embodiments, the antibody is part of a chimeric protein, molecule or compound, comprising the antibody, or part thereof. In some embodiments, the chimeric protein, or other molecule or compound, comprises an Fc region of an antibody. In some embodiments, the antibody, or part thereof, is covalently bonded to the chimeric protein, molecule or compound. In some embodiments, the binding affinity $K_a$ of the protein cage polypeptide, or scaffolding protein, to the antibody or part thereof, is equal to or more than $10^7$ $M^{-1}$, $10^8$ $M^{-1}$, or $10^9$ $M^{-1}$.

In some embodiments, the protein cage polypeptide comprises a polypeptide of from about 400 to about 700 amino acid residues. In some embodiments, the protein cage polypeptide comprises a polypeptide of from about 450 to about 650 amino acid residues.

In some embodiments, the protein cage polypeptide comprises an amino acid sequence having the following structure:

Polypeptide 1-AHL-Polypeptide 2-INSERT A-Polypeptide 3-INSERT B-Polypeptide 4 (Chemical Structure I);

wherein AHL is an "alpha helix linker", and INSERT A and/or INSERT B are each independently capable of specifically binding to an antibody or part thereof.

In some embodiments, the INSERT A has a length of about 17 to about 25 amino acids. In some embodiments, the INSERT B has a length of about 28 to about 85 amino acids. In some embodiments, the binding affinity $K_a$ of INSERT A and/or INSERT B to the antibody or part thereof, are each independently equal to or more than $10^7$ $M^{-1}$, $10^8$ $M^{-1}$, or $10^9$ $M^{-1}$. In some embodiments, the INSERT A and/or INSERT B each independently comprise the amino acid sequence DCAWHLGELVWCT (SEQ ID NO:41) or GCDCAWHLGELVWCTCG (SEQ ID NO:42).

In some embodiments, the protein cage polypeptide comprises an amino acid sequence having the following structure:

Polypeptide 1-AHL-Polypeptide 2-INSERT A-Polypeptide 3-INSERT B-Polypeptide 4 (Chemical Structure I);

wherein AHL is an "alpha helix linker", INSERT A having a length of about 17 to about 25 amino acids and comprising the amino acid sequence DCAWHLGELVWCT (SEQ ID NO:41) or GCDCAWHLGELVWCTCG (SEQ ID NO:42), and INSERT B having a length of about 28 to about 85 amino acids and comprising the amino acid sequence DCAWHLGELVWCT (SEQ ID NO:41) or GCDCAWHLGELVWCTCG (SEQ ID NO:42). SEQ ID NOs:41 and 42 are capable of binding to the Fc-region of IgG.

In some embodiments, Polypeptide 1 comprises an amino acid sequence comprising at least about 70%, 75%, 80%, 85%, 90%, 95%, 99%, or 100% amino acid identity to the amino acid sequence from the N-terminus to up to the AQEAQKQK sequence of any one of SEQ ID NO:1-40. In some embodiments, Polypeptide 1 comprises an amino acid sequence comprising the following: YGTAR, TDD, LXENLGTR, IDV, TGXRT, and/or SA; wherein X is any charged amino acid residue. In some embodiments, Polypeptide 1 comprises about 278 to about 303 amino acid residues.

In some embodiments, AHL comprises an amino acid sequence comprising: AQEAQKQK. In some embodiments, AHL comprises about 5, 6, 7, 8, 9, 10, or 11 amino acid residues.

In some embodiments, Polypeptide 2 comprises an amino acid sequence comprising at least about 70%, 75%, 80%, 85%, 90%, 95%, or 100% amino acid identity to the amino acid sequence from the C-end of the AQEAQKQK sequence to the N-end of INSERT A of any one of SEQ ID NO:1-40. In some embodiments, Polypeptide 2 comprises an amino acid sequence comprising the following: LTEVETYVLS (SEQ ID NO:43). In some embodiments, Polypeptide 2 comprises about 30 to about 36 amino acid residues. In some embodiments, Polypeptide 2 comprises about 33 amino acid residues.

In some embodiments, Polypeptide 3 comprises an amino acid sequence comprising at least about 70%, 75%, 80%, 85%, 90%, 95%, or 100% amino acid identity to the amino acid sequence from the C-end of INSERT A to the N-end of INSERT B of any one of SEQ ID NO:1-40. In some embodiments, Polypeptide 3 comprises an amino acid sequence comprising the following: FTLTVPSERGLQR (SEQ ID NO:44) and/or CATCEQIAD (SEQ ID NO:45). In some embodiments, Polypeptide 3 comprises about 110 to about 130 amino acid residues. In some embodiments, Polypeptide 3 comprises about 121 amino acid residues.

In some embodiments, Polypeptide 4 comprises an amino acid sequence comprising at least about 70%, 75%, 80%, 85%, 90%, 95%, or 100% amino acid identity to the amino acid sequence from the C-end of INSERT B of any one of SEQ ID NO:1-40. In some embodiments, Polypeptide 4 comprises an amino acid sequence comprising: EHHHHHH. In some embodiments, Polypeptide 4 comprises about 5 to about 13 amino acid residues. In some embodiments, Polypeptide 4 comprises about 8 amino acid residues.

In some embodiments, the protein cage polypeptide comprises an amino acid sequence comprises at least about 70%, 75%, 80%, 85%, 90%, 95%, 99%, or 100% amino acid identity to any one of SEQ ID NOs:1-40. In some embodiments, the protein cage polypeptide comprises an amino acid sequence comprising any one or more, or all, stretches of or individual amino acid residues indicated by an asterisk in FIG. 6. In some embodiments, the protein cage polypeptide comprises an amino acid sequence comprising any one or more, or all, charged amino acids stretches in the corresponding position(s) indicated by "#" in FIG. 6.

The present invention provides for a hollow tetrahedral pyramid structure comprising twelve protein cage polypeptides of the present invention assembled as the hollow tetrahedral pyramid structure, wherein the protein cage polypeptide is capable of binding to an antibody or part thereof. In some embodiments, the hollow tetrahedral pyramid structure encapsulates one or more smaller molecules of interest. In some embodiments, the smaller molecules of interest are therapeutic or detectable.

The present invention provides for a "self-assembling protein nanoparticle decorated with antibodies" (SAPNA) which is a chimeric protein assembly comprising: (a) one or more antibodies and (b) a protein cage polypeptide that provides a scaffold upon which to array the antibodies, wherein the one or more antibodies are bound to the INSERT A and/or INSERT B of the protein cage polypeptide.

The present invention provides for a SAPNA which is a chimeric protein assembly comprising: (a) one or more antibodies and (b) an engineered protein that provides a scaffold upon which to array the antibodies. The scaffolding protein forms hollow tetrahedral pyramids that can be assembled or disassembled based on buffer conditions. As the scaffold is hollow, the system can encapsulate smaller molecules of interest for release once the antibodies have localized the SAPNA to a target. These particles are engineered to modularly bind and display any IgG antibody (or Fc region only), such as a human or rabbit IgG antibody (or Fc region only), or fragment thereof, through a high-affinity interaction with the antibody Fc CH2/CH3 domains. The physically constrained localization of from 1, 2, 3, 4, 5, 6, 7, 8, 9, 10, 11, or 12 antibodies or Fc domains per nanoparticle allows activation of any oligomerization-dependent receptor-mediated pathways for which an antibody is available. In some embodiments, through separate loading and mixing, antibodies that recognize different epitopes can be loaded onto the same nanoparticle, conferring multi-functionality. In some embodiments, the nanoparticles can be used to stimulate innate or adaptive immune cells, as Fc receptor oligomerization is a necessary component of activation.

The present invention provides for a SAPNA structure comprising: (1) one protein cage polypeptide or scaffolding protein (or engineered protein cage protein (PC)), or a plurality of protein cage polypeptides or scaffolding proteins (or engineered protein cage proteins (PCs)) assembled into a 3-dimensional assembly, such as a tetrahedral pyramid, (2) optionally one or more human or rabbit IgG antibodies, (3) optionally an IgG binding loop, and (4) optionally, when the plurality of polypeptides or scaffolding proteins (or engineered protein cage proteins (PCs)) are assembled into a 3-dimensional assembly with antibodies, a cargo of interest, such as a compound or molecule, such as a macromolecule, confined or enclosed by the 3-dimensional assembly. One embodiment of the invention is shown in FIG. 1A.

The human IgG antibodies recognize and bind tightly to a variety of targets. In some embodiments, the targets are parts of pathogens. In some embodiments, the targets are native cellular components. In some embodiments, the IgG binding loop is a sequence of protein that is incorporating into the PC and serves as a connection between the antibody and the PC. The PC has had several publications devoted to it (1-3), however never with any context related to antibodies. Under most physiological conditions the PC component can self-assemble into a hollow tetrahedral pyramid from 12 copies of itself. In some embodiments, the SAPNA structure is capable of delivering or carrying cargo to wherever the SAPNA is localized by the antibodies. In some embodiments, the cargo size ranges between about 150 kDa and about 20 kDa. Many useful macromolecules fit this range.

SAPNA structures can be assembled and disassembled. This functionality can be used to initially capture cargo or release cargo. In addition, since there are many kinds of antibodies. PCs with a variety of antibodies can be mixed to create a SAPNA with a diverse set of antibodies on its surface. The capacity to interchange antibodies provides additional functionality.

In some embodiments, aside from a capacity to carry and localize cargo, SAPNAs can alter cellular behavior without cargo. External stimuli that affect cells often start from a ligand binding to bring transmembrane receptors into close contact (oligomerization) (4). This is achieved through the binding of two or more receptors to a ligand, such as a cytokine, however the ligands for many receptors are unknown, or could be restricted to the cell surface of another cell. In some embodiments, through display on the PC (FIG. 1A, B; FIG. 7), the functional power of any IgG antibody developed against any single receptor would be significantly enhanced. Instead of largely being limited to blocking the receptor, the antibody could activate the intracellular signaling pathway, resulting in much finer control of cellular activity. In some embodiments, different kinds of antibodies are displayed on the PC and the protein can influence signals that operate through multi-chain immune recognition receptors (MIRRs). Many immune cells rely on MIRRs for control of intracellular signaling (4). MIRRs often require multi-chain engagement by an extracellular ligand for oligomerization and subsequent activation. In some embodiments, the SAPNAs would modularly confer activation/signaling abilities to IgG antibodies that are currently limited to blocking mechanisms. This could open entirely new therapeutic avenues for existent and newly developed human IgG antibodies against any disease where modulation of cell signaling is desired.

SAPNAs have a huge potential, as their use would not be limited to a single, or few diseases. Their potential is also not fixed, as the number of monoclonal antibody products developed increases, so does the potential uses for the SAPNAs. In some embodiments, the SAPNA structure is used to target cancer in immunotherapy, as there are well-defined ligand-receptor interactions that can be modulated, along with several therapeutic IgG antibodies available (such as, anti-PD-1/PD-L1, anti-CTLA4). For a list of therapeutic antibodies, their origin and isotype, method of action, and licensed indication see reference (6). Additionally, cancer immunology is a research field largely based on the use of antibody-staining based flow cytometry, which would allow for extensive pre-clinical candidates to test. The present invention provides for a nucleic acid encoding the protein cage polypeptide of the present invention. In some embodiments, the nucleic acid is polynucleotide. In some embodiments, the nucleic acid is vector, such as an expression vector. In some embodiments, the nucleic acid encoding the protein cage polypeptide is operatively linked to a promoter capable of expressing the protein cage polypeptide in a host cell. In some embodiments, the nucleic acid is a vector capable of stable introduction into and/or maintenance in the host cell.

The present invention provides for a host cell comprising the nucleic acid encoding the protein cage polypeptide of the present invention. In some embodiments, the nucleic acid is a vector capable of stable introduction into and/or maintenance in the host cell.

The present invention provides for a composition comprising the protein cage polypeptide (or scaffolding protein) or hollow tetrahedral pyramid structure of the present invention, wherein the protein cage polypeptide (or scaffolding protein) or hollow tetrahedral pyramid structure is binding specifically to an antibody or part thereof, or any chimeric protein, molecule or compound comprising the antibody, or part thereof.

The present invention provides for a method for producing the protein cage polypeptide, comprising: (a) providing a host cell of the present invention, (b) culturing the host cell under a suitable condition wherein the protein cage polypeptide is expressed, and (c) optionally recovering the protein cage polypeptide.

The present invention provides for a method for detecting or isolating a pathogenic biological agent, or part thereof, the method comprising: (a) providing a "self-assembling protein nanoparticle decorated with antibody" (SAPNA) wherein the antibody is capable of binding specifically to a pathogenic biological agent, or part thereof; (b) contacting the SAPNA with a sample comprising the pathogenic biological agent, or part thereof, such that the SAPNA binds the pathogenic biological agent, or part thereof; (c) detecting the SAPNA pathogenic biological agent, or part thereof via detection, and/or separating the SAPNA bound pathogenic biological agent, or part thereof, from the rest of the sample; and (d) determining the abundance of the pathogenic biological agent, or part thereof.

In some embodiments, the method further comprises: obtaining a sample from a subject suffering from, diagnosed with, or suspected to be suffering from a disease caused by a pathogenic biological agent. In some embodiments, the subject is a human. In some embodiments, the subject is a mammal or bird. In some embodiments, the subject is a common pet or livestock animal. In some embodiments, method further comprises: treating the subject for the disease, such as administering a therapeutically effective dose of a medication to the subject known or capable of curing or alleviating the effects of the disease.

The present invention provides for a SAPNA that is chemically conjugated with one or more chemical compounds, such as one or more drugs, and then targeted to biological/cellular sites for drug deposition in an analogous fashion to antibody-drug conjugates (ADCs),

BRIEF DESCRIPTION OF THE DRAWINGS

The foregoing aspects and others will be readily appreciated by the skilled artisan from the following description of illustrative embodiments when read in conjunction with the accompanying drawings.

FIG. 6. Conserved SAPNA sequence (SEQ ID NO:40). Legend: 284 residues conserved/maintained (284/456=62%); "*"=conserved oligomerization interface residues and highly conserved residues based on evolution (multiple sequence alignments); also includes residues that were determined not to tolerate insertions/deletions. This includes residues on either side of attempted insertion (bolded *); "$"=insertions allowed and tolerated between these residues; "A"=deletions allowed with replacement insertions of varying lengths (First site: 17 to 25 residues in length and must include DCAWHLGELVWCT (SEQ ID NO:41) or GCDCAWHLGELVWCTCG (SEQ ID NO:42) and Second site: 28 to 85 residues in length and must include DCAWHLGELVWCT (SEQ ID NO:41) or GCDCAWHLGELVWCTCG (SEQ ID NO:42)); "#"=point mutation, such as single charge swap mutations from negative to positive allowed; "@"=alpha-helix linking two domains that could tolerate length adjustment; " "=blank space above residue means non-conserved, can be any amino acid.

DETAILED DESCRIPTION OF THE INVENTION

Figure 1A:
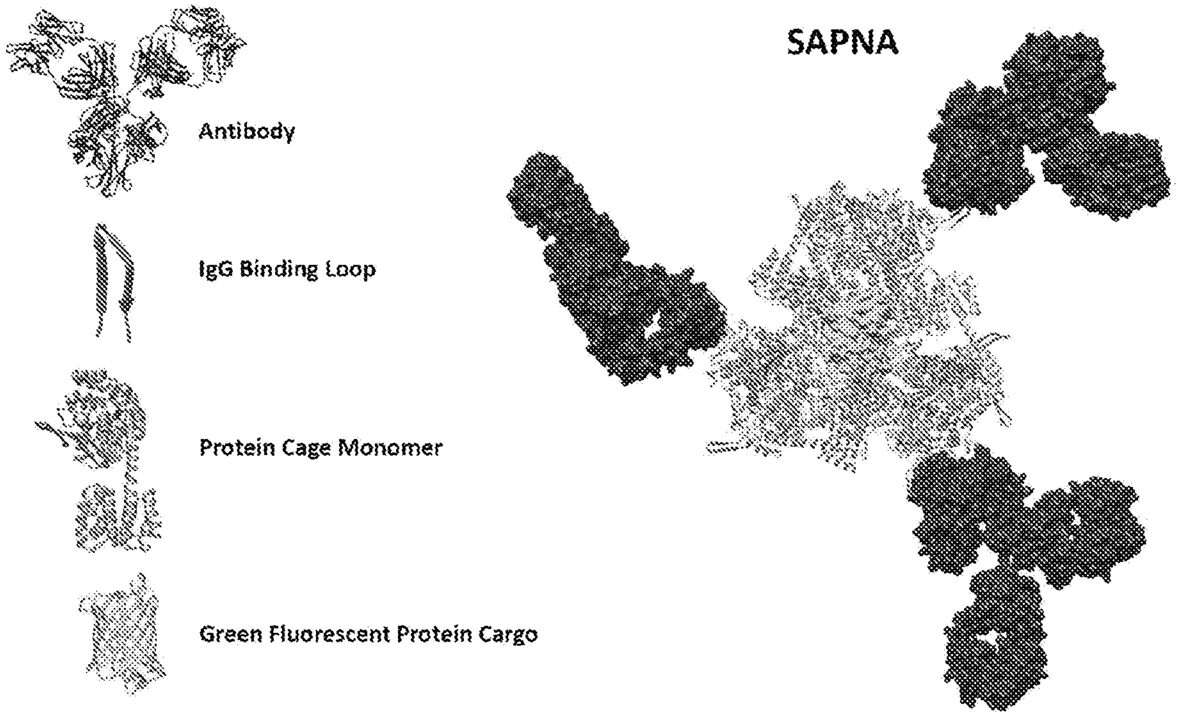
FIG. 1A. A SAPNA model and parts thereof.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

As used in the specification and the appended claims, the singular forms "a," "an," and "the" include plural referents unless the context clearly dictates otherwise. Thus, for example, reference to a "polypeptide" includes a polypeptide molecule as well as a plurality of polypeptides of s specific amino acid sequence.

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

The term "about" refers to a value including 10% more than the stated value and 10% less than the stated value.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The terms "host cell" is used herein to refer to a living biological cell that can be transformed via insertion of an expression vector.

The terms "expression vector" or "vector" refer to a compound and/or composition that transduces, transforms, or infects a host cell, thereby causing the cell to express nucleic acids and/or proteins other than those native to the cell, or in a manner not native to the cell. An "expression vector" contains a sequence of nucleic acids (ordinarily RNA or DNA) to be expressed by the host cell. Optionally, the expression vector also comprises materials to aid in achieving entry of the nucleic acid into the host cell, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host cell and replicated therein. Particular expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The terms "polynucleotide" and "nucleic acid" are used interchangeably and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); positive backbones; non-ionic backbones, and non-ribose backbones. Thus, nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The term "promoter," as used herein, refers to a polynucleotide sequence capable of driving transcription of a DNA sequence in a cell. Thus, promoters used in the polynucleotide constructs of the invention include cis- and trans-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. Promoters are located 5' to the transcribed gene, and as used herein, include the sequence 5' from the translation start codon (i.e., including the 5' untranslated region of the mRNA, typically comprising 100-200 bp). Most often the core promoter sequences lie within 1-2 kb of the translation start site, more often within 1 kbp and often within 500 bp of the translation start site. By convention, the promoter sequence is usually provided as the sequence on the coding strand of the gene it controls. In the context of this application, a promoter is typically referred to by the name of the gene for which it naturally regulates expression. A promoter used in an expression construct of the invention is referred to by the name of the gene. Reference to a promoter by name includes a wildtype, native promoter as well as variants of the promoter that retain the ability to induce expression. Reference to a promoter by name is not restricted to a particular species, but also encompasses a promoter from a corresponding gene in other species.

The term "operatively linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "cell" or "cells" refers to any cells of any organism, ranging from single celled organisms to mammalian cells, in vitro or in vivo.

One can modify the expression of a nucleic acid encoding any protein cage polypeptide taught herein by a variety of methods in accordance with the methods of the invention. Those skilled in the art would recognize that increasing gene copy number, ribosome binding site strength, promoter strength, and various transcriptional regulators can be employed to alter a protein expression level.

The present invention can be used for a variety of purposes (which as described can be used in a research context as a tool, or a clinical setting as a therapeutic): In some embodiments, the SAPNA structure is a therapeutic or research tool capable of modulating the immune system by binding/blocking cell-surface and soluble receptor/ligands in humans or research models. In some embodiments, the SAPNA structure is capable of activating one or more internal cellular pathways through enforcing external cell-surface receptor/ligand oligomerization. In some embodiments, the SAPNA structure is labeled, such as with a fluorescent dye or label, and can be used to visualize cell-surface targeting antibodies, such as in immunofluorescence or flow cytometry. In some embodiments, the fluorescent dye is an Alexa Fluor® fluorescent dye. In some embodiments, the SAPNA structure is a tool to test/screen the feasibility of using any combination of human/rabbit IgG antibodies to effect a cellular change or physiological response in a living organism. In some embodiments, the SAPNA structure is useful for opsonization of circulating and invading particles in vivo. In some embodiments, the SAPNA structure is capable of targeting and manipulating viruses/viral particles in an aqueous or semi-aqueous environment. In some embodiments, the SAPNA structure is capable of encapsulating a cargo, with subsequent targeting to cell-surfaces. In some embodiments, the SAPNA structure is capable of gaining access to an internal cellular environment through endocytosis, with or without cargo (initiation and modulation of endocytosis). In some embodiments, the SAPNA structure is a vaccine or vaccine adjuvant. In some embodiments, the SAPNA structure is an in vitro immune cell activation tool. In some embodiments, the SAPNA structure is a biodegradable aesthetic product that binds fluorescent proteins to keratin in hair and skin through displaying an anti-fluorescent antibody and anti-keratin antibody on the same scaffold. In some embodiments, the SAPNA molecule loaded with antibodies can positively or negatively select cellular populations from a mixed pool of cells.

There are no clinical equivalents to the present invention. There is another group working on engineering ferritin (7), however due to the spacing of the ferritin molecules, the antibody occupancy would be much less predictable, and therefore a poorer nanocage for immunological modulation through antibody display. It is likely a better carrier of small molecules due to the larger pores in the SAPNA nanocages that we are engineering. This group also appears to be more focused on using ferritin cages to deliver cargo into cells (8, 9). Two different, yet competing types of technologies are antibodies with engineered Fc regions and bispecific antibodies.

Many antibodies fail clinical trials (10), which has led to research into enhancing antibody dependent cell mediated cytotoxicity (ADCC). However, these efforts are largely aimed at enhancing Fc-gamma receptor binding to antibody Fc regions through Fc mutations. The SAPNA nanocages would be superior to these methods, as ADCC requires Fc-gamma receptor aggregation through Fc binding, which the SAPNAs would physically enforce. Additionally, the SAPNAs could take advantage of these efforts, and in fact be loaded with the mutated Fcs to further augment therapeutic efficacy.

Bi-/multi-specific antibodies (11-15), which are essentially antibodies that contain two or more different antigen recognition regions, are connected in a variety of ways (14, 15). While bi-/multi-specific antibodies have great potential, each one must be individually designed, tested, and optimized, compared to the SAPNA, which would be modular and available for use by almost any commercially available IgG antibody. A major advantage possessed by the SAPNAs, is that other non-antibody molecules can be displayed at the same time as the antibodies. Pre-formulating mixtures of different antibodies and subsequent addition of unloaded SAPNA cages, would allow for loading of several (~2-12) different antibodies onto the same nanocage. This can then act as a large multi-specific nanoparticle, which is a great advantage over the current multi-specific antibodies. The modular nature and multi-functionality of the SAPNAs are highly desirable characteristics in next-generation biological therapeutics.

In some embodiments, the protein cage polypeptide (or scaffolding protein) is binding specifically to the antibody or part thereof, or any chimeric protein, molecule or compound comprising the antibody, or part thereof; wherein the antibody or part thereof is binding specifically to a pathogenic biological agent, or part thereof.

In some embodiments, the tetrahedral pyramid structure is binding specifically to the antibody or part thereof, or any chimeric protein, molecule or compound comprising the antibody, or part thereof; wherein the antibody or part thereof is binding specifically to a pathogenic biological agent, or part thereof.

In some embodiments, the SAPNA molecule can be used as a multi-valent detection platform for pathogenic biological agents, including, but not limited to, viruses, bacteria, and misfolded proteins implicated in any human/mammalian diseases (such as prions and other amyloids), by loading the SAPNA molecule with one or more antibodies against antigenic proteins or other surface molecules specific to those agents. Detection applications extend to isolation and determination of abundance (i.e. infection severity) for the pathogenic agents. As previously noted, for purposes of analysis, the SAPNA molecule can be covalently labeled with a molecule such as a fluorophore for detection, while the multi-valent His-tags (up to 12 copies) can be used to manipulate and isolate various antigen-bound fractions. In addition to humans, the pathogenic agents to be analyzed extend to those affecting animals that are of interest to human health and welfare (e.g. common pets, livestock, etc.) In some embodiments, the common pet is a dog, cat, rabbit, guinea pig, hamster, mouse, or the like. In some embodiments, the livestock is a mammal, such as cattle, horse, pig, sheep, or goat, or a bird, such a chicken, duck, or goose.

The surfaces of viruses and bacteria are coated or decorated with proteins or other molecules that are necessary for their biological functions, including for host cell attachment and host entry, and for survival under harsh conditions. Owing to their importance to propagation, such molecules, or parts of those molecules, tend to be conserved for a given species or strain of virus or bacterium. As a result, such molecules can serve as robust targets for identification. Such molecules are furthermore specific and distinct for different viruses and bacteria, and are therefore suitable for specific assignment of identity in diagnostic applications. The ability to recognize specific viruses and bacteria by antibody binding to their surface molecules, or sometimes to molecules produced by their lysis, is understood and widely applied in practice. In some embodiments, the SAPNA molecules provide distinct and advantageous features for identifying and isolating viruses and bacteria owing to the polyvalent and modular capacity of SAPNA to display selected antibodies conferring specific recognition profiles for binding, and their support of chemical features for isolation and reporter readout, for example by fluorescence.

Different embodiments of the invention may present more than one distinct type of antibody on the SAPNA molecule. For example, a SAPNA molecule can simultaneously present antibodies specific for different strains or subtypes of one type of virus or bacterium. This would provide for facile and efficacious identification of viruses with known variants or subtypes in a population. The influenza virus is a well-understood example. This would obviate the need to design different reagents for the detection of variant strains of a virus. Presentation of more than one type of antibody could furthermore provide a valuable advantage in discriminating between pathogens (e.g. different bacteria) that express partially overlapping sets of surface antigens. As an example, if bacterium A expresses surface proteins X and Y, and bacterium B expressed proteins Y and Z, and bacterium C expresses proteins X and Z, then a SAPNA molecule presenting antigens directed against proteins Y and Z will, by avidity effects, preferentially identify bacterium B. Of course, other scenarios for preferential detection of combinations of surface antigens will be possible, which is true for both bacteria and viruses.

Different embodiments of the invention may have different numbers of a single type of antibody presented on the SAPNA molecule, achieved by addition of antibodies in different stoichiometric amounts relative to the SAPNA core. Because the degree of polyvalency in molecular binding is understood to strongly affect binding avidity, the ability to tailor the number of antibodies presented on a SAPNA molecule can confer valuable control over final binding affinity (i.e. tunability). Such control provides value in creating a reagent with the most desirable window of detection for positive binding of intended target molecules, while still giving negative binding readout for non-cognate molecules that may be similar in different degrees to the intended detection target. A narrow range of affinity versus target specificity is a common challenge for previous mono-valent or low-valent reagents used for bacterial target identification.

Different embodiments of the invention will be specific for different viral, bacterial, and amyloid marker proteins. The possible target list is expansive, continually growing with the discovery of new pathogens, and requires only that specific antibodies are known or can be established for the marker protein of interest (a capability routinely demonstrated in industry today). Among viruses of medical urgency, the spike (S) proteins of various coronaviruses, including SARS-CoV, SARS-CoV-2, and MERS-CoV, would be example targets for identification. The gp120 glycoprotein is an example identification target for the HIV virus. The GP surface protein is an example target for Ebola virus. The hemagglutinin (HA) protein is an example target for the influenza virus, with different viral subtypes identifiable by different I-IA variants. For bacterial targets, example embodiments would be directed against diverse surface proteins and polysaccharide molecules. Specific examples of value in human pathogenesis would include SAPNA molecules bearing antibodies to capsular polysaccharides (CPS) from *Haemophilus* influenza type b (Nib) or group B *Streptococcus*, or any number of other pathogens with capsular polysaccharide coats. Further examples would be SAPNA molecules with antibodies to: the outer surface protein (OspA) of the causative agent of Lyne disease (*Borrelia burgdorferi* or related species), the poly D-glutamic acid capsule antigen of *Bacillus anthracis*, or the heparin binding antigen (NHBA) of *Neisseria gonorrhea*. Prion and other amyloid diseases are often neurodegenerative, and can affect both humans and animals. In these pathologies, otherwise natural proteins misfold and then aggregate to form cytotoxic amyloid aggregates, which can distribute systemically, accumulate in diverse organ systems, and lead to disease. Of relevance to this embodiment of the invention, the unfolded/aggregated toxic forms of prion/amyloid proteins have conformations different from the natively folded forms of the proteins, making the toxic forms of these pathogenic agents distinguishable by antibodies. Examples of prion diseases, whose pathogenic proteins could be detected using SAPNA molecules, are Creutzfeldt-Jokob Disease in humans and Bovine Spongiform Encephalopathy ("Mad Cow Disease") in cows. Detection of pathogenic proteins would extend to other amyloid proteins: A-beta (involved in Alzheimers disease), tau protein (involved in diverse tauopathies), alpha-synuclein (involved in Parkinson's disease), transthyretic (involved in systemic amyloidosis), and others. These represent only selected examples.

REFERENCES CITED

1. Y. T. Lai et al., Designing and defining dynamic protein cage nanoassemblies in solution. Sci Adv 2, e1501855 (2016).
2. Y. T. Lai, K. L. Tsai, M. R. Sawaya, F. J. Asturias, T. O. Yeates, Structure and flexibility of nanoscale protein cages designed by symmetric self-assembly. J. Am. Chem. Soc. 135, 7738-7743 (2013).
3. J. E. Padilla, C. Colovos, T. O. Yeates, Nanohedra: using symmetry to design self assembling protein cages, layers, crystals, and filaments. Proc. Natl. Acad. Sci. U.S.A 98, 2217-2221 (2001).
4. A. B. Sigalov, The SCHOOL of nature: I. Transmembrane signaling. Self Nonself 1, 4-39 (2010).
5. D. M. Ecker, S. D. Jones, H. L. Levine, The therapeutic monoclonal antibody market. MAbs 7, 9-14 (2015).
6. M. Suzuki, C. Kato, A. Kato, Therapeutic antibodies: their mechanisms of action and the pathological findings they induce in toxicity studies. J Toxicol Pathol 28, 133-139 (2015).
7. H. J. Kang et al., Developing an antibody-binding protein cage as a molecular recognition drug modular nanoplatform. Biomaterials 33, 5423-5430 (2012).
8. W. Choe, T. A. Durgannavar, S. J. Chung, Fc-Binding Ligands of Immunoglobulin G: An Overview of High Affinity Proteins and Peptides. Materials (Basel) 9, (2016).
9. Y. J. Kang et al., Polyvalent display of monosaccharides on ferritin protein cage nanoparticles for the recognition and binding of cell-surface lectins. Macromol. Biosci. 14, 619-625 (2014).
10. G. A. Lazar et al., Engineered antibody Fc variants with enhanced effector function. Proc. Natl. Acad. Sci. U.S.A 103, 4005-4010 (2006).
11. D. W. LaFleur et al., Monoclonal antibody therapeutics with up to five specificities: functional enhancement through fusion of target-specific peptides. MAbs 5, 208-218 (2013).
12. N. Dimasi et al., Development of a Trispecific Antibody Designed to Simultaneously and Efficiently Target Three Different Antigens on Tumor Cells. Mol. Pharm. 12, 3490-3501 (2015).
13. J. Stieglmaier, J. Benjamin, D. Nagorsen, Utilizing the BiTE (bispecific T-cell engager) platform for immunotherapy of cancer. Expert Opin Biol Ther 15, 1093-1099 (2015).
14. C. Spiess, Q. Zhai, P. J. Carter, Alternative molecular formats and therapeutic applications for bispecific antibodies. Mol. Immunol. 67, 95-106 (2015).
15. H. Byrne, P. J. Conroy, J. C. Whisstock, R. J. O'Kennedy, A tale of two specificities: bispecific antibodies for therapeutic and diagnostic applications. Trends Biotechnol. 31, 621-632 (2013).

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

Materials and Methods

Design of self-assembling protein nanoparticles decorated with antibodies (SAPNA). The workflow for SAPNA was an iterative process of: engineer a set of DNA constructs, attempt to express protein, and if protein expressed, characterize said construct and test it for human Fc (hFc) binding. Site-directed mutagenesis was used to incorporate synthesized DNA fragments into the template scaffold (cloned into the pET22b+ vector), and make subsequent mutations to any new constructs. The scaffold template, a self-assembling tetrahedral protein cage, originated from work in the Yeates lab of UCLA (1-3). Through recent collaboration, the unique capabilities of the high-throughput small-angle X-ray scattering (HT-SAXS) beamline developed by our group, was used to structurally characterize two scaffold variants under varying salt and pH conditions in solution (4). These two scaffold variants were used as templates for further functional engineering. We aimed to functionalize the scaffold to display antibodies with many possible uses in mind (see above). Through viewing of the available structures of the template scaffold and multiple sequence alignments of evolutionarily-related homologs, we identified potential sites for mutagenesis. Upon sequencing verification of correct sequence, constructs were expressed and purified in parallel. The following buffers were used in the purification: 1. Lysis (50 mM Tris pH 8.0, 300 mM NaCl, 10 mM Imidazole), 2. Wash (50 mM Tris pH 8.0, 300 mM NaCl, 100 mM Imidazole), 3. Elution (50 mM Tris pH 8.0, 300 mM NaCl, 300 mM Imidazole), 4. Gel Filtration (20 mM Tris pH 7.4 or 8.0, 100 mM NaCl, OR PBS pH 7.4, OR PBS pH 7.4, 0.05% Triton-X100). Upon elution of the His-tagged proteins from Ni-NTA beads, the concentration was measured via absorbance and theoretical extinction coefficients. Due to the high valency of the constructs (12 monomers, each with a His-tag), the increased affinity for the Ni-NTA beads resulted in relatively pure fractions. Therefore, any appreciable concentration of protein above baseline was predicted to be properly- to semi-folded mutant scaffold. Those constructs that resulted in said protein, were further purified by size exclusion chromatography (SEC), and tested in peak-shift assays for hFc binding. This mutagenesis process was repeated until configurations were found that bound hFc without forming an appreciable amount of scaffold oligomers (Table 2). A set of the most optimal configurations were further characterized via the structural technique size exclusion chromatography small-angle X-ray scattering coupled to multi-angle light scattering (SEC-SAXS-MALS).

Relevant Research

The original small peptide motif engineered to bind the Fc region of IgG antibodies was first described in 2000, termed Fc-III (5). The motif was discovered through the use of peptide phage display, which is an iterative way of selecting for macromolecular binding interactions. Fc-III was further enhanced through the addition of stabilizing amino acids in a cyclic peptide form called Fc-III-4C (6). In 2012, the Fc-III peptide was incorporated into the loop of a ferritin protein cage and the ability to bind and target antibodies was demonstrated (7). This ferritin protein cage looks to have been disclosed (WO2013055058A9). As described below, we engineered the Fc-III and Fc-III-4C sequences into several sites in the previously mentioned scaffold template, which we demonstrate can reproducibly bind and display human and rabbit IgG antibodies in solution.

Results

Figure 1B:
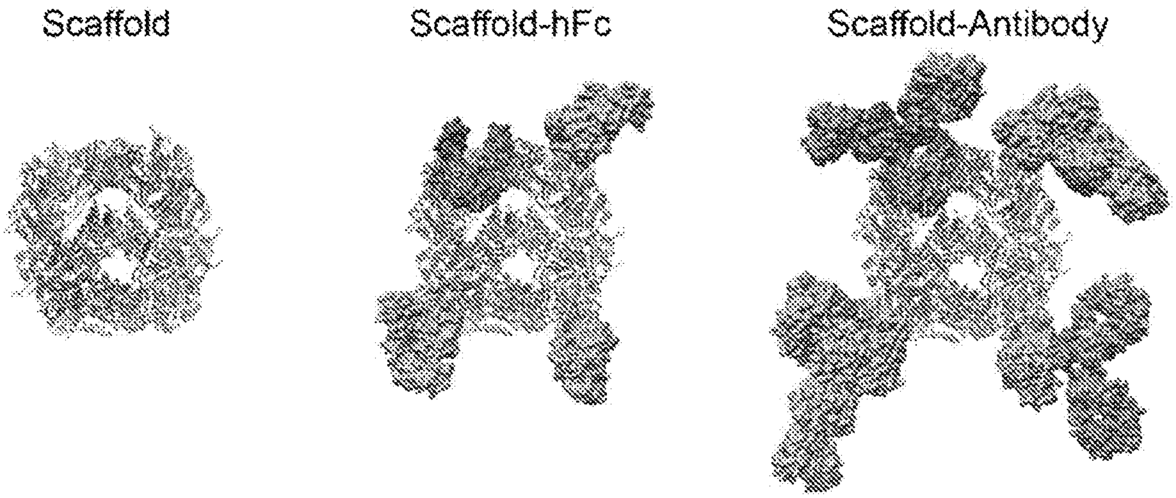
FIG. 1B. Models of predicted structures of various scaffold states.
Figure 2A:
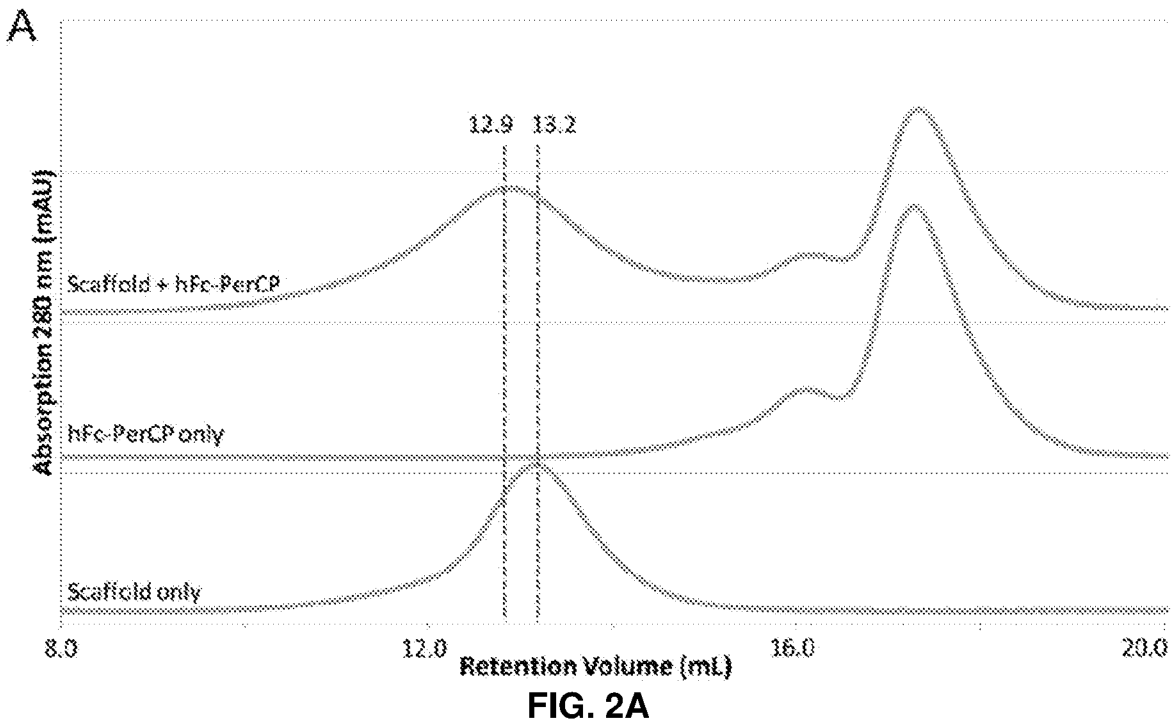
FIG. 2A. SEC peak shift binding assays of a scaffold with the PerCP-labeled human IgG1 Fc domain. Absorbance at 280 nm.
Figure 2B:
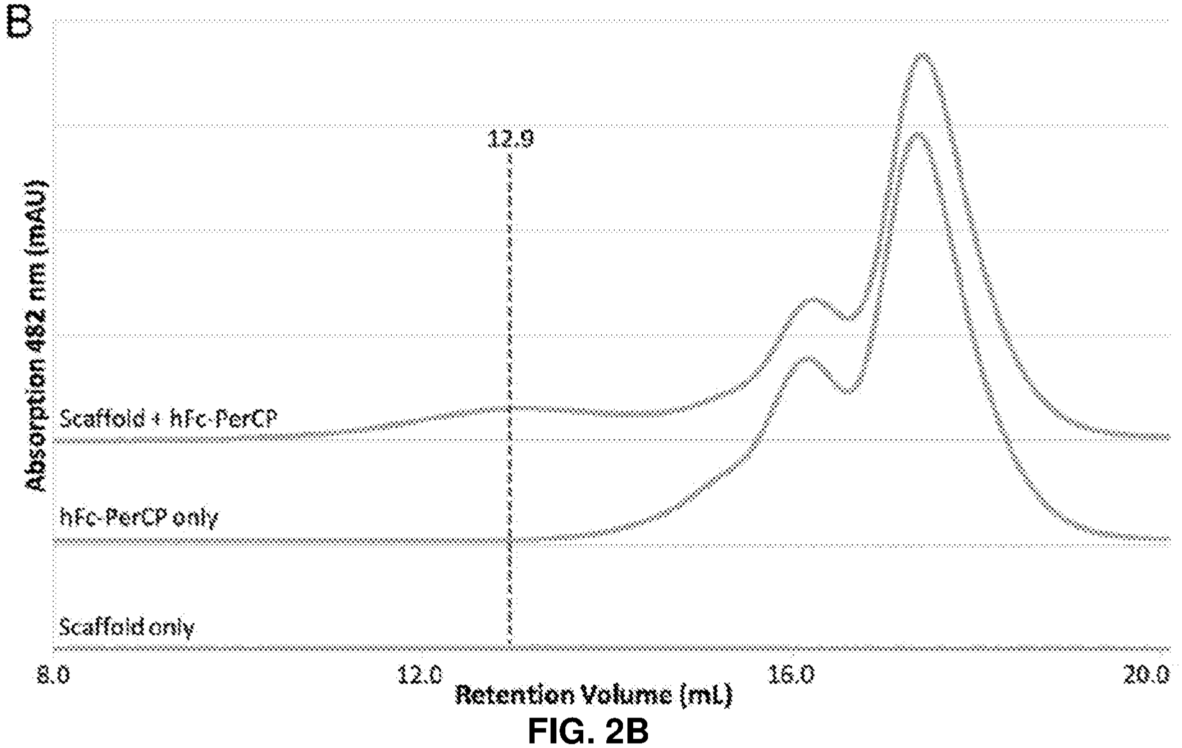
FIG. 2B. SEC peak shift binding assays of a scaffold with the PerCP-labeled human IgG1 Fc domain. Absorbance at 482 nm.
Figure 3A:
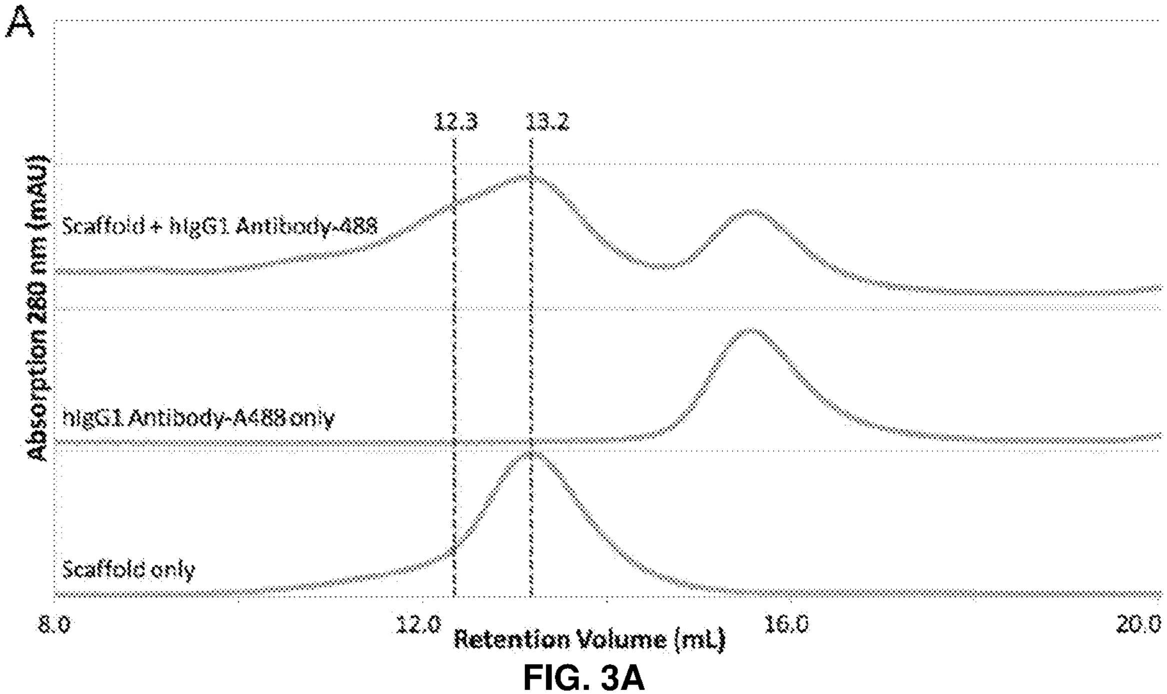
FIG. 3A. SEC peak shift binding assays of a scaffold with an Alexa Fluor®-488-labeled human IgG1 isotype antibody. Absorbance at 280 nm. Alexa Fluor® is a registered trademark owned by Thermo Fisher Scientific (Waltham, MA).
Figure 3B:
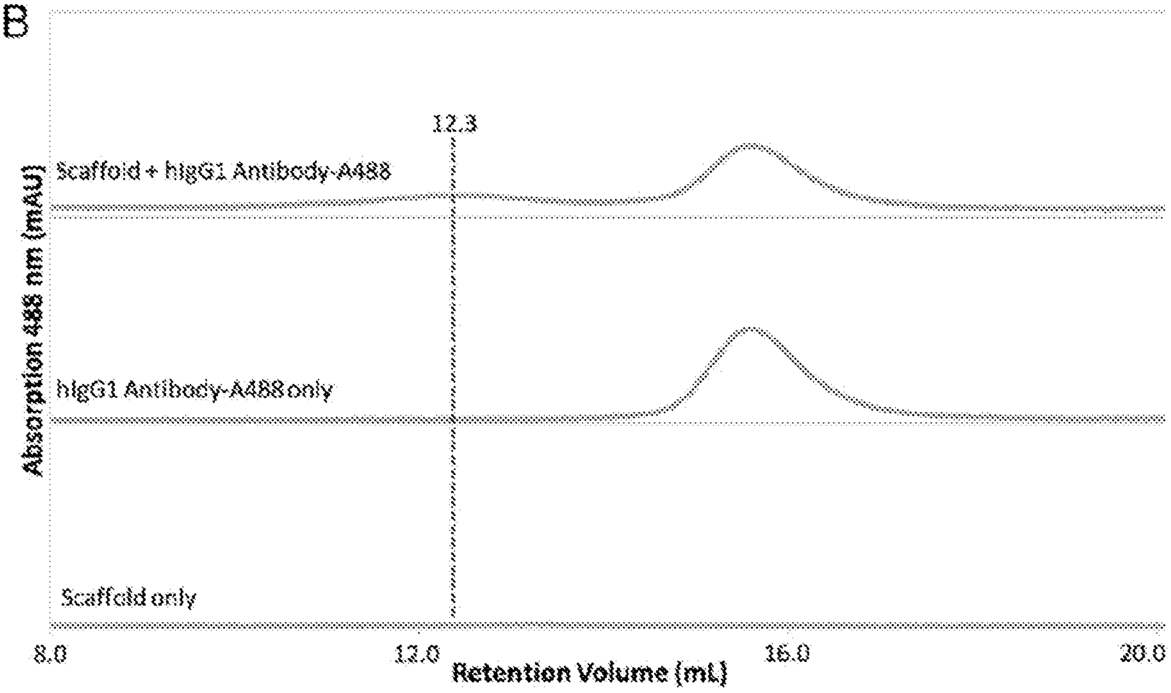
FIG. 3B. SEC peak shift binding assays of a scaffold with an Alexa Fluor®-488-labeled human IgG1 isotype antibody. Absorbance at 488 nm.

We successfully engineered the self-assembling protein-based scaffold to bind and display antibodies. The SAPNA structures in FIG. 1 are representative models of predicted structures that the dynamic system can sample in solution when binding human or rabbit IgG Fc domains or antibodies. To biochemically demonstrate the antibody/Fc binding abilities of our scaffold molecules, human IgG1 Fc conjugated to the fluorescent protein, PerCP (Fc-PerCP), was added to a scaffold and run on SEC (FIGS. 2A and 2B). The peak absorbance at 280 nm (A280) which is a readout for protein (FIG. 2A), is shifted from retention volume 13.2 mL to 12.9 mL, showing an increase in size of the scaffold. Additionally, a peak absorbance at 482 nm (A482) which is a readout for the fluorescence from PerCP, appears at 12.9 mL, supporting that the increase in size of the scaffold is due to binding of Fc-PerCP. Similarly, a peak shift assay with an Alexa Fluor®-488 labeled human IgG1 isotype antibody (hIgG1 Antibody-488) was done with a scaffold (FIGS. 3A and 3B). The A280 peak (FIG. 3A), is shifted from retention volume 13.2 mL to 12.3 mL, showing an increase in size of the scaffold. An absorbance 488 (A488) peak which is a readout for the fluorescence from the Alexa Fluor®-488 fluorescent dye, appears at 12.3 mL, supporting that the increase in size of the scaffold is due to binding of hIgG1 Antibody-488. It should be noted that we have evidence to suggest that chemical conjugation of fluorophores and fluorescent proteins (likely through the widely-used primary amine method) to the antibodies/Fcs, may reduce the ability of antibodies/Fcs to bind the functionalized scaffold. Due to this we do not expect large A482 and A488 peaks in FIG. 2B and FIG. 3B, which these data reflect.

Figure 4A:
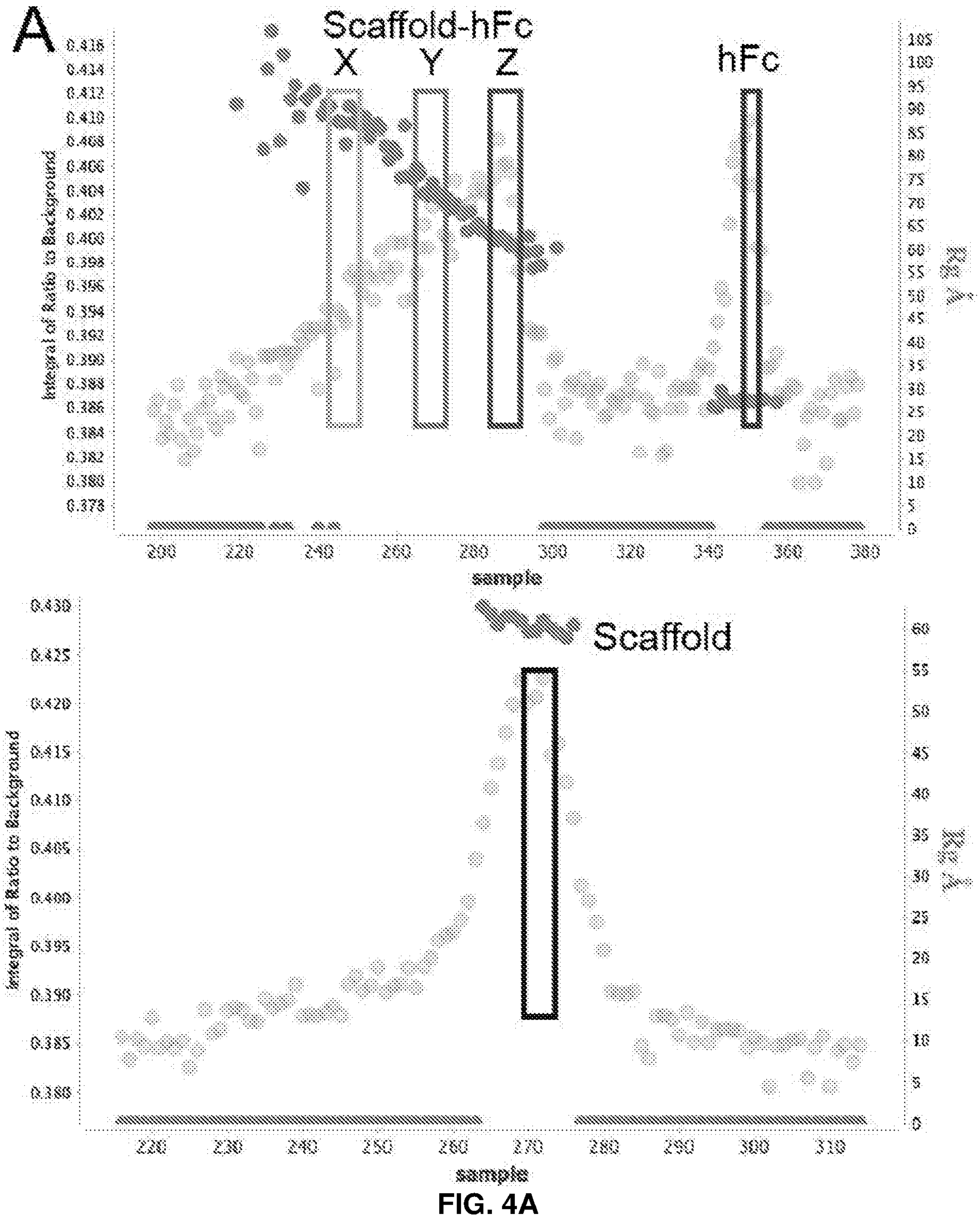
FIG. 4A. SEC SAXS of a scaffold with human IgG1 Fc domain. Sample trace from SEC-SAXS-MALS.
Figure 4B:
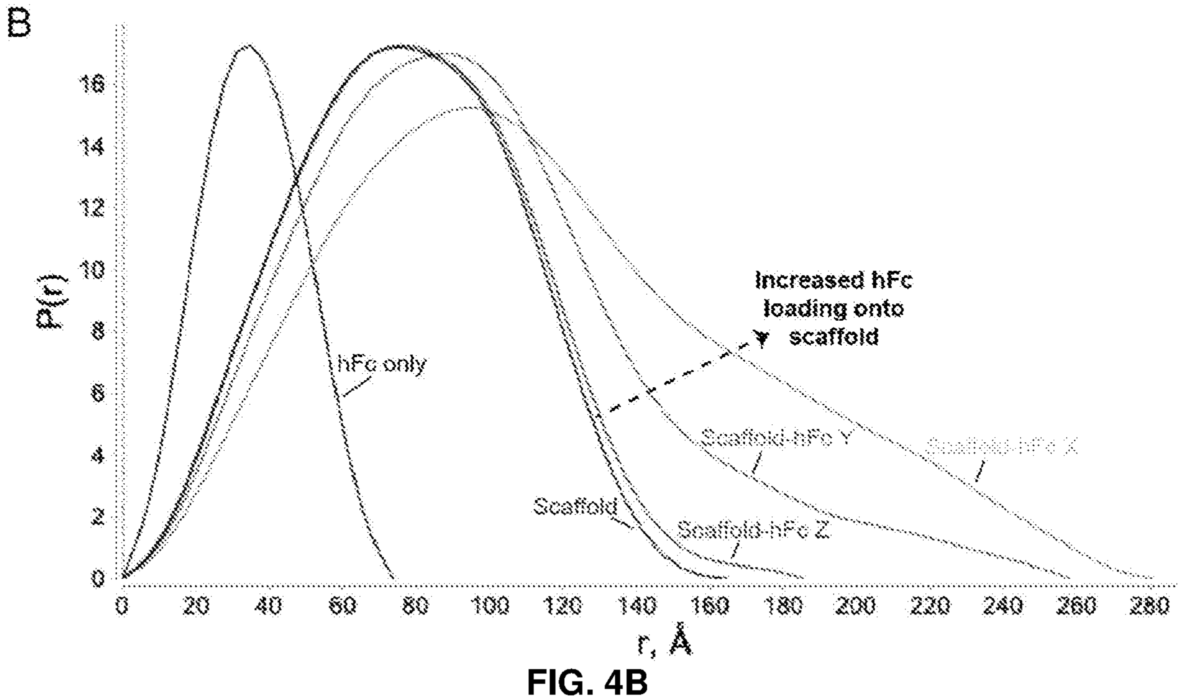
FIG. 4B. SEC SAXS of a scaffold with human IgG1 Fc domain. P(r) function histograms.
Figure 5A:
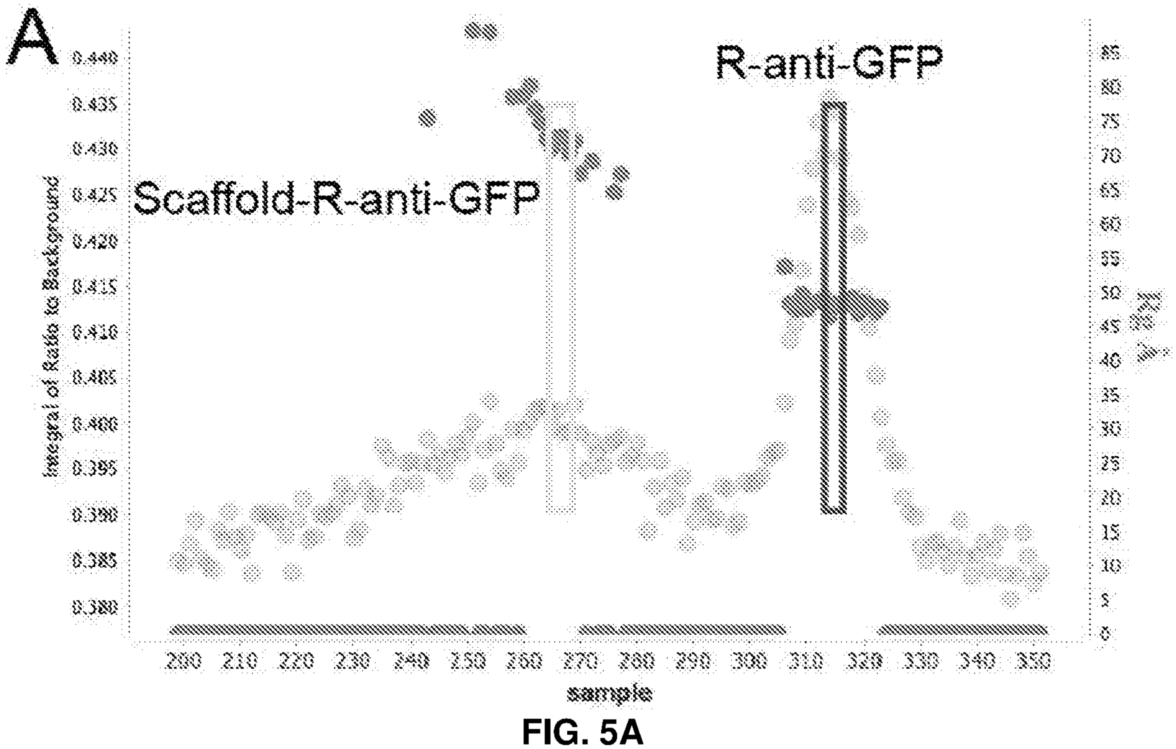
FIG. 5A. SEC SAXS of a scaffold with a rabbit anti-GFP antibody. Sample trace from SEC-SAXS-MALS.
Figure 5B:
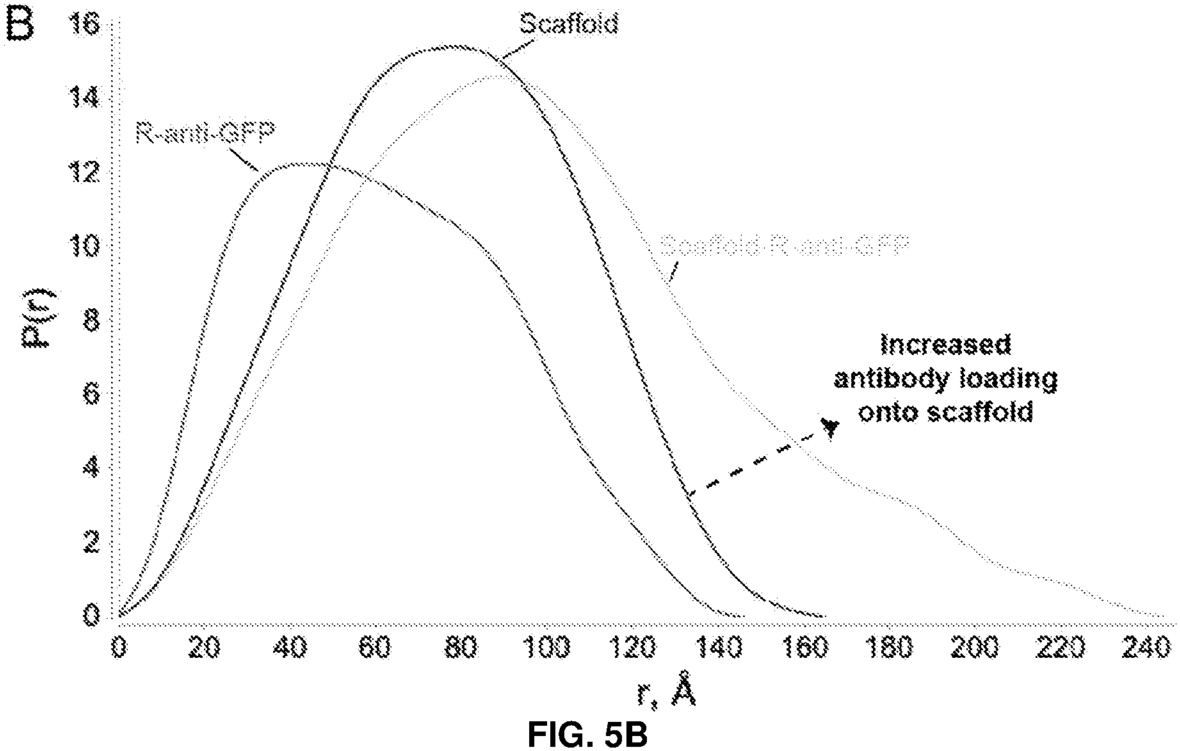
FIG. 5B. SEC SAXS of a scaffold with a rabbit anti-GFP antibody. P(r) function histograms.

To structurally assess the scaffold for Fc and antibody binding, we used the solution technique SEC-SAXS-MALS (FIGS. 4A, 4B, 5A and 5B, respectively). Regions of sample peaks of scaffold, hFc, and scaffold-hFc complex were chosen for further scattering analysis (FIG. 4A). All molecules/complexes are compared in FIG. 4B using the P(r) function, which are histograms of orientationally averaged distances of the scattering particles (8). Thus, the greater the area under these histograms, the greater the magnitude and number of 'molecule edge-to-molecule edge' distances within the molecules there are. Therefore, the increased diameters of the scaffold through the addition of hFc and antibody molecules will be readily apparent via the P(r) function. In FIG. 4B it is clear that the various scaffold states (X, Y, Z) along the Scaffold-hFc peak in FIG. 4A represent loading of hFc molecules onto the scaffold. This loading trend is also seen in the increase in radius of gyration (Rg) and maximum dimension (Dmax) in Table 1. Further support for hFc loading onto the scaffold is in the MALS data in Table 1, where the MALS Averaged Molecular Weight of the Peak increased from 764 kDa to 1020 kDa with the addition of hFc to the scaffold. Similar results were found when characterizing the binding of a polyclonal IgG rabbit anti-GFP antibody to the scaffold (scaffold-R-anti-GFP) using SEC-SAXS-MALS in FIGS. 5A and 5B. Analysis of a single region of the scaffold-R-anti-GFP peak, demonstrates an increase in the P(r) function (FIG. 5B), and the Rg, Dmax, and MALS Averaged Molecular Weight of the Peak (Table 1).

TABLE 1

Characteristics of scaffold with hFc (IgG1) and R-anti-GFP antibody (IgG).

| Molecule/Complex | Radius of Gyration (Å) | Maximum Dimension (Å) | MALS Averaged Molecular Weight of Peak (kDa) |
|---|---|---|---|
| hFc | 27.31 | 74 | 61 |
| Scaffold | 59.76 | 165 | 764 |
| Scaffold-hFc Z | 61.56 | 185 | 1020 |
| Scaffold-hFc Y | 72.47 | 258 | |
| Scaffold-hFc X | 81.39 | 281 | |
| R-anti-GFP | 48.09 | 74 | 145 |
| Scaffold-R-anti-GFP | 72.41 | 244 | 1568 |

TABLE 2

Sequences of scaffold variants designed and experimentally tested to-date.

Initial Published Template:
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTDDNPDGAAPQEFFDGIV
AAVKADRYAFYTGFFNDFYNLDENLGTRISEEAVRNSWNTAASGGFFAAA
AAPTTWYTDFRADIPRIDVPALILHGTGDRTLPIENTARVFHKALPSAEY
VEVEGAPHGLLWTHAEEVNTALLAFLAKAQEAQKQKLLTEVETYVLSIIP
SGPLKAEIAQRLEDVFAGKNTDLEVLMEWLKTRPILSPLTKGILGFVFTL
TVPSERGLQRRRFVQNALNGNGDPNNMDKAVKLYRKLKREITFHGAKEIS
LSYSAGALASCMGLIYNRMGAVTTEVAFGLVCATCEQIADSQHRSHRQLE
HHHHHH (SEQ ID NO: 40)

SAPNA_1
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTGCDCAWHLGELVWCTCG
DNPDGAAPQEFFDGIVAAVKADRYAFYTGFFNDFYNLDENLGTRISEEAV
RNSWNTAASGGFFAAAAAPTTWYTDFRADIPRIDVPALILHGTGDRTLPI
ENTARVFHKALPSAEYVEVEGAPHGLLWTHAEEVNTALLAFLAKAQEAQK
QKLLTEVETYVLSIIPSGPLKAEIAQRLEDVFAGKNTDLEVLMEWLKTRP
ILSPLTKGILGFVFTLTVPSERGLQRRRFVQNALNGNGDPNNMDKAVKLY
RKLKREITFHGAKEISLSYSAGALASCMGLIYNRMGAVTTEVAFGLVCAT
CEQIADSQHRSHRQLEHHHHHH (SEQ ID NO: 1)

TABLE 2 -continued

Sequences of scaffold variants designed and experimentally tested to-date.

SAPNA_2
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTGCDCAWHLGELVWCTCG
DNPDGAAPQEFFDGIVAAVKADRYAFYTGFFNDFYNLDENLGTRISEEAV
RNSWNTAASGGFFAAAAAPTTWYTDFRADIPRIDVPALILHGTGDRTLPI
ENTARVFHKALPSAEYVEVEGAPHGLLWTHAEEVNTALLAFLAKAQEAQK
QKLLTEVETYVLSIIPSGPLKAEIAQRLEDVFAGKNTDLEVLMEWLKTRP
ILSPLTKGILGFVFTLTVPSERGLQRRRFVQNALNGNGDPNNMDKAVKLY
RKLKREITFHGAKEISLSYSAGALASCMGLIYNRMGAVTTEVAFGLVCAT
CEQIADSQENLYFQGLEHHHHHH (SEQ ID NO: 2)

SAPNA_3
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTGGGSGCDCAWHLGELVW
CTCGSGGGDNPDGAAPQEFFDGIVAAVKADRYAFYTGFFNDFYNLDENLG
TRISEEAVRNSWNTAASGGFFAAAAAPTTWYTDFRADIPRIDVPALILHG
TGDRTLPIENTARVFHKALPSAEYVEVEGAPHGLLWTHAEEVNTALLAFL
AKAQEAQKQKLLTEVETYVLSIIPSGPLKAEIAQRLEDVFAGKNTDLEVL
MEWLKTRPILSPLTKGILGFVFTLTVPSERGLQRRRFVQNALNGNGDPNN
MDKAVKLYRKLKREITFHGAKEISLSYSAGALASCMGLIYNRMGAVTTEV
AFGLVCATCEQIADSQHRSHRQLEHHHHHH (SEQ ID NO: 3)

SAPNA_4
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTGGGSGCDCAWHLGELVW
CTCGSGGGDNPDGAAPQEFFDGIVAAVKADRYAFYTGFFNDFYNLDENLG
TRISEEAVRNSWNTAASGGFFAAAAAPTTWYTDFRADIPRIDVPALILHG
TGDRTLPIENTARVFHKALPSAEYVEVEGAPHGLLWTHAEEVNTALLAFL
AKAQEAQKQKLLTEVETYVLSIIPSGPLKAEIAQRLEDVFAGKNTDLEVL
MEWLKTRPILSPLTKGILGFVFTLTVPSERGLQRRRFVQNALNGNGDPNN
MDKAVKLYRKLKREITFHGAKEISLSYSAGALASCMGLIYNRMGAVTTEV
AFGLVCATCEQIADSQENLYFQGLEHHHHHH (SEQ ID NO: 4)

SAPNA_5
MPFITVGQENSTSIDLYYEDHGTGTPVVLIHGFPLSGHSWERQSAALLDA
GARVITYDRRGFGQSSQPTTGYDYDTFAADLNTVLETLDLQDAVLVGFSM
GTGEVARYVSSYGTARIAAVAFLASLEPFLLKTGCDCAWHLGELVWCTCG
DNPDGAAPQEFFDGIVAAVKADRYAFYTGFFNDFYNLDENLGTRISEEAV
RNSWNTAASGGFFAAAAAPTTWYTDFRADIPRIDVPALILHGTGDRTLPI
ENTARVFHKALPSAEYVEVEGAPHGLLWTHAEEVNTALLAFLAKAQEAQK
QKLLTEVETYVLSIIPSGPLKAEIAQRLEDVFAGKNTDLEVLMEWLKTRP
ILSPLTKGILGFVFTLTVPSERGLQRRRFVQNALNGNGDPNNMDKAVKLY
RKLKREITFHGAKEISLSYSAGALASCMGLIYNRMGAVTTEVAFGLVCAT
CEQIADSQHRSHRQLEHHHHHH (SEQ ID NO: 5)

SAPNA_6
MPFITVGQENSTSIDLYYEDHGTGTPVVLIHGFPLSGHSWERQSAALLDA
GARVITYDRRGFGQSSQPTTGYDYDTFAADLNTVLETLDLQDAVLVGFSM
GTGEVARYVSSYGTARIAAVAFLASLEPFLLKTGCDCAWHLGELVWCTCG
DNPDGAAPQEFFDGIVAAVKADRYAFYTGFFNDFYNLDENLGTRISEEAV
RNSWNTAASGGFFAAAAAPTTWYTDFRADIPRIDVPALILHGTGDRTLPI
ENTARVFHKALPSAEYVEVEGAPHGLLWTHAEEVNTALLAFLAKAQEAQK
QKLLTEVETYVLSIIPSGPLKAEIAQRLEDVFAGKNTDLEVLMEWLKTRP
ILSPLTKGILGFVFTLTVPSERGLQRRRFVQNALNGNGDPNNMDKAVKLY
RKLKREITFHGAKEISLSYSAGALASCMGLIYNRMGAVTTEVAFGLVCAT
CEQIADSQENLYFQGLEHHHHHH (SEQ ID NO: 6)

SAPNA_7
MPFITVGQENSTSIDLYYEDHGTGTPVVLIHGFPLSGHSWERQSAALLDA
GARVITYDRRGFGQSSQPTTGYDYDTFAADLNTVLETLDLQDAVLVGFSM
GTGEVARYVSSYGTARIAAVAFLASLEPFLLKTGGGSGCDCAWHLGELVW
CTCGSGGGDNPDGAAPQEFFDGIVAAVKADRYAFYTGFFNDFYNLDENLG
TRISEEAVRNSWNTAASGGFFAAAAAPTTWYTDFRADIPRIDVPALILHG
TGDRTLPIENTARVFHKALPSAEYVEVEGAPHGLLWTHAEEVNTALLAFL
AKAQEAQKQKLLTEVETYVLSIIPSGPLKAEIAQRLEDVFAGKNTDLEVL
MEWLKTRPILSPLTKGILGFVFTLTVPSERGLQRRRFVQNALNGNGDPNN
MDKAVKLYRKLKREITFHGAKEISLSYSAGALASCMGLIYNRMGAVTTEV
AFGLVCATCEQIADSQHRSHRQLEHHHHHH (SEQ ID NO: 7)

SAPNA_8
MPFITVGQENSTSIDLYYEDHGTGTPVVLIHGFPLSGHSWERQSAALLDA
GARVITYDRRGFGQSSQPTTGYDYDTFAADLNTVLETLDLQDAVLVGFSM
GTGEVARYVSSYGTARIAAVAFLASLEPFLLKTGGGSGCDCAWHLGELVW
CTCGSGGGDNPDGAAPQEFFDGIVAAVKADRYAFYTGFFNDFYNLDENLG
TRISEEAVRNSWNTAASGGFFAAAAAPTTWYTDFRADIPRIDVPALILHG
TGDRTLPIENTARVFHKALPSAEYVEVEGAPHGLLWTHAEEVNTALLAFL
AKAQEAQKQKLLTEVETYVLSIIPSGPLKAEIAQRLEDVFAGKNTDLEVL
MEWLKTRPILSPLTKGILGFVFTLTVPSERGLQRRRFVQNALNGNGDPNN
MDKAVKLYRKLKREITFHGAKEISLSYSAGALASCMGLIYNRMGAVTTEV
AFGLVCATCEQIADSQENLYFQGLEHHHHHH (SEQ ID NO: 8)

SAPNA_9
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTGRWGCDCAWHLGELVWC
TCGWEGDNPDGAAPQEFFDGIVAAVKADRYAFYTGFFNDFYNLDENLGTR
ISEEAVRNSWNTAASGGFFAAAAAPTTWYTDFRADIPRIDVPALILHGTG
DRTLPIENTARVFHKALPSAEYVEVEGAPHGLLWTHAEEVNTALLAFLAK
AQEAQKQKLLTEVETYVLSIIPSGPLKAEIAQRLEDVFAGKNTDLEVLME
WLKTRPILSPLTKGILGFVFTLTVPSERGLQRRRFVQNALNGNGDPNNMD
KAVKLYRKLKREITFHGAKEISLSYSAGALASCMGLIYNRMGAVTTEVAF
GLVCATCEQIADSQHRSHRQLEHHHHHH (SEQ ID NO: 9)

SAPNA_10
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTGRWDCAWHLGELVWCTW
EGDNPDGAAPQEFFDGIVAAVKADRYAFYTGFFNDFYNLDENLGTRISEE
AVRNSWNTAASGGFFAAAAAPTTWYTDFRADIPRIDVPALILHGTGDRTL
PIENTARVFHKALPSAEYVEVEGAPHGLLWTHAEEVNTALLAFLAKAQEA
QKQKLLTEVETYVLSIIPSGPLKAEIAQRLEDVFAGKNTDLEVLMEWLKT
RPILSPLTKGILGFVFTLTVPSERGLQRRRFVQNALNGNGDPNNMDKAVK
LYRKLKREITFHGAKEISLSYSAGALASCMGLIYNRMGAVTTEVAFGLVC
ATCEQIADSQHRSHRQLEHHHHHH (SEQ ID NO: 10)

SAPNA_11
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTGGGGRWDCAWHLGELVW
CTWEGGGGDNPDGAAPQEFFDGIVAAVKADRYAFYTGFFNDFYNLDENLGL
TRISEEAVRNSWNTAASGGFFAAAAAPTTWYTDFRADIPRIDVPALIHGTG
DRTLPIENTARVFHKALPSAEYVEVEGAPHGLLWTHAEEVNTALLAFLAKA
QEAQKQKLLTEVETYVLSIIPSGPLKAEIAQRLEDVFAGKNTDLEVLMEWL
KTRPILSPLTKGILGFVFTLTVPSERGLQRRRFVQNALNGNGDPNNMDKAV
KLYRKLKREITFHGAKEISLSYSAGALASCMGLIYNRMGAVTTEVAFGLVC
ATCEQIADSQHRSHRQLEHHHHHH (SEQ ID NO: 11)

SAPNA_12
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTGGGGRWDAAWHLGELVW
ATWEGGGGDNPDGAAPQEFFDGIVAAVKADRYAFYTGFFNDFYNLDENLG
TRISEEAVRNSWNTAASGGFFAAAAAPTTWYTDFRADIPRIDVPALILHG
TGDRTLPIENTARVFHKALPSAEYVEVEGAPHGLLWTHAEEVNTALLAFL
AKAQEAQKQKLLTEVETYVLSIIPSGPLKAEIAQRLEDVFAGKNTDLEVL
MEWLKTRPILSPLTKGILGFVFTLTVPSERGLQRRRFVQNALNGNGDPNN
MDKAVKLYRKLKREITFHGAKEISLSYSAGALASCMGLIYNRMGAVTTEV
AFGLVCATCEQIADSQHRSHRQLEHHHHHH (SEQ ID NO: 12)

SAPNA_13
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTGGGSGADCAWHLGELVW
CTAGSGGGDNPDGAAPQEFFDGIVAAVKADRYAFYTGFFNDFYNLDENLG
TRISEEAVRNSWNTAASGGFFAAAAAPTTWYTDFRADIPRIDVPALILHG
TGDRTLPIENTARVFHKALPSAEYVEVEGAPHGLLWTHAEEVNTALLAFL
AKAQEAQKQKLLTEVETYVLSIIPSGPLKAEIAQRLEDVFAGKNTDLEVL
MEWLKTRPILSPLTKGILGFVFTLTVPSERGLQRRRFVQNALNGNGDPNN
MDKAVKLYRKLKREITFHGAKEISLSYSAGALASCMGLIYNRMGAVTTEV
AFGLVCATCEQIADSQHRSHRQLEHHHHHH (SEQ ID NO: 13)

SAPNA_14
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTGGGSGADAAWHLGELVW
ATAGSGGGDNPDGAAPQEFFDGIVAAVKADRYAFYTGFFNDFYNLDENLG
TRISEEAVRNSWNTAASGGFFAAAAAPTTWYTDFRADIPRIDVPALILHG
TGDRTLPIENTARVFHKALPSAEYVEVEGAPHGLLWTHAEEVNTALLAFL
AKAQEAQKQKLLTEVETYVLSIIPSGPLKAEIAQRLEDVFAGKNTDLEVL

TABLE 2 -continued

Sequences of scaffold variants designed
and experimentally tested to-date.

MEWLKTRPILSPLTKGILGFVFTLTVPSERGLQRRRFVQNALNGNGDPNN
MDKAVKLYRKLKREITFHGAKEISLSYSAGALASCMGLIYNRMGAVTTEV
AFGLVCATCEQIADSQHRSHRQLEHHHHHH (SEQ ID NO: 14)

SAPNA_15
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTDDNPDGAAPQEFFDGIV
AAVKADRYAFYTGFFNDFYNLDENLGTRISEEAVRNSWNTAASGGFFAAA
AAPTTWYTDFRADIPRIDVPALILHGTGDRTLPIENTARVFHKALPSGGG
SGCDCAWHLGELVWCTCGSGGGAEYVEVEGAPHGLLWTHAEEVNTALLAF
LAKAQEAQKQKLLTEVETYVLSIIPSGPLKAEIAQRLEDVFAGKNTDLEV
LMEWLKTRPILSPLTKGILGFVFTLTVPSERGLQRRRFVQNALNGNGDPN
NMDKAVKLYRKLKREITFHGAKEISLSYSAGALASCMGLIYNRMGAVTTE
VAFGLVCATCEQIADSQHRSHRQLEHHHHHH (SEQ ID NO: 15)

SAPNA_16
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTDDNPDGAAPQEFFDGIV
AAVKADRYAFYTGFFNDFYNLDENLGTRISEEAVRNSWNTAASGGFFAAA
AAPTTWYTDFRADIPRIGGGSGCDCAWHLGELVWCTCGSGGGVPALILHG
TGDRTLPIENTARVFHKALPSAEYVEVEGAPHGLLWTHAEEVNTALLAFL
AKAQEAQKQKLLTEVETYVLSIIPSGPLKAEIAQRLEDVFAGKNTDLEVL
MEWLKTRPILSPLTKGILGFVFTLTVPSERGLQRRRFVQNALNGNGDPNN
MDKAVKLYRKLKREITFHGAKEISLSYSAGALASCMGLIYNRMGAVTTEV
AFGLVCATCEQIADSQHRSHRQLEHHHHHH (SEQ ID NO: 16)

SAPNA_17
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTDDNPDGAAPQEFFDGIV
AAVKADRYAFYTGFFNDFYNLGGGSGCDCAWHLGELVWCTCGSGGGRISE
EAVRNSWNTAASGGFFAAAAAPTTWYTDFRADIPRIDVPALILHGTGDRT
LPIENTARVFHKALPSAEYVEVEGAPHGLLWTHAEEVNTALLAFLAKAQE
AQKQKLLTEVETYVLSIIPSGPLKAEIAQRLEDVFAGKNTDLEVLMEWLK
TRPILSPLTKGILGFVFTLTVPSERGLQRRRFVQNALNGNGDPNNMDKAV
KLYRKLKREITFHGAKEISLSYSAGALASCMGLIYNRMGAVTTEVAFGLV
CATCEQIADSQHRSHRQLEHHHHHH (SEQ ID NO: 17)

SAPNA_18
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTDDNPDGAAPQEFFDGIV
AAVKADRYAFYTGFFNDFYNLDENLGTRISEEAVRNSWNTAASGGFFAAA
AAPTTWYTDFRADIPRIDVPALILHGTGGGSGCDCAWHLGELVWCTCGSG
GGTLPIENTARVFHKALPSAEYVEVEGAPHGLLWTHAEEVNTALLAFLAK
AQEAQKQKLLTEVETYVLSIIPSGPLKAEIAQRLEDVFAGKNTDLEVLME
WLKTRPILSPLTKGILGFVFTLTVPSERGLQRRRFVQNALNGNGDPNNMD
KAVKLYRKLKREITFHGAKEISLSYSAGALASCMGLIYNRMGAVTTEVAF
GLVCATCEQIADSQHRSHRQLEHHHHHH (SEQ ID NO: 18)

SAPNA_19
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGGGSGCDCAWHLGELVWCTCGSGGGRIAAVAFLASLEP
FLLKTDDNPDGAAPQEFFDGIVAAVKADRYAFYTGFFNDFYNLDENLGTR
ISEEAVRNSWNTAASGGFFAAAAAPTTWYTDFRADIPRIDVPALILHGTG
DRTLPIENTARVFHKALPSAEYVEVEGAPHGLLWTHAEEVNTALLAFLAK
AQEAQKQKLLTEVETYVLSIIPSGPLKAEIAQRLEDVFAGKNTDLEVLME
WLKTRPILSPLTKGILGFVFTLTVPSERGLQRRRFVQNALNGNGDPNNMD
KAVKLYRKLKREITFHGAKEISLSYSAGALASCMGLIYNRMGAVTTEVAF
GLVCATCEQIADSQHRSHRQLEHHHHHH (SEQ ID NO: 19)

SAPNA_20
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTDDNPDGAAPQEFFDGIV
AAVKADRYAFYTGFFNDFYNLDENLGTRISEEAVRNSWNTAASGGFFAAA
AAPTTWYTDFRADIPRIDVPALILHGTGDRTLPIENTARVFHKALPSAEY
VEVEGAPHGLLWTHAEEVNTALLAFLAKAQEAQKQKLLTEVETYVLSIIP
SGPLKAEIAQRLEDVFAGGGGSGCDCAWHLGELVWCTCGSGGGDLEVLME
WLKTRPILSPLTKGILGFVFTLTVPSERGLQRRRFVQNALNGNGDPNNMD
KAVKLYRKLKREITFHGAKEISLSYSAGALASCMGLIYNRMGAVTTEVAF
GLVCATCEQIADSQHRSHRQLEHHHHHH (SEQ ID NO: 20)

TABLE 2 -continued

Sequences of scaffold variants designed
and experimentally tested to-date.

SAPNA_21
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTDDNPDGAAPQEFFDGIV
AAVKADRYAFYTGFFNDFYNLDENLGTRISEEAVRNSWNTAASGGFFAAA
AAPTTWYTDFRADIPRIDVPALILHGTGDRTLPIENTARVFHKALPSAEY
VEVEGAPHGLLWTHAEEVNTALLAFLAKAQEAQKQKLLTEVETYVLSIIP
SGPLKAEIAQRLEDVFAGKNTDLEVLMEWLKTRPILSPLTKGILGFVFTL
TVPSERGLQRRRFVQNALNGNGDPNNMDKAVKLYRKLKREITFHGAKEIS
LSYSAGALASCMGLIYNRMGAVTTEVAFGLVCATCEQIADSQGGGSGCDC
AWHLGELVWCTCGSGGGLEHHHHHH (SEQ ID NO: 21)

SAPNA_22
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTDDNPDGAAPQEFFDGIV
AAVKADRYAFYTGFFNDFYNLDENLGTRISEEAVRNSWNTAASGGFFAAA
AAPTTWYTDFRADIPRIDVPALILHGTGDRTLPIENTARVFHKALPSAEY
VEVEGAPHGLLWTHAEEVNTALLAFLAKAQEAQKQKLLTEVETYVLSIIP
SGPLKAEIAQRLEDVFAGGGRWGCDCAWHLGELVWCTCGWEGGDLEVLME
WLKTRPILSPLTKGILGFVFTLTVPSERGLQRRRFVQNALNGNGDPNNMD
KAVKLYRKLKREITFHGAKEISLSYSAGALASCMGLIYNRMGAVTTEVAF
GLVCATCEQIADSQHRSHRQLEHHHHHH (SEQ ID NO: 22)

SAPNA_23
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTDDNPDGAAPQEFFDGIV
AAVKADRYAFYTGFFNDFYNLDENLGTRISEEAVRNSWNTAASGGFFAAA
AAPTTWYTDFRADIPRIDVPALILHGTGDRTLPIENTARVFHKALPSAEY
VEVEGAPHGLLWTHAEEVNTALLAFLAKAQEAQKQKLLTEVETYVLSIIP
SGPLKAEIAQRLEDVFAGRWGSGCDCAWHLGELVWCTCGSGWEDLEVLME
WLKTRPILSPLTKGILGFVFTLTVPSERGLQRRRFVQNALNGNGDPNNMD
KAVKLYRKLKREITFHGAKEISLSYSAGALASCMGLIYNRMGAVTTEVAF
GLVCATCEQIADSQHRSHRQLEHHHHHH (SEQ ID NO: 23)

SAPNA_24
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTDDNPDGAAPQEFFDGIV
AAVKADRYAFYTGFFNDFYNLDENLGTRISEEAVRNSWNTAASGGFFAAA
AAPTTWYTDFRADIPRIDVPALILHGTGDRTLPIENTARVFHKALPSAEY
VEVEGAPHGLLWTHAEEVNTALLAFLAKAQEAQKQKLLTEVETYVLSIIP
SGPLKAEIAQRLEDVFAGGGGCDCAWHLGELVWCTCGGGDLEVLMEWLKT
RPILSPLTKGILGFVFTLTVPSERGLQRRRFVQNALNGNGDPNNMDKAVK
LYRKLKREITFHGAKEISLSYSAGALASCMGLIYNRMGAVTTEVAFGLVC
ATCEQIADSQHRSHRQLEHHHHHH (SEQ ID NO: 24)

SAPNA_25
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTDDNPDGAAPQEFFDGIV
AAVKADRYAFYTGFFNDFYNLDENLGTRISEEAVRNSWNTAASGGFFAAA
AAPTTWYTDFRADIPRIDVPALILHGTGDRTLPIENTARVFHKALPSAEY
VEVEGAPHGLLWTHAEEVNTALLAFLAKAQEAQKQKLLTEVETYVLSIIP
SGPLKAEIAQRLEDVFAGGCDCAWHLGELVWCTCGDLEVLMEWLKTRPIL
SPLTKGILGFVFTLTVPSERGLQRRRFVQNALNGNGDPNNMDKAVKLYRK
LKREITFHGAKEISLSYSAGALASCMGLIYNRMGAVTTEVAFGLVCATCE
QIADSQHRSHRQLEHHHHHH (SEQ ID NO: 25)

SAPNA_26
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTDDNPDGAAPQKFFDGIV
AAVKADRYAFYTGFFNDFYNLDENLGTRISEEAVRNSWNTAASGGFFAAA
AAPTTWYTDFRADIPRIDVPALILHGTGDRTLPIENTARVFHKALPSAEY
VEVEGAPHGLLWTHAEEVNTALLAFLAKAQEAQKQKLLTEVETYVLSIIP
SGPLKAEIAQRLEDVFAGKNTDLEVLMEWLKTRPILSPLTKGILGFVFTL
TVPSERGLQRRRFVQNALNGNGDPNNMDKAVKLYRKLKREITFHGAKEIS
LSYSAGALASCMGLIYNRMGAVTTEVAFGLVCATCEQIADSQGGGSGCDC
AWHLGELVWCTCGSGGGLEHHHHHH (SEQ ID NO: 26)

SAPNA_27
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTDDNPDGAAPQEFFDGIV
AAVKADRYAFYTGFFNDFYNLKENLGTRISEEAVRNSWNTAASGGFFAAA

TABLE 2 -continued

Sequences of scaffold variants designed and experimentally tested to-date.

AAPTTWYTDFRADIPRIDVPALILHGTGDRTLPIENTARVFHKALPSAEY
VEVEGAPHGLLWTHAEEVNTALLAFLAKAQEAQKQKLLTEVETYVLSIIP
SGPLKAEIAQRLEDVFAGKNTDLEVLMEWLKTRPILSPLTKGILGFVFTL
TVPSERGLQRRRFVQNALNGNGDPNNMDKAVKLYRKLKREITFHGAKEIS
LSYSAGALASCMGLIYNRMGAVTTEVAFGLVCATCEQIADSQGGGSGCDC
AWHLGELVWCTCGSGGGLEHHHHHH (SEQ ID NO: 27)

SAPNA_28
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTDDNPDGAAPQEFFDGIV
AAVKADRYAFYTGFFNDFYNLDENLGTRISEEAVRNSWNTAASGGFFAAA
AAPTTWYTDFRADIPRIDVPALILHGTGDRTLPIKNTARVFHKALPSAEY
VEVEGAPHGLLWTHAEEVNTALLAFLAKAQEAQKQKLLTEVETYVLSIIP
SGPLKAEIAQRLEDVFAGKNTDLEVLMEWLKTRPILSPLTKGILGFVFTL
TVPSERGLQRRRFVQNALNGNGDPNNMDKAVKLYRKLKREITFHGAKEIS
LSYSAGALASCMGLIYNRMGAVTTEVAFGLVCATCEQIADSQGGGSGCDC
AWHLGELVWCTCGSGGGLEHHHHHH (SEQ ID NO: 28)

SAPNA_29
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTDDNPDGAAPQKFFDGIV
AAVKADRYAFYTGFFNDFYNLKENLGTRISEEAVRNSWNTAASGGFFAAA
AAPTTWYTDFRADIPRIDVPALILHGTGDRTLPIENTARVFHKALPSAEY
VEVEGAPHGLLWTHAEEVNTALLAFLAKAQEAQKQKLLTEVETYVLSIIP
SGPLKAEIAQRLEDVFAGKNTDLEVLMEWLKTRPILSPLTKGILGFVFTL
TVPSERGLQRRRFVQNALNGNGDPNNMDKAVKLYRKLKREITFHGAKEIS
LSYSAGALASCMGLIYNRMGAVTTEVAFGLVCATCEQIADSQGGGSGCDC
AWHLGELVWCTCGSGGGLEHHHHHH (SEQ ID NO: 29)

SAPNA_30
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTDDNPDGAAPQEFFDGIV
AAVKADRYAFYTGFFNDFYNLKENLGTRISEEAVRNSWNTAASGGFFAAA
AAPTTWYTDFRADIPRIDVPALILHGTGDRTLPIKNTARVFHKALPSAEY
VEVEGAPHGLLWTHAEEVNTALLAFLAKAQEAQKQKLLTEVETYVLSIIP
SGPLKAEIAQRLEDVFAGKNTDLEVLMEWLKTRPILSPLTKGILGFVFTL
TVPSERGLQRRRFVQNALNGNGDPNNMDKAVKLYRKLKREITFHGAKEIS
LSYSAGALASCMGLIYNRMGAVTTEVAFGLVCATCEQIADSQGGGSGCDC
AWHLGELVWCTCGSGGGLEHHHHHH (SEQ ID NO: 30)

SAPNA_31
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTDDNPDGAAPQKFFDGIV
AAVKADRYAFYTGFFNDFYNLDENLGTRISEEAVRNSWNTAASGGFFAAA
AAPTTWYTDFRADIPRIDVPALILHGTGDRTLPIKNTARVFHKALPSAEY
VEVEGAPHGLLWTHAEEVNTALLAFLAKAQEAQKQKLLTEVETYVLSIIP
SGPLKAEIAQRLEDVFAGKNTDLEVLMEWLKTRPILSPLTKGILGFVFTL
TVPSERGLQRRRFVQNALNGNGDPNNMDKAVKLYRKLKREITFHGAKEIS
LSYSAGALASCMGLIYNRMGAVTTEVAFGLVCATCEQIADSQGGGSGCDC
AWHLGELVWCTCGSGGGLEHHHHHH (SEQ ID NO: 31)

SAPNA_32
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTDDNPDGAAPQKFFDGIV
AAVKADRYAFYTGFFNDFYNLKENLGTRISEEAVRNSWNTAASGGFFAAA
AAPTTWYTDFRADIPRIDVPALILHGTGDRTLPIKNTARVFHKALPSAEY
VEVEGAPHGLLWTHAEEVNTALLAFLAKAQEAQKQKLLTEVETYVLSIIP
SGPLKAEIAQRLEDVFAGKNTDLEVLMEWLKTRPILSPLTKGILGFVFTL
TVPSERGLQRRRFVQNALNGNGDPNNMDKAVKLYRKLKREITFHGAKEIS
LSYSAGALASCMGLIYNRMGAVTTEVAFGLVCATCEQIADSQGGGSGCDC
AWHLGELVWCTCGSGGGLEHHHHHH (SEQ ID NO: 32)

SAPNA_33
MPFITVGQENSTSIDLYYEDHGTGTPVVLIHGFPLSGHSWERQSAALLDA
GARVITYDRRGFGQSSQPTTGYDYDTFAADLNTVLETLDLQDAVLVGFSM
GTGEVARYVSSYGTARIAAVAFLASLEPFLLKTDDNPDGAAPQEFFDGIV
AAVKADRYAFYTGFFNDFYNLDENLGTRISEEAVRNSWNTAASGGFFAAA
AAPTTWYTDFRADIPRIDVPALILHGTGDRTLPIENTARVFHKALPSAEY
VEVEGAPHGLLWTHAEEVNTALLAFLAKAQEAQKQKLLTEVETYVLSIIP
SGPLKAEIAQRLEDVFAGKNTDLEVLMEWLKTRPILSPLTKGILGFVFTL

TABLE 2 -continued

Sequences of scaffold variants designed and experimentally tested to-date.

TVPSERGLQRRRFVQNALNGNGDPNNMDKAVKLYRKLKREITFHGAKEIS
LSYSAGALASCMGLIYNRMGAVTTEVAFGLVCATCEQIADSQGGGSGCDC
AWHLGELVWCTCGSGGGLEHHHHHH (SEQ ID NO: 33)

SAPNA_34
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTDDNPDGAAPQEFFDGIV
AAVKADRYAFYTGFFNDFYNLDENLGTRISEEAVRNSWNTAASGGFFAAA
AAPTTWYTDFRADIPRIDVPALILHGTGDRTLPIENTARVFHKALPSAEY
VEVEGAPHGLLWTHAEEVNTALLAFLAKAQEAQKQKLLTEVETYVLSIIP
SGPLKAEIAQRLEDVFAGKNTDLEVLMEWLKTRPILSPLTKGILGFVFTL
TVPSERGLQRRRFVQNALNGNGDPNNMDKAVKLYRKLKREITFHGAKEIS
LSYSAGALASCMGLIYNRMGAVTTEVAFGLVCATCEQIADSQGGGSGGGG
CDCAWHLGELVWCTCGSGGGLEHHHHHH (SEQ ID NO: 34)

SAPNA_35
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTDDNPDGAAPQEFFDGIV
AAVKADRYAFYTGFFNDFYNLDENLGTRISEEAVRNSWNTAASGGFFAAA
AAPTTWYTDFRADIPRIDVPALILHGTGDRTLPIENTARVFHKALPSAEY
VEVEGAPHGLLWTHAEEVNTALLAFLAKAQEAQKQKLLTEVETYVLSIIP
SGPLKAEIAQRLEDVFAGKNTDLEVLMEWLKTRPILSPLTKGILGFVFTL
TVPSERGLQRRRFVQNALNGNGDPNNMDKAVKLYRKLKREITFHGAKEIS
LSYSAGALASCMGLIYNRMGAVTTEVAFGLVCATCEQIADSQGGGSGGGS
GGCDCAWHLGELVWCTCGSGGGLEHHHHHH (SEQ ID NO: 35)

SAPNA_36
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTDDNPDGAAPQEFFDGIV
AAVKADRYAFYTGFFNDFYNLDENLGTRISEEAVRNSWNTAASGGFFAAA
AAPTTWYTDFRADIPRIDVPALILHGTGDRTLPIENTARVFHKALPSAEY
VEVEGAPHGLLWTHAEEVNTALLAFLAKAQEAQKQKLLTEVETYVLSIIP
SGPLKAEIAQRLEDVFAGKNTDLEVLMEWLKTRPILSPLTKGILGFVFTL
TVPSERGLQRRRFVQNALNGNGDPNNMDKAVKLYRKLKREITFHGAKEIS
LSYSAGALASCMGLIYNRMGAVTTEVAFGLVCATCEQIADSQGGGSGGGS
GGGSGGGSGGGSGGGSGGGSGGGSGGGSGGGSGGGSGGGSGGGSGGGSGG
GSGGGSGCDCAWHLGELVWCTCGSGGGLDHHHHHH (SEQ ID NO: 36)

SAPNA_37
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTDDNPDGAAPQEFFDGIV
AAVKADRYAFYTGFFNDFYNLDENLGTRISEEAVRNSWNTAASGGFFAAA
AAPTTWYTDFRADIPRIDVPALILHGTGDRTLPIENTARVFHKALPSAEY
VEVEGAPHGLLWTHAEEVNTALLAFLAKAQEAQKQKLLTEVETYVLSIIP
SGPLKAEIAQRLEDVFAGRWGSGADCAWHLGELVWCTAGSGWEDLEVLME
WLKTRPILSPLTKGILGFVFTLTVPSERGLQRRRFVQNALNGNGDPNNMD
KAVKLYRKLKREITFHGAKEISLSYSAGALASCMGLIYNRMGAVTTEVAF
GLVCATCEQIADSQHRSHRQLEHHHHHH (SEQ ID NO: 37)

SAPNA_38
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTDDNPDGAAPQEFFDGIV
AAVKADRYAFYTGFFNDFYNLDENLGTRISEEAVRNSWNTAASGGFFAAA
AAPTTWYTDFRADIPRIDVPALILHGTGDRTLPIENTARVFHKALPSAEY
VEVEGAPHGLLWTHAEEVNTALLAFLAKAQEAQKQKLLTEVETYVLSIIP
SGPLKAEIAQRLEDVFAGGGRWGADCAWHLGELVWCTAGWEGGDLEVLME
WLKTRPILSPLTKGILGFVFTLTVPSERGLQRRRFVQNALNGNGDPNNMD
KAVKLYRKLKREITFHGAKEISLSYSAGALASCMGLIYNRMGAVTTEVAF
GLVCATCEQIADSQHRSHRQLEHHHHHH (SEQ ID NO: 38)

SAPNA_39
MPFITVGQENSTSIDLYYEDHGTGTPVVLIHGFPLSGHSWERQSAALLDA
GYRVITYDRRGFGQSSQPTTGYDYDTFAADLNTVLETLDLQDAVLVGFSM
GTGEVARYVSSYGTARIAAVAFLASLEPFLLKTDDNPDGAAPQEFFDGIV
AAVKADRYAFYTGFFNDFYNLDENLGTRISEEAVRNSWNTAASGGFFAAA
AAPTTWYTDFRADIPRIDVPALILHGTGDRTLPIENTARVFHKALPSAEY
VEVEGAPHGLLWTHAEEVNTALLAFLAKAQEAQKQKLLTEVETYVLSIIP

TABLE 2 -continued

| Sequences of scaffold variants designed and experimentally tested to-date. |
|---|
| SGPLKAEIAQRLEDVFAGGADCAWHLGELVWCTAGDLEVLMEWLKTRPIL SPLTKGILGFVFTLTVPSERGLQRRRFVQNALNGNGDPNNMDKAVKLYRK LKREITFHGAKEISLSYSAGALASCMGLIYNRMGAVTTEVAFGLVCATCE QIADSQHRSHRQLEHHHHHH (SEQ ID NO: 39) |

REFERENCES CITED IN EXAMPLE 1

1. Y. T. Lai, D. Cascio, T. O. Yeates, Structure of a 16-nm cage designed by using protein oligomers. Science 336, 1129 (2012).
2. Y. T. Lai, K. L. Tsai, M. R. Sawaya, F. J. Asturias, T. O. Yeates, Structure and flexibility of nanoscale protein cages designed by symmetric self-assembly. J. Am. Chem. Soc. 135, 7738-7743 (2013).
3. J. E. Padilla, C. Colovos, T. O. Yeates, Nanohedra: using symmetry to design self assembling protein cages, layers, crystals, and filaments. Proc. Natl. Acad. Sci. U.S.A 98, 2217-2221 (2001).
4. Y. T. Lai et al., Designing and defining dynamic protein cage nanoassemblies in solution. Sci Adv 2, e1501855 (2016).
5. W. L. DeLano, M. H. Ultsch, A. M. de Vos, J. A. Wells, Convergent solutions to binding at a protein-protein interface. Science 287, 1279-1283 (2000).
6. Y. Gong, L. Zhang, J. Li, S. Feng, H. Deng, Development of the Double Cyclic Peptide Ligand for Antibody Purification and Protein Detection. Bioconjug Chem 27, 1569-1573 (2016).
7. H. J. Kang et al., Developing an antibody-binding protein cage as a molecular recognition drug modular nanoplatform. Biomaterials 33, 5423-5430 (2012). 8. C. D. Putnam, M. Hammel, G. L. Hura, J. A. Tainer, X-ray solution scattering
(SAXS) combined with crystallography and computation: defining accurate macromolecular structures, conformations and assemblies in solution. Q. Rev. Biophys. 40, 191-285 (2007).

Example 2

Materials and Methods

Dynamic Light Scattering (DLS) analysis of SAPNA binding of antibody. Samples were diluted in PBS pH 7.4 and run on a DynaPro™ Plate Reader III. The DLS acquisition time was 5 seconds and 5 acquisitions were taken per sample. The temperature was 20 degrees Celsius.

Primary human T cell expansion assay. Primary human pan-T cells (includes $CD4^+$ and $CD8^+$ T cells as well as some gamma/delta T cell subsets) isolated from peripheral blood (PB) mononuclear cells (MNCs) of a random donor were plated in a 96-well plate. Triplicate wells were treated with soluble SAPNA loaded with varying ratios of anti-CD3/anti-CD28 antibodies, or competing technologies on Day 1. Fresh xeno-free medium containing exogenous recombinant human IL-2 was added every 3-4 days. T cells were stained with the following: Live/Dead stain, anti-CD3, anti-CD4, anti-CD8, anti-CCR7, anti-CD45RA, and anti-CD95 antibodies. T cell differentiation was assessed via flow cytometry, using the literature-supported T cell subset identification staining scheme: $T_{CM}$ (CCR7+ CD45RA−), TEM (CCR7− CD45RA−), $T_{EMRA}$ (CCR7− CD45RA+), $T_{SCM}$ (CD45RA+ CCR7+ →CD95+), $T_{naive}$ (CD45RA+ CCR7+ →CD95−). Samples were run on an LSR Fortessa X20 Analyzer flow cytometer, and data analyzed using FlowJo 10.6.1.

CD8+ T cell isolation using magnetic bead-bound SAPNA. 14-day expanded primary human pan-T cells were plated in a 96-well plate. SAPNA was first incubated with magnetic Ni-NTA (mag) beads for 5 minutes at room temperature, and then a rabbit-anti-CD8 antibody was added and incubated for an additional 20 minutes. A control was prepared that withheld SAPNA from the mixture. The control and mag-SAPNA-CD8 beads were added to triplicate wells and the plate was returned to the 37 degrees Celsius, 5% $CO_2$ incubator for 1 hour. The cell-bead solution was resuspended and placed on a magnet for 2 minutes. The bead-bound component was attracted to the magnet, while the supernatant containing the cell suspension was transferred to a new plate for flow cytometry staining. Cells were stained and assessed the same as in the "Primary human T cell expansion assay" section.

Immunofluorescence microscopy. HeLa cells were cultured in a 37 degree Celsius, 5% $CO_2$ incubator, and seeded on coverslips. Cells were fixed in 4% paraformaldehyde in PBS+0.2% Triton X-100. They were then permeabilized for 30 minutes in PBS+0.5% Triton X-100 (PBST). Permeabilized cells were blocked for 30 minutes in PBST (+5% FBS). Control staining was done using the rabbit-anti-ROBO1 antibody and a goat-anti-rabbit-A488 secondary antibody. For the experimental group, SAPNA was chemically labeled with Alexa Fluor®-488, and incubated with rabbit-anti-ROBO1 for at least 30 minutes. The loaded SAPNA molecule was then incubated in PBST (+5% FBS) for 1 hr at room temperature. Coverslips were washed with PBST, and then PBS only. Coverslips were mounted using and antifade mounting media containing the DNA stain, DAPI.

Results

Figure 7:
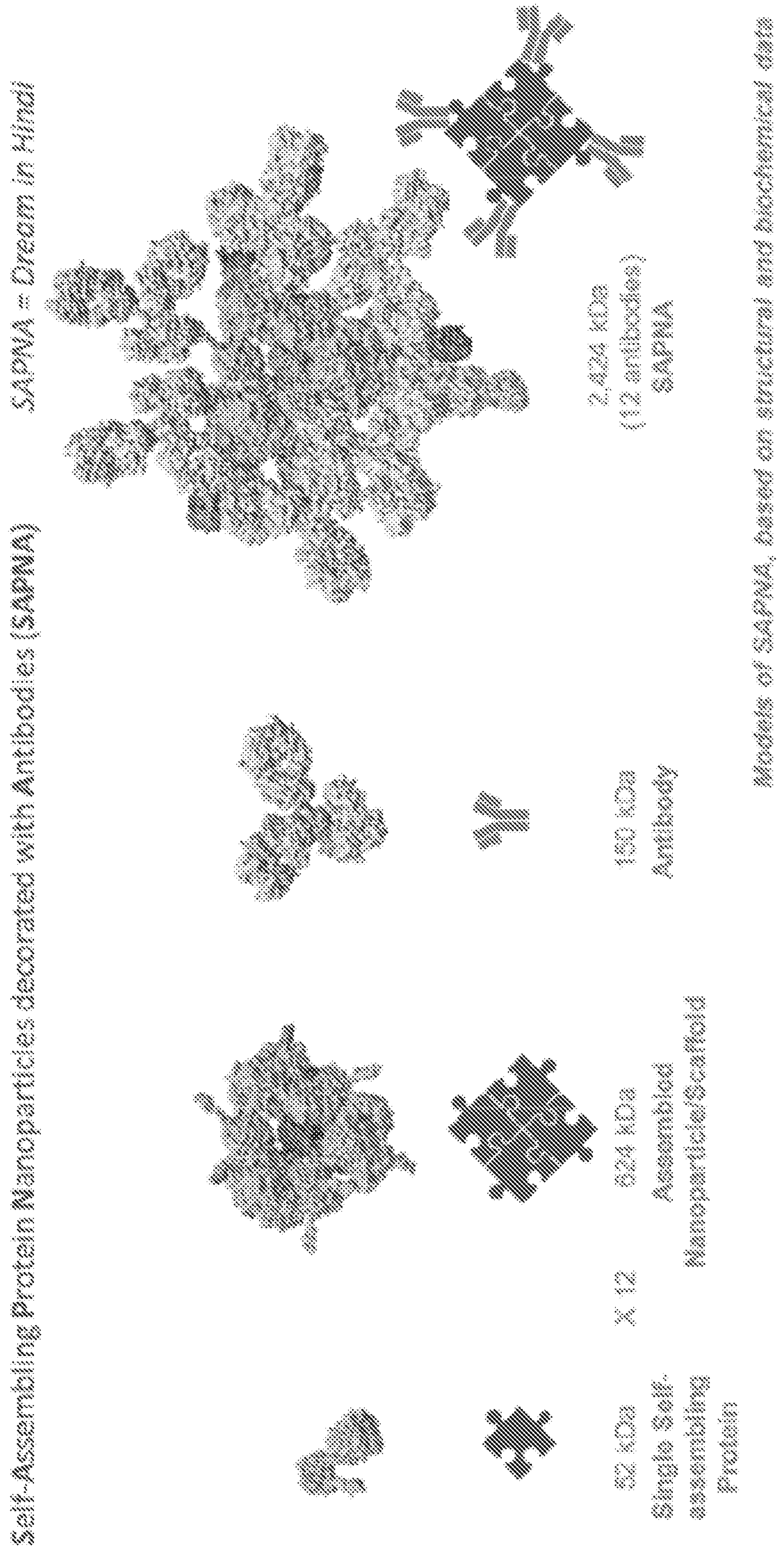
FIG. 7. SAPNA can be loaded with up to 12 antibodies.
Figure 8:
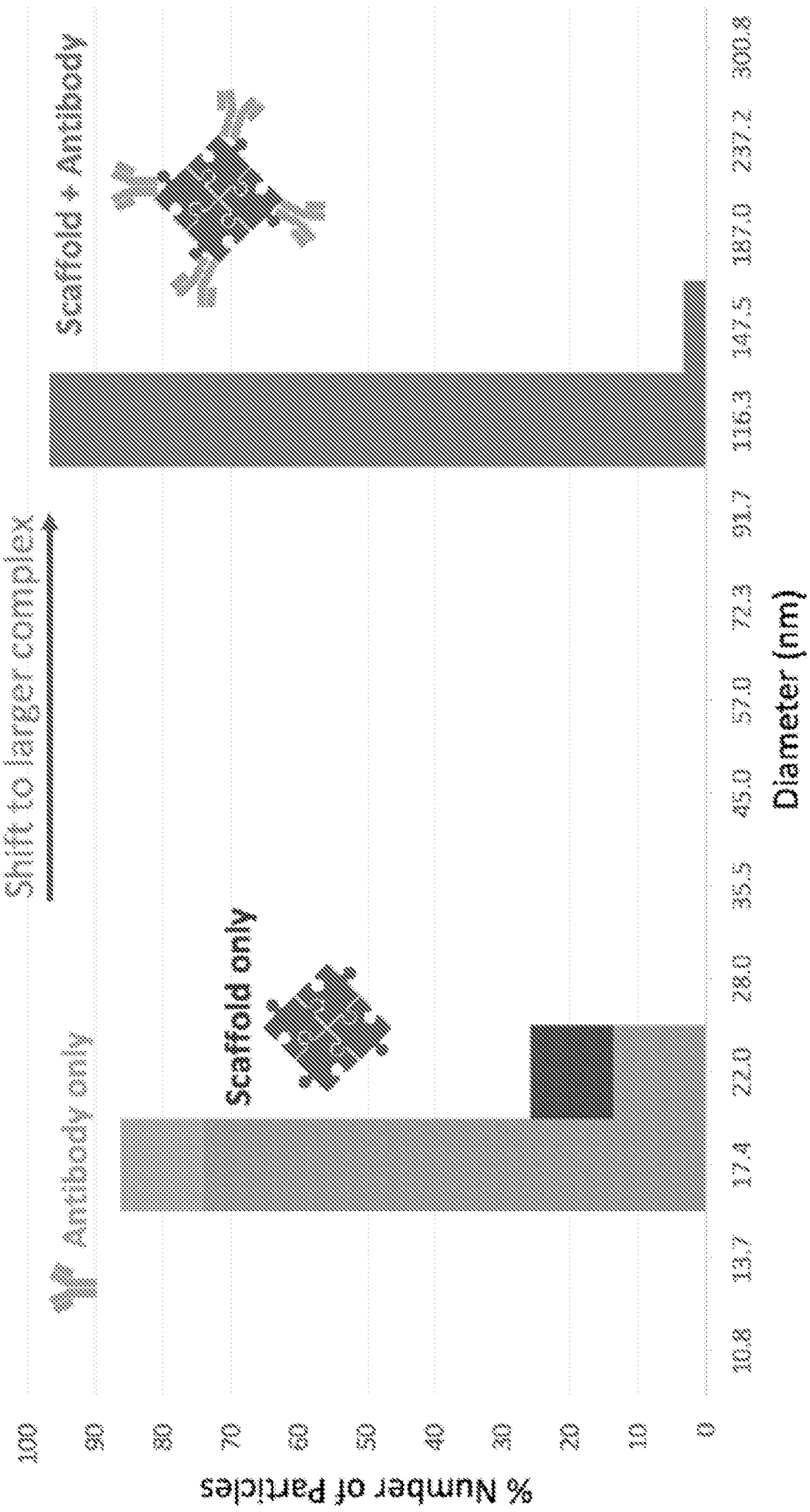
FIG. 8. Dynamic Light Scattering shows SAPNA loaded with a rabbit-anti-ROBO1 antibody.
Figure 9:
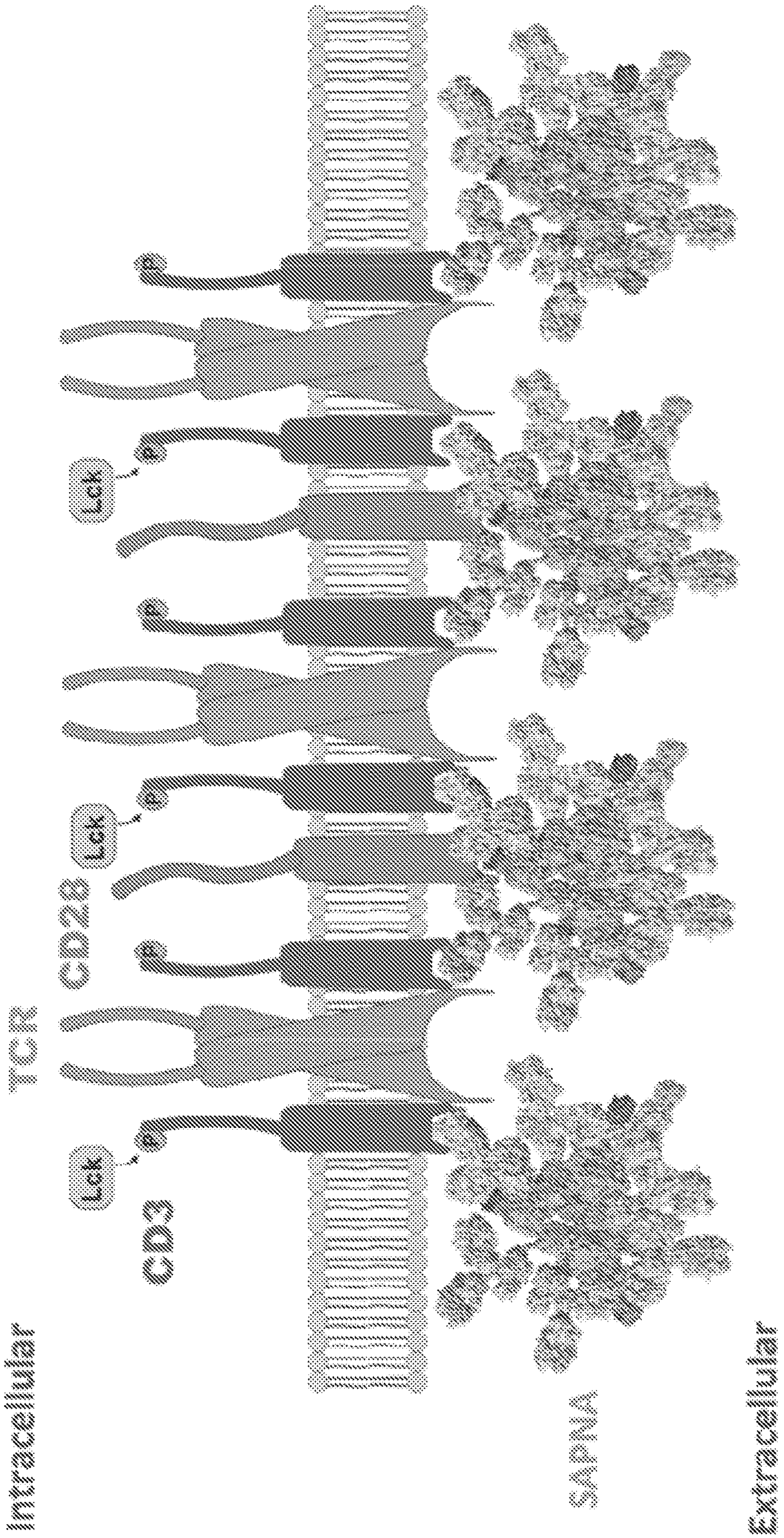
FIG. 9. Schematic of SAPNA enforcing receptor clustering at the T cell immunological synapse.

The SAPNA molecule has twelve potential antibody Fc binding sites, and can mount any human or rabbit IgG (FIG. 7). We demonstrate an example of SAPNA's abilities by binding it to a rabbit-anti-ROBO1 antibody (FIG. 8). We hypothesized that SAPNA could physically force cell-surface receptors into close proximity, which is a required step in the activation and expansion of T cells (FIG. 9).

Figure 10:
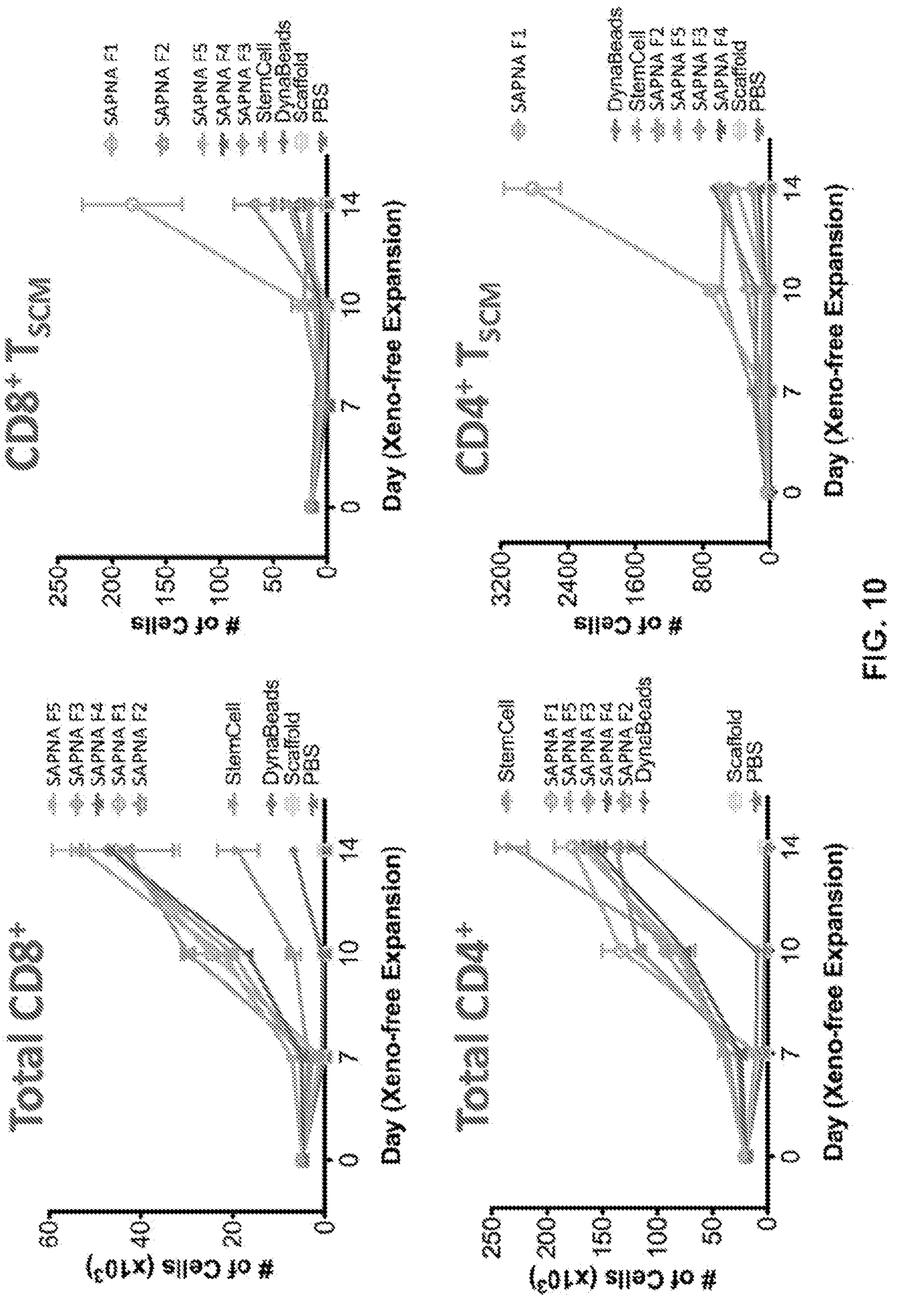
FIG. 10. SAPNA loaded with anti-CD3/anti-CD28 antibodies used to stimulate and expand blood donor-derived T cells over 14 days with flow cytometry as a readout. These data demonstrate superior primary T cell expansion abilities relative to two on-market technologies, ThermoFisher's Dynabeads CD3/CD28, and StemCell's ImmunoCult CD3/CD28.

To assess and benchmark SAPNA, we performed 14-day T cell expansions with clinically-relevant donor-derived peripheral blood T cells (FIG. 10). These data demonstrate that SAPNA produces a T cell product containing the highest number of cytotoxic $CD8^+$ T cells (FIG. 4—top left panel), which are the intended cells for engineering with chimeric antigen receptors (CARs) meant to target them to cancer cells. SAPNA performs in the top 2 for $CD4^+$ T cell expansion relative to competing technologies (FIG. 10—bottom left panel); these are an important component of the final CAR T cell product[1]. Additionally, it has been shown that T cell subsets with a more stem-like phenotype, such as memory stem ($T_{SCM}$) T cells, have the greatest long-term anti-cancer efficacy in vivo and it is therefore very therapeutically valuable to have increased numbers of these present in the final expanded CAR T cell product (Turtle, C. J. et al. CD19 CAR-T cells of defined CD4+:CD8+ composition in adult B cell ALL patients. *J. Clin. Invest.* 126, 2123-2138 (2016); Gattinoni, L. et al. Wnt signaling arrests effector T cell differentiation and generates CD8+ memory stem cells. *Nat. Med.* 15, 808-813 (2009)). The SAPNA technology produces the greatest number of $CD4^+$ and $CD8^+$ $T_{SCM}$ cells (FIG. 10—top & bottom right panels) during the expansion. Collectively, these data demonstrate that SAPNA is technically superior, and has the potential to generate greater numbers of CAR T cells with more efficacious anti-cancer activity.

Figure 11:
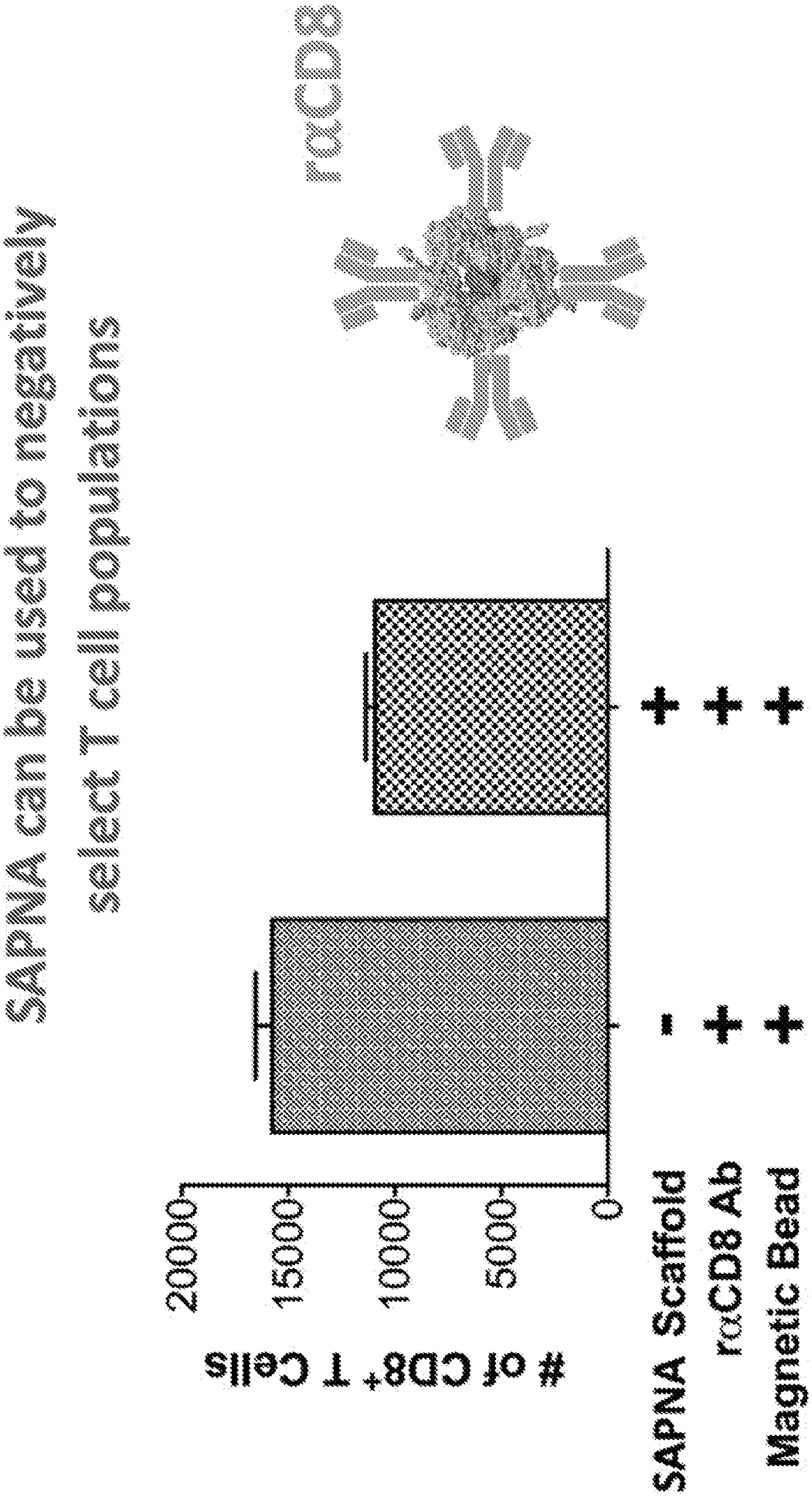
FIG. 11. SAPNA bound to beads can isolate (negatively select) T cell populations.

Due to the 12 his-tags on the SAPNA molecule (one on each monomer), we hypothesized that it could bind to magnetic nickel beads, while also binding and displaying antibodies. Through this dual action, we demonstrate that SAPNA can be used to isolate (or negatively select) cell populations with a particular cell-surface marker, such as CD8, from a mixed group of cells (FIG. 11).

Figure 12:
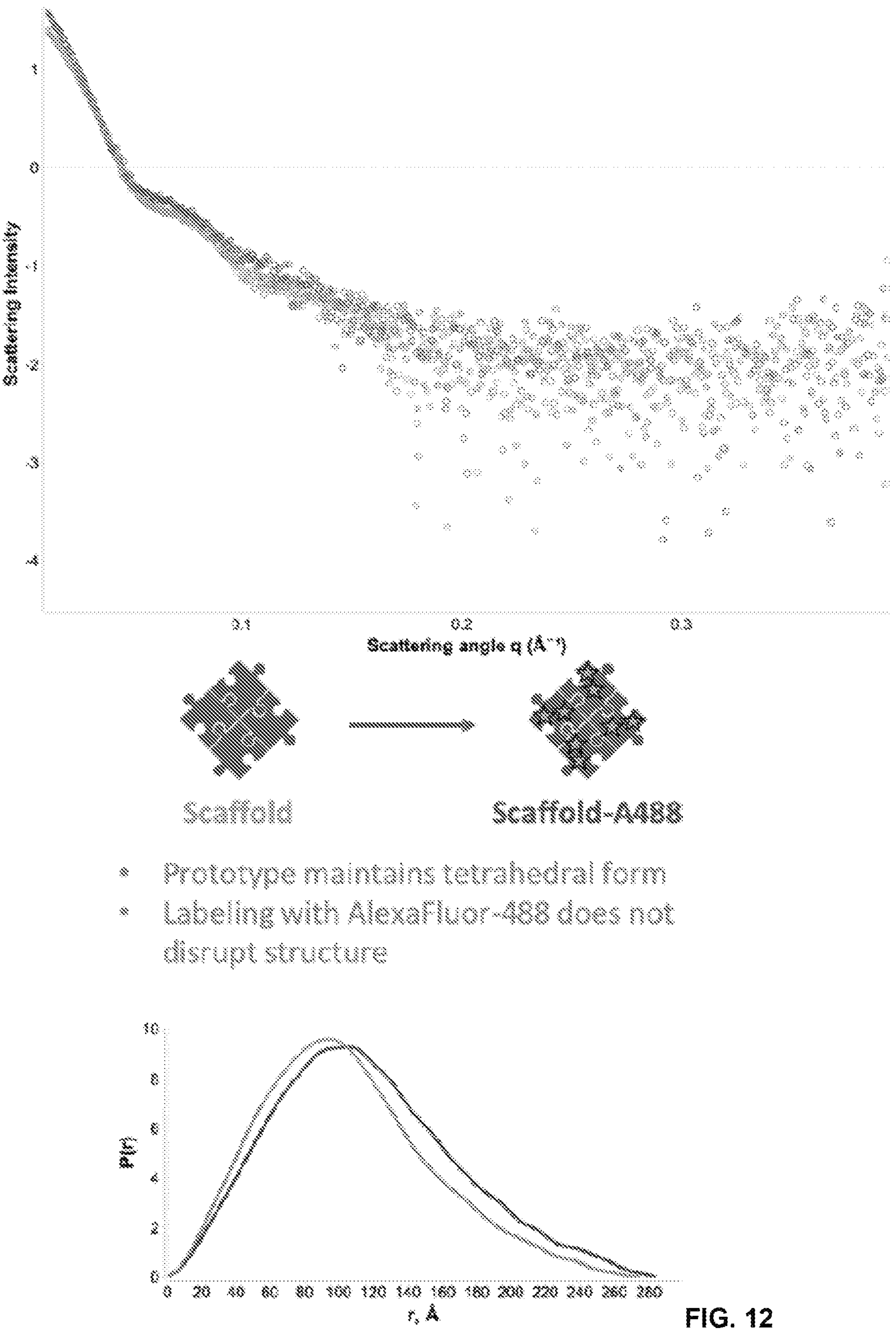
FIG. 12. SAPNA maintains its structure after chemical conjugation with Alexa Fluor®-488.
Figure 13:
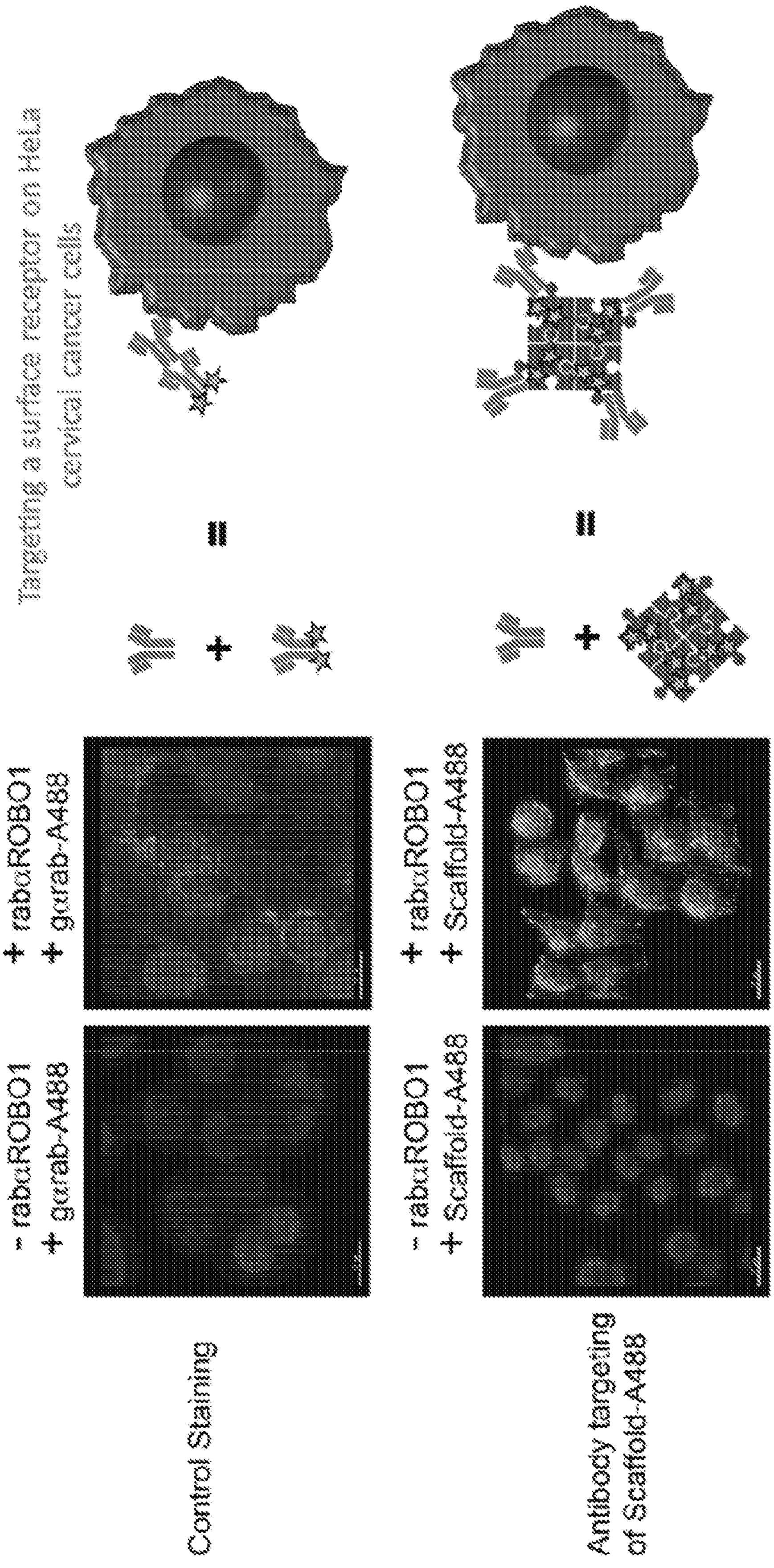
FIG. 13. Alexa Fluor®-488 labeled SAPNA binds to rabbit-anti-ROBO1 antibodies target to the surface of HeLa cervical cancer cells.

To evaluate if SAPNA could be targeted to the surface of cancer cells, we employed immunofluorescence microscopy. After using small angle X-ray scattering (SAXS) to validate that chemically labeling SAPNA with Alexa Fluor®-488 had little impact on its structure (FIG. 12), we targeted the labeled nanoparticle to the surface of HeLa cervical cancer cells by loading it with the same rabbit-anti-ROBO1 antibody as used for the DLS in FIG. 8. The 488-labeled SAPNA was specifically targeted to the surface of the cells (FIG. 13).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

All cited references are hereby each specifically incorporated by reference in their entireties.

What is claimed is:

1. A protein cage polypeptide, or scaffolding protein, capable of forming a hollow tetrahedral pyramid structure, wherein the protein cage polypeptide, or scaffolding protein; comprises an amino acid sequence that specifically binds to an antibody or part thereof, wherein the protein cage polypeptide, or scaffolding protein, comprises the following structure: Polypeptide 1-AHL-Polypeptide 2-INSERT A-Polypeptide 3-INSERT B-Polypeptide 4; wherein AHL is an "alpha helical linker" and wherein INSERT A and/or INSERT B each independently comprise the amino acid sequence DCAWHLGELVWCT (SEQ ID NO:41) or GCDCAWHLGELVWCTCG (SEQ ID NO:42) and the protein cage polypeptide comprises an amino acid sequence that comprises any one of SEQ ID Nos:20-39.

2. The protein cage polypeptide, or scaffolding protein, of claim 1, wherein INSERT A has a length of about 17 to about 25 amino acids and/or INSERT B has a length of about 28 to about 85 amino acids.

3. The protein cage polypeptide of claim 1, wherein Polypeptide 1 comprises an amino acid sequence comprising amino acid identity to the amino acid sequence from the N-terminus to up to the AQEAQKQK sequence of any one of SEQ ID Nos:20-39.

4. The protein cage polypeptide of claim 1, wherein Polypeptide 1 comprises an amino acid sequence comprising the following: YGTAR, TDD, LXENLGTR, IDV, TGXRT, and/or SA; wherein X is any charged amino acid residue.

5. The protein cage polypeptide of claim 1, wherein Polypeptide 1 comprises about 278 to about 303 amino acid residues.

6. The protein cage polypeptide of claim 1, wherein AHL comprises an amino acid sequence comprising: AQEAQKQK.

7. The protein cage polypeptide of claim 1, wherein AHL comprises about 5, 6, 7, 8, 9, 10, or 11 amino acid residues.

8. The protein cage polypeptide of claim 1, wherein Polypeptide 2 comprises an amino acid sequence comprising amino acid identity to the amino acid sequence from the C-end of the AQEAQKQK sequence to the N-end of INSERT A of any one of SEQ ID Nos:20-39.

9. The protein cage polypeptide of claim 1, wherein Polypeptide 2 comprises an amino acid sequence comprising the following: LTEVETYVLS (SEQ ID NO:43).

10. The protein cage polypeptide of claim 1, wherein Polypeptide 2 comprises about 30 to about 36 amino acid residues.

11. The protein cage polypeptide of claim 1, wherein Polypeptide 3 comprises an amino acid sequence comprising amino acid identity to the amino acid sequence from the C-end of INSERT A to the N-end of INSERT B of any one of SEQ ID Nos:20-39.

12. The protein cage polypeptide of claim 1, wherein Polypeptide 3 comprises an amino acid sequence comprising the following: FTLTVPSERGLQR (SEQ ID NO:44) and/or CATCEQIAD (SEQ ID NO:45).

13. The protein cage polypeptide of claim 1, wherein Polypeptide 3 comprises about 110 to about 130 amino acid residues.

14. The protein cage polypeptide of claim 1, wherein Polypeptide 3 comprises 121 amino acid residues.

15. The protein cage polypeptide of claim 1, wherein Polypeptide 4 comprises an amino acid sequence comprising amino acid identity to the amino acid sequence from the C-end of INSERT B to an amino acid sequence comprising: EHHHHHH of any one of SEQ ID Nos:20-35 or 37-39.

16. The protein cage polypeptide of claim 1, wherein Polypeptide 4 comprises about 5 to about 13 amino acid residues.

17. The protein cage polypeptide of claim 1, wherein Polypeptide 4 comprises 8 amino acid residues.

18. The protein cage polypeptide of claim 1, wherein the protein cage polypeptide comprises the amino acid sequence of any one of SEQ ID Nos:20-39.

19. The protein cage polypeptide of claim 18, wherein the protein cage polypeptide comprises an amino acid sequence comprising any one or more, or all, charged amino acids that are bolded and underlined as follows (SEQ ID NO: 40)
MPFITVGQENSTSIDLYYEDHGTGTPVVLIHGFPLSGHSWERQSAALLDA

GYRVITYDRRGFGQSSQPTTGYDYDTFAADLNTVLETLDLQDAVLVGFSM

GTGEVARYVSSYGTARIAAVAFLASLEPFLLKTDDNPDGAAPQEFFDGIV

AAVKADRYAFYTGFFNDFYNLDENLGTRISEEAVRNSWNTAASGGFFAAA

AAPTTWYTDFRADIPRIDVPALILHGTGDRTLPIENTARVFHKALPSAEY

VEVEGAPHGLLWTHAEEVNTALLAFLAKAQEAQKQKLLTEVETYVLSIIP

SGPLKAEIAQRLEDVFAGKNTDLEVLMEWLKTRPILSPLTKGILGFVFTL

TVPSERGLQRRRFVQNALNGNGDPNNMDKAVKLYRKLKREITFHGAKEIS

LSYSAGALASCMGLIYNRMGAVTTEVAFGLVCATCEQIADSQHRSHRQLE

HHHHHH.

20. The protein cage polypeptide of claim 1, wherein the protein cage polypeptide comprises a polypeptide of from about 400 to about 700 amino acid residues.

21. The protein cage polypeptide of claim 20, wherein the protein cage polypeptide comprises a polypeptide of from about 450 to about 650 amino acid residues.

22. The protein cage polypeptide of claim 1, wherein the antibody is an IgG antibody.

23. The protein cage polypeptide of claim 1, wherein the part of the antibody is a Fc region of an IgG antibody.

24. The protein cage polypeptide of claim 22, wherein the IgG antibody is a human IgG antibody.

25. The protein cage polypeptide of claim 23, wherein the Fc region of an IgG antibody is part of an Fc chimeric protein.

26. The protein cage polypeptide, or scaffolding protein, of claim 1, wherein the binding affinity $K_a$ of the protein cage polypeptide, or scaffolding protein, to the antibody or part thereof, is equal to or greater than $10^7$ $M^{-1}$.

27. The protein cage polypeptide, or scaffolding protein, of claim 1, wherein the protein cage polypeptide, or scaffolding protein, specifically binds to the antibody or part thereof, or any chimeric protein, molecule or compound comprising the antibody, or part thereof.

28. A hollow tetrahedral pyramid structure comprising twelve protein cage polypeptides of claim 1 assembled as the tetrahedral pyramid structure.

29. A "self-assembling protein nanoparticle decorated with antibodies" (SAPNA) which is a chimeric protein assembly comprising: (a) one or more antibodies and (b) a protein cage polypeptide of claim 1 that provides a scaffold upon which to array the antibodies, wherein the one or more antibodies are bound to the INSERT A and/or INSERT B of the protein cage polypeptide.

30. A "self-assembling protein nanoparticle decorated with antibodies" (SAPNA) structure comprising: (1) one protein cage polypeptide or scaffolding protein of claim 1, or a plurality thereof assembled into a 3-dimensional assembly, (2) optionally one or more human or rabbit IgG antibodies, (3) optionally an IgG binding loop, and (4) optionally, when the plurality of polypeptides or scaffolding proteins (or engineered protein cage proteins (PCs)) are assembled into a 3-dimensional assembly, a cargo of interest confined or enclosed by the 3-dimensional assembly.

31. A method for detecting or isolating a pathogenic biological agent, or part thereof, the method comprising: a) providing a "self-assembling protein nanoparticle decorated with antibody" (SAPNA) of claim 30 wherein the antibody is capable of binding specifically to a pathogenic biological agent, or part thereof, (b) contacting the SAPNA with a sample comprising the pathogenic biological agent, or part thereof, such that the SAPNA binds the pathogenic biological agent, or part thereof; (c) detecting the SAPNA pathogenic biological agent, or part thereof via detection, and/or separating the SAPNA bound pathogenic biological agent, or part thereof, from the rest of the sample; and (d) determining the abundance of the pathogenic biological agent, or part thereof.

* * * * *